United States Patent
Johns et al.

(10) Patent No.: US 9,663,459 B2
(45) Date of Patent: May 30, 2017

(54) PREPARATION OF SURFACTANTS VIA CROSS-METATHESIS

(71) Applicant: MATERIA, INC., Pasadena, CA (US)

(72) Inventors: Adam M. Johns, Claremont, CA (US); Richard L. Pederson, San Gabriel, CA (US); Rosemary Conrad Kiser, Sierra Madre, CA (US)

(73) Assignee: MATERIA, INC., Pasadena, CA (US)

( * ) Notice: Subject to any disclaimer, the term of this patent is extended or adjusted under 35 U.S.C. 154(b) by 0 days.

(21) Appl. No.: 14/782,935

(22) PCT Filed: Apr. 9, 2014

(86) PCT No.: PCT/US2014/033568
§ 371 (c)(1),
(2) Date: Oct. 7, 2015

(87) PCT Pub. No.: WO2014/169080
PCT Pub. Date: Oct. 16, 2014

(65) Prior Publication Data
US 2016/0145204 A1    May 26, 2016

Related U.S. Application Data

(60) Provisional application No. 61/941,820, filed on Feb. 19, 2014, provisional application No. 61/810,056, filed on Apr. 9, 2013.

(51) Int. Cl.
*C07C 309/00*    (2006.01)
*C07C 303/32*    (2006.01)
(Continued)

(52) U.S. Cl.
CPC .............. *C07C 303/32* (2013.01); *C07C 2/02* (2013.01); *C07C 2/74* (2013.01); *C07C 5/03* (2013.01);
(Continued)

(58) Field of Classification Search
CPC .................................................... C07C 303/32
(Continued)

(56) References Cited

U.S. PATENT DOCUMENTS 3,732,323 A * 5/1973 Osaki et al. .............. C07C 2/04
585/438
3,848,010 A   11/1974 Intille
(Continued)

FOREIGN PATENT DOCUMENTS

NL   WO 2004101476 A1 * 11/2004 ........... C07C 269/06
WO   02/079208 A2   10/2002
(Continued)

OTHER PUBLICATIONS

International Search Report and Written Opinion in International Application No. PCT/US2014/033568, dated Aug. 27, 2014.
(Continued)

*Primary Examiner* — Deborah D Carr
(74) *Attorney, Agent, or Firm* — J.A. Lindeman & Co., PLLC

(57) ABSTRACT

The present invention relates to compositions comprising alkene benzenes or alkene benzene sulfonates or alkylbenzenes or alkylbenzene sulfonates; methods for making alkene benzenes or alkene benzene sulfonates or alkylbenzenes or alkylbenzene sulfonates; where the benzene ring is optionally substituted with one or more groups designated R*, where R* is defined herein. More particularly, the present invention relates to compositions comprising 2-phenyl linear alkene benzenes or 2-phenyl linear alkene benzene sulfonates or 2-phenyl linear alkylbenzenes or 2-phenyl linear alkylbenzene sulfonates; methods for making 2-phenyl alkene benzenes or 2-phenyl alkene benzene sulfonates or 2-phenyl alkylbenzenes or 2-phenyl alkylbenzene sulfonates; where the benzene ring is optionally substituted (Continued)

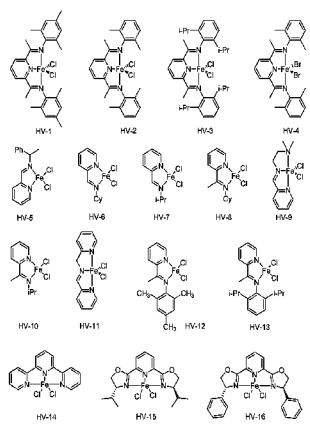

Chemical structures of hydrovinylation catalysts HV-1 to HV-16.

with one or more groups designated R*, where R* is defined herein.

7 Claims, 8 Drawing Sheets

(51) Int. Cl.
    *C07C 303/06*     (2006.01)
    *C07C 2/02*     (2006.01)
    *C07C 5/03*     (2006.01)
    *C07C 6/04*     (2006.01)
    *C07C 2/74*     (2006.01)

(52) U.S. Cl.
    CPC .............. *C07C 6/04* (2013.01); *C07C 303/06* (2013.01); *C07C 2521/18* (2013.01); *C07C 2523/44* (2013.01); *C07C 2531/18* (2013.01); *C07C 2531/22* (2013.01); *C07C 2531/24* (2013.01)

(58) Field of Classification Search
    USPC ......................................................... 562/95
    See application file for complete search history.

(56) References Cited

U.S. PATENT DOCUMENTS

| | | |
|---|---|---|
| 5,227,561 A | 7/1993 | Drent |
| 5,312,940 A | 5/1994 | Grubbs et al. |
| 5,342,909 A | 8/1994 | Grubbs et al. |
| 5,969,170 A | 10/1999 | Grubbs et al. |
| 6,111,121 A | 8/2000 | Grubbs et al. |
| 6,531,562 B2 | 3/2003 | Jung et al. |
| 6,562,776 B1 | 5/2003 | Smith et al. |
| 6,613,910 B2 | 9/2003 | Grubbs et al. |
| 6,759,537 B2 | 7/2004 | Grubbs et al. |
| 6,887,839 B2 | 5/2005 | Smith et al. |
| 6,921,735 B2 | 7/2005 | Hoveyda et al. |
| 6,995,127 B1 | 2/2006 | Smith et al. |
| 7,060,852 B2 | 6/2006 | Maas et al. |
| 7,329,758 B1 | 2/2008 | Grubbs et al. |
| 2003/0055262 A1 | 3/2003 | Grubbs et al. |
| 2007/0155975 A1* | 7/2007 | Grubbs .................... C07C 6/04 556/81 |
| 2010/0145086 A1 | 6/2010 | Schrodi et al. |
| 2012/0213726 A1 | 8/2012 | Green et al. |

FOREIGN PATENT DOCUMENTS

| | | |
|---|---|---|
| WO | 03/011455 A1 | 2/2003 |
| WO | 2004/101476 A1 | 11/2004 |
| WO | 2012/097379 A2 | 7/2012 |
| WO | 2012/129482 A2 | 9/2012 |
| WO | 2012/138423 A1 | 10/2012 |

OTHER PUBLICATIONS

Arai et al., "1,2-Asymmetric Induction in the SN2'-Allylation of Organocopper and Organozinc Reagents," J. Org. Chem. 1993, 58, pp. 5121-5129.
Doe et al., "Surfactants for Producing Low Interfacial Tensions I: Linear Alkyl Benzene Sulfonates," J. Am. Oil Chem. Soc. vol. 54, pp. 570-577.
Fassina et al., "Nickel Catalyzed Hydrovinylation of Arylethylenes: General Method of Synthesis of -Arylpropionic Acids Intermediates," Tetrahedron 56 (2000), pp. 7403-7409.
Grutters et al., "Highly Selective Cobalt-Catalyzed Hydrovinylation of Styrene," Adv. Synth. Catal. 2009, 351, pp. 2199-2208.
Grutters et al., "Highly Selective Cobalt-Catalyzed Hydrovinylation of Styrene," J. Am. Chem. Soc., 2006, 128, pp. 7414-7415 and supportive information.
Glasspoole et al., "Suzuki-Miyaura cross-couplings of secondary allylic boronic esters," Chem. Commun., 2012, 48, pp. 1230-1232.
Hoveyda et al., "H-Bonding as a Control Element in Stereoselective Ru-Catalyzed Olefin Metathesis," J. Am. Chem. Soc., 2009, 131, pp. 8378-8379 and supporting information.
Ceder et al., "Hydrovinylation of styrene derivatives to 3-aryl-1-butenes catalysed by nickel complexes," J. Mol. catalysis 92, (1994), pp. 127-139.
T.V. Rajanbabu "Asymmetric Hydrovinylation Reaction," Chem. Rev., 2003, 103, pp. 2845-2860.
T.V. Rajanbabu "In Pursuit of an Ideal C-C Bond-Forming Reaction: Development and Applications of the Hydrovinylation of Olefins," NIH Author Manuscript, Synlett, PMC Jul. 14, 2009, pp. 1-96.
Sanchez et al., "A Ruthenium-Based Catalyst System for Hydrovinylation at Room Temperature," Organomettallics, 2008, 27, pp. 2902-2904.
Dewey L. Smith, "Impact of Composition on the Performance of Sodium Linear Alkylbenzenesulfonate (NaLAS)1," JAOCS, vol. 74, No. 7 (1007), pp. 837-845.
Van Zijl et al., "Catalytic Enantioselective Synthesis of Vicinal Dialkyl Arrays," J. Org. Chem., 2008, 73, pp. 6994-7002.
Yi et al., "Hydrovinylation and [2+2] Cycloaddition Reactions of Alkynes and Alkenes Catalyzed by a Well-Defined Cationic Ruthenium-Alkylidene Complex," Organometallics, vol. 18, No. 11, 1999, pp. 2043-2045 and supportive information.
Yi et al., "Hydrovinylation of Alkenes Catalyzed by the Ruthenium-Hydride Complex Formed in Situ from (PCy3)2(CO) RuHCl and HBF4 OEt2," Organometallics, 2001, 20, pp. 802-804.
Alexakis et al., "Enantioselective Copper-Catalyzed Conjugate Addition and Allylic Substitution Reactions," Chem. Rev., 2008, 108, pp. 2796-2823.
Anderson et al., "Kinetic Selectivity of Olefin Metathesis Catalysts Bearing Cyclic (Alkyl((Amino)Carbenes," Organometallics, 2008, 27, pp. 563-566.
R. Banks & G. Bailey, "Olefin Disproportionation, A new Catalytic Process," I & EC Product Research and Dev., vol. 3, No. 3, Sep. 1964, pp. 170-173.
Burdett et al., "Renewable Monomer Feedstocks via Olefin Metathesis: Fundamental Mechanistic Studies of Methyl Oleate Ethenolysis with the First-Generation Grubbs Catalyst," Organometallics, 2004, 23, pp. 2027-2047.
Bussas et al., "Ene Reaction Mechanisms. 1. Chirality Transfer to the Enophile 4-Methyl-N-sulfinylbenzenesulfonamide," J. Org. Chem., vol. 48, No. 17, 1983, pp. 2828-2832.
Calderon et al., "Olefin Metathesis—A Novel Reaction for Skeletal Transformations of Unsaturated Hydrocarbons," Tetrahedron Letters, No. 34, 1967, pp. 3327-3329.
Ceder et al., "Metal catalysed hydrovinylation," Catal. Sci. Technol., 2013, 3, pp. 1446-1464.
Couturier et al., "A Cyclometalated Aryloxy(chloro)neopentylidene-tungsten Complex: A Highly Active and Stereoselective Catalyst for the Metathesis of cis- and trans-2-Pentene, Norbornene, 1-Methyl-norbornene, and Ethyl Oleate," Agnew. Chem. Int. Ed. Engl., 31, 1992, No. 5, pp. 628-631.
Dzhemilev et al., "Reaction of 2-Vinylfuran with Ethylene Catalyzed by Complexes of Nickel and Rhodium," Bull Acad. Sci. USSR, No. 9, 1976, p. 2146.
R. Grubbs & S. Chang, "Recent Advances in Olefin Metathesis and Its Application in Organic Synthesis," Tetrahedron 54, 1998, pp. 4413-4450.
Ishimura et al., "P NMR Study of Active Species for Ethylene Dimerization in sigma-Aryl Nickel Complex-AgClO4," Bull. Chem. Soc., Jpn. 56, 1983, pp. 818-821.
P. Jolly & G. Wilke, "Hydrovinylation," Applied Homogeneous Catalysis with Organometallic Compounds, Wiley-VCH Verlag GmbH, 2002, pp. 1164-1189.
Kawamoto et al., "The Codimerizations of Styrene with Vinyl Compounds Catalyzed by Olefin-palladium(II) Chloride Complexes," Bull. Chem. Soc., Jpn. 44, 1971, pp. 1239-1243.
Kawata et al., "Codimerization of Ethylene and Styrene Catalyzed by Bis(triphenyl-phosphine)o-aryl Nickel(II) Halide-Trifluoroboron Etherate," Short Communications, 1971, pp. 3217.

(56) References Cited

OTHER PUBLICATIONS

I. Leymet & A. Siove, "Ring-opening polymerization of norbornene initiated by tungsten alkylidene complexes. Activation by AlCl3," Makromol. Chem., 190, 1989, pp. 2397-2405.
D. Liaw & C. Lin, "Effect of Lewis Acid on the Polymerization of tert-Butylacetylene Initiated by the New Tungsten Carbene Complex: Geometric Structure Control with High Cis Content," J. Polymer Sci., Part A: Polymer Chem., vol. 31, 1993, pp. 3151-3154.
G. A. Mamedaliev & A. G. Azizov, "Study on the Codimerization of Vinylaromatic Compounds with Ethylene in the Presence of Modified Nickel-Containing Catalysts," Polymer J., vol. 17, No. 10, 1985, pp. 1075-1084.
Marshall et al., "Condensation of Long-Chain alpha-Phosphono Carboxylates with Aldehydes," J. Org. Chem., 1886, 51, pp. 1735-1741.
Johannes C. Mol, "Olefin Metathesis over supported rhenium oxide catalysts," Catalysts Today, 51, 199, pp. 289-299.
J.C. Mol, "Industrial applications of olefin metathesis," J. Mol. Catalysis A: Chem., 213, 2004, pp. 39-45.
G. Muller & J. I. Ordinas, "Hydrovinylation of olefins catalyzed by cationic nickel complexes [Ni(2,4,6-Me3C6H2) (CH3CN)P2]BF4," J. Mol. Catalysis A:Chem., 125, 1997, pp. 97-108.
Nickel et al., "A Highly Efficient Olefin Metathesis Process for the Synthesis of Terminal Alkenes from Fatty Acid Esters," Top Catal, 2012, 55, pp. 518-523.
Nomura et al., "The Hydrovinylation Reaction: A New Highly Selective Protocol Amendable to Asymmetric catalysis," J. Am. Chem. Soc., 1998, 120, pp. 459-460.
Nozima et al., "Enhancement by Water of the Activity of sigma-Aryl Palladium(II) Catalyst for Codimerization of Ethylene with Styrene," Chem. Letts. by the Chem. Soc. Jpn., 1973, pp. 1163-1164.
"Survey of Catalyst Systems," Olefin Metathesis and Metathesis Polymerization, 1997, pp. 12-49.
Rajanbabu et al., "Heterodimerization of Olefins. 1. Hydrovinylation Reactions of Olefins That Are Amendable to Asymmetric Catalysis," J. Org. Chem., 2003, 68, pp. 8431-8446.
Sanford et al., "New Insights into the Mechanism of Ruthenium-Catalyzed Olefin Metathesis Reactions," J. Am. Chem. Soc., 2001, 123, pp. 749-750 with supportive information.
J. J. Scheibel, "The Evolution of Anionic Surfactant Technology to Meet the Requirements of the Laundry Detergent Industry," J. Surfactants & Detergents, vol. 7, No. 4, 2004, pp. 319-328.
Scoll et al., "Synthesis and Activity of a New Generation of Ruthenium-Based Olefin Metathesis Catalysts Coordinated with 1,3-Dimesityl-4,5-dihydroimidazol-2-ylidene Ligands," Org. Lett., 1999, vol. 1, No. 6. pp. 953-956.
Schrodi et al., "Ruthenium Olefin Metathesis Catalysts for the Ethenolysis of Renewable Feedstocks," Clean 2008, 36, (8), pp. 669-673.
Schwab et al., "Synthesis and Applications of RuCl2(=CHR')(PR3)2: The Influence of the Alkylidene Moiety on Metathesis Activity," J. Am. Chem. Soc., 1996, 118, pp. 100-110 and supporting information.
A. Singh, "The global linear alkylbenzene (LAB) industry has experienced depressed margins and feedstock shortages during the past few years, The following is an analysis of the industry's current state and its most likely future," Inform Mar. 2012, vol. 23(3), pp. 181-185.
Barry M. Trost & David L. Van Vranken, "Asymmetric Transition Metal-Catalyzed Allylic Alkylations," Chem. Rev. 1996, 96, pp. 395-422.
Barry M. Trost & Matthew L. Crawley, "Asymmetric Transition-Metal-Catalyzed Allylic Alkylations: Applications in Total Synthesis," Chem. Rev., 2003, 103, pp. 2921-2943.
Siegfried Warwel & Volker Siekermann, "Olefin-Metathesis mit homogenen Rheniumcarben-Komplexkatalysatoren," Makromel. Chem., Rapid Commun., 4, 1983, pp. 423-427.
Warwel et al., "Polymers and Surfactants on the basis of renewable resources," Chemosphere 43, 2001, pp. 39-48.
Zoller, "Handbook of Detergents: Part F Production," 142, CRC Press, Boca Raton, FL, 2009, p. 111.

\* cited by examiner

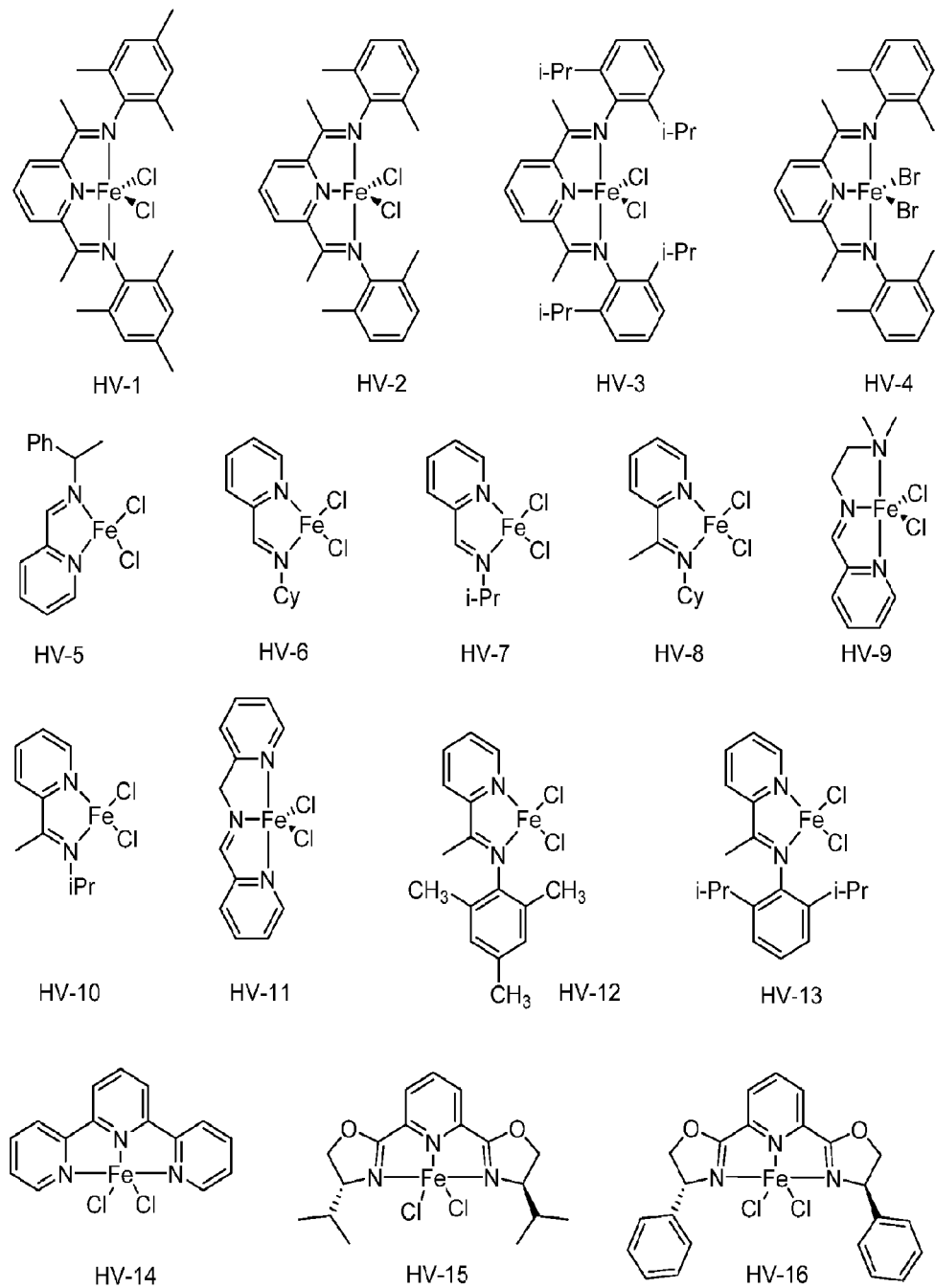
FIG.1 Chemical structures of hydrovinylation catalysts HV-1 to HV-16.

FIG. 2 $^1$H NMR of 3-phenyl-1-butene in $CDCl_3$.
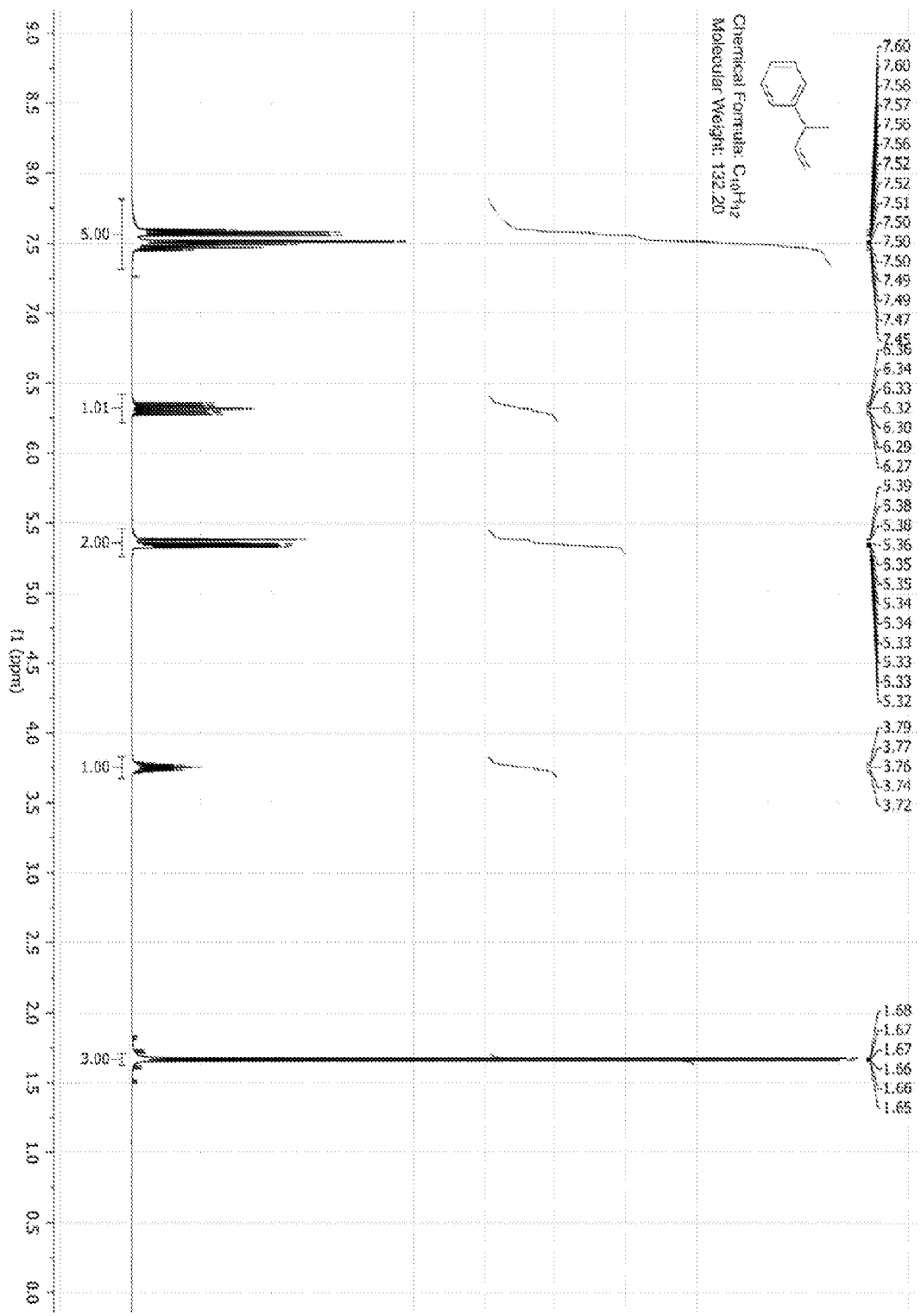

FIG. 3 $^1$H NMR of 3-tolyl-1-butene in CDCl$_3$.
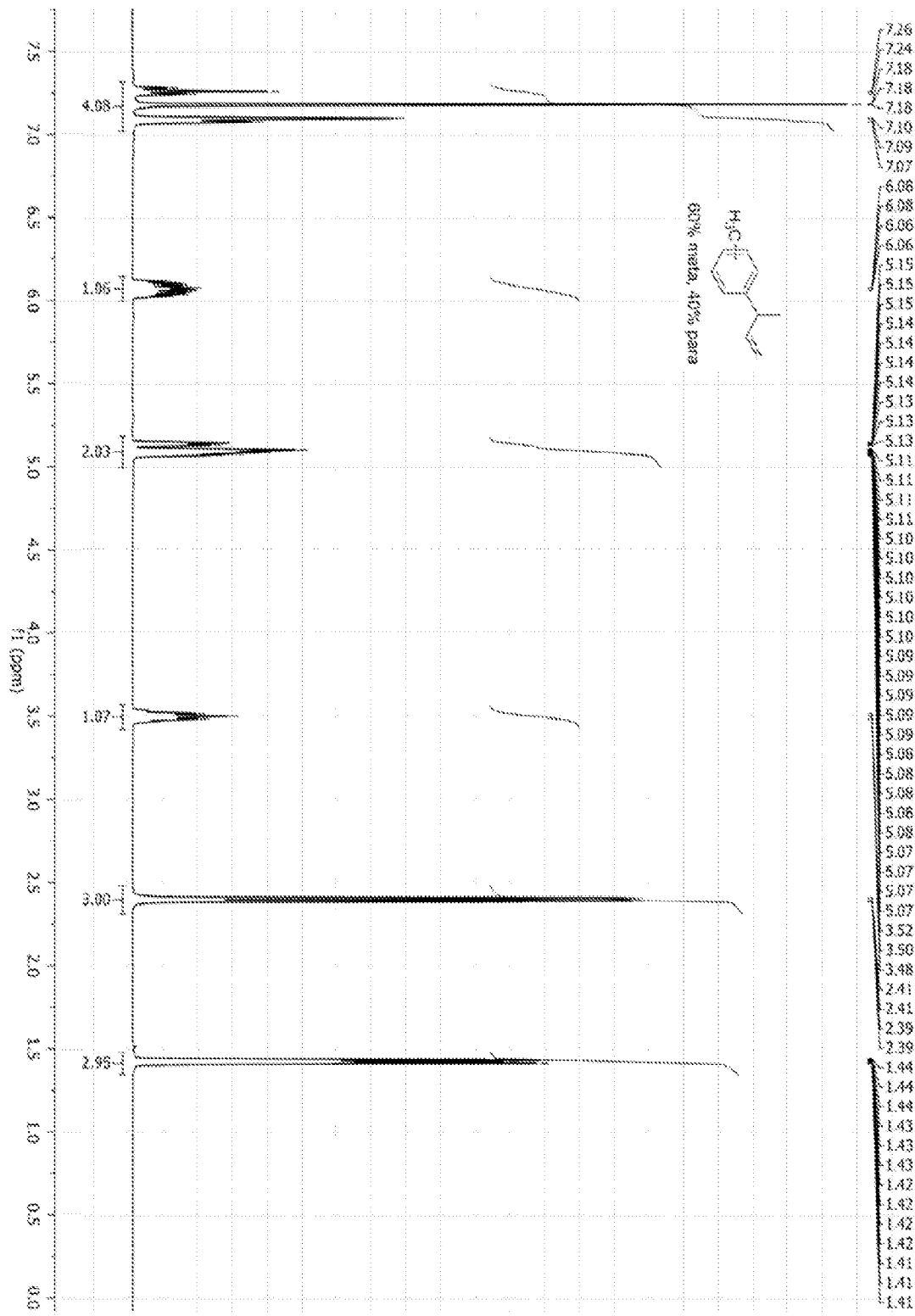

FIG. 4 $^{13}$C NMR of 3-tolyl-1-butene in CDCl$_3$.
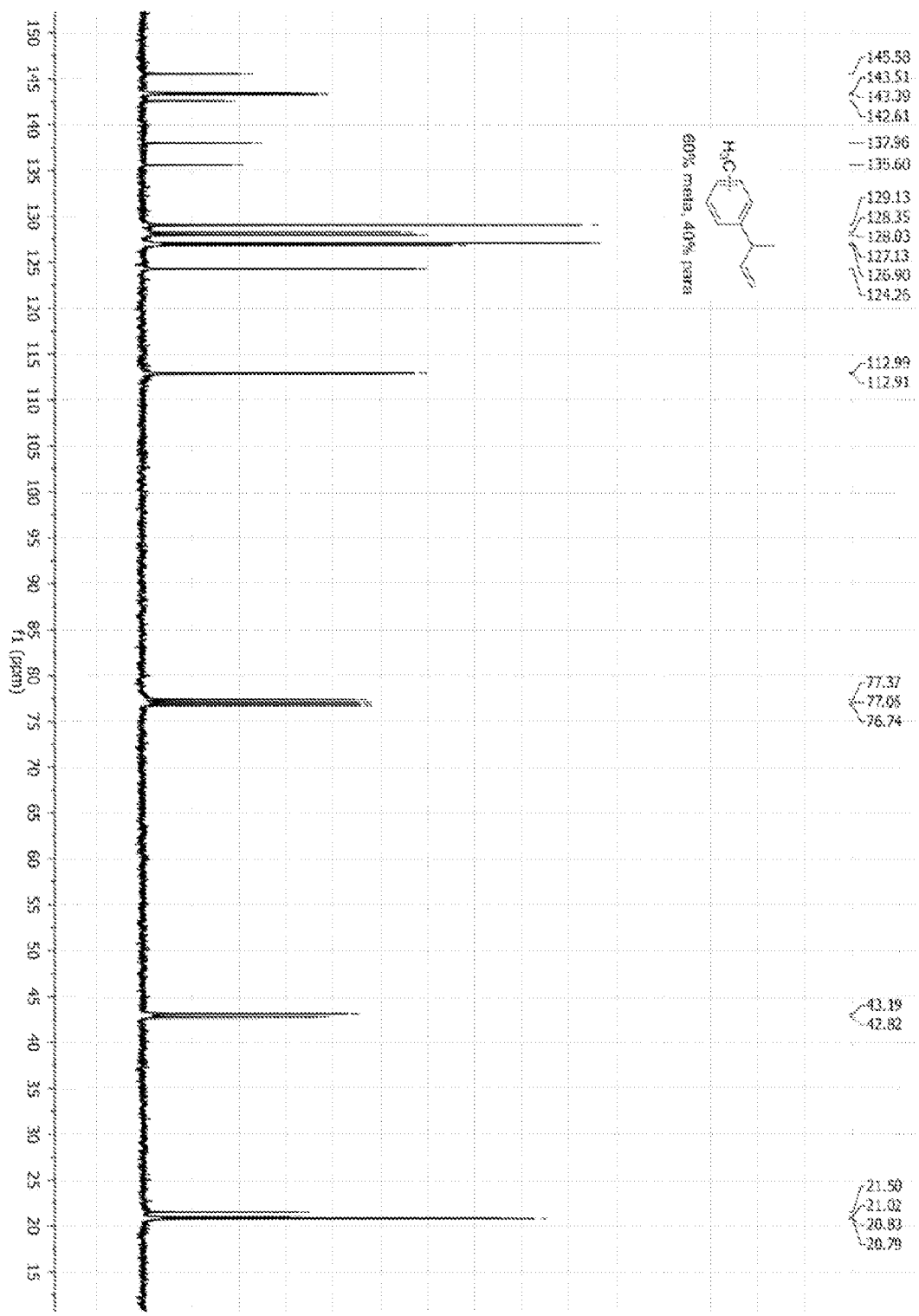

FIG. 5 Representative 2-phenyl-3-alkene structures.
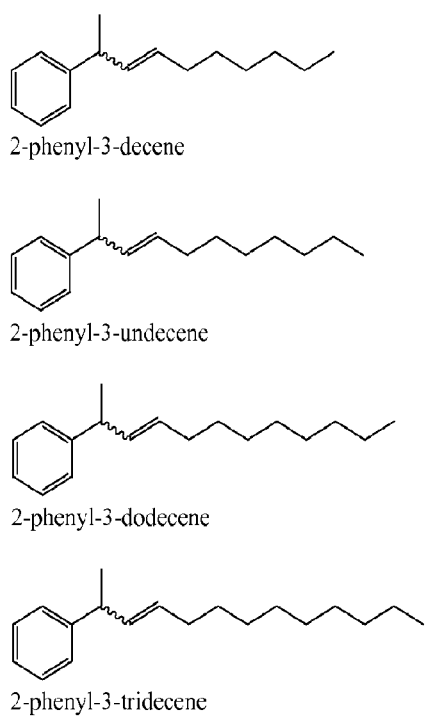

FIG. 6 Representative 2-(ortho-tolyl)-3-alkene structures.
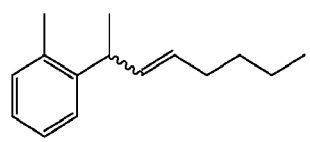
2-(ortho-tolyl)-3-octene
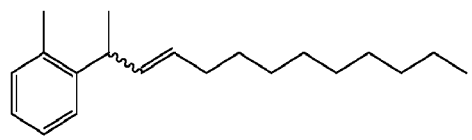
2-(ortho-tolyl)-3-tridecene
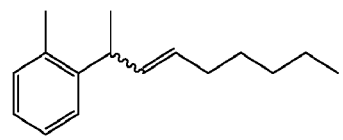
2-(ortho-tolyl)-3-nonene
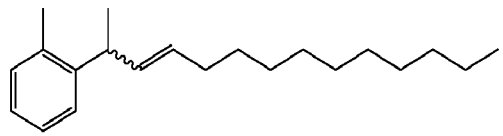
2-(ortho-tolyl)-3-tetradecene
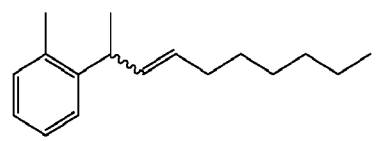
2-(ortho-tolyl)-3-decene
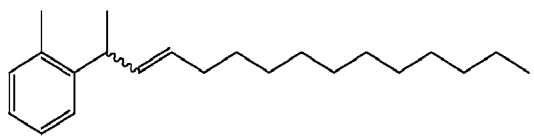
2-(ortho-tolyl)-3-pentadecene
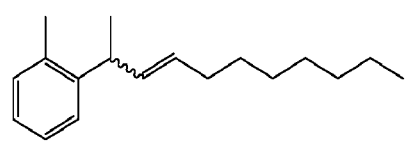
2-(ortho-tolyl)-3-undecene
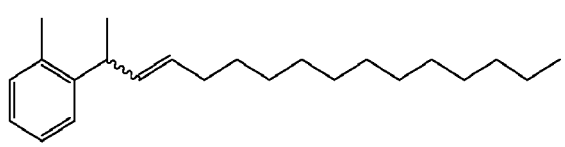
2-(ortho-tolyl)-3-hexadecene
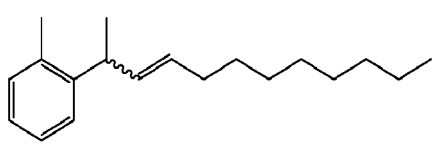
2-(ortho-tolyl)-3-dodecene

FIG. 7 Representative 2-(meta-tolyl)-3-alkene structures.
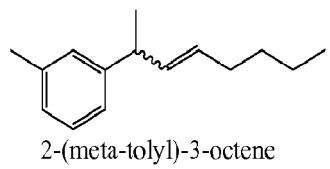
2-(meta-tolyl)-3-octene
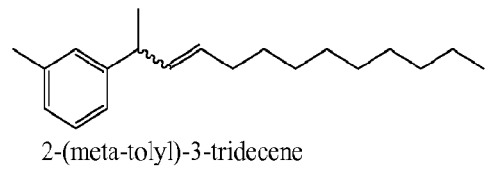
2-(meta-tolyl)-3-tridecene
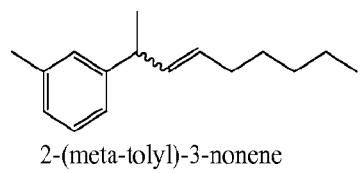
2-(meta-tolyl)-3-nonene
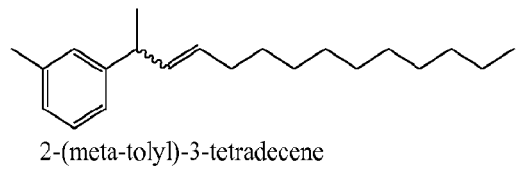
2-(meta-tolyl)-3-tetradecene
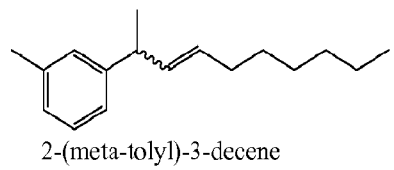
2-(meta-tolyl)-3-decene
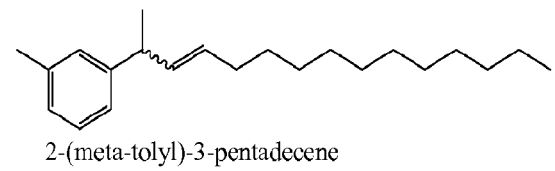
2-(meta-tolyl)-3-pentadecene
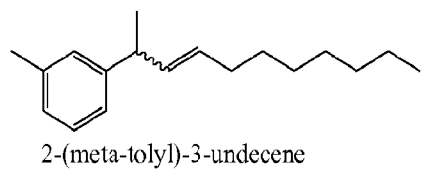
2-(meta-tolyl)-3-undecene
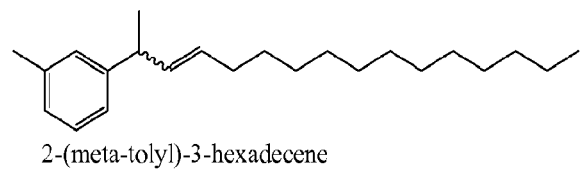
2-(meta-tolyl)-3-hexadecene
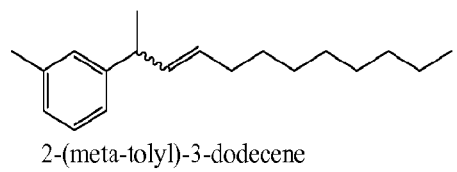
2-(meta-tolyl)-3-dodecene

FIG. 8 Representative 2-(para-tolyl)-3-alkene structures.
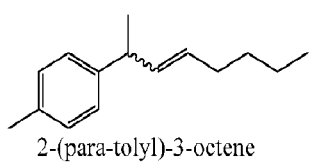
2-(para-tolyl)-3-octene
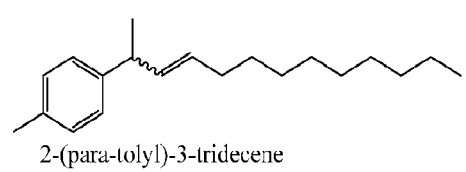
2-(para-tolyl)-3-tridecene
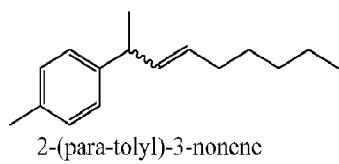
2-(para-tolyl)-3-nonene
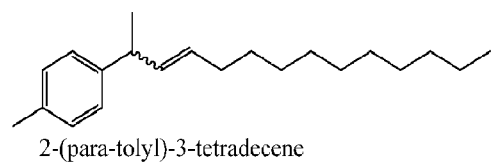
2-(para-tolyl)-3-tetradecene
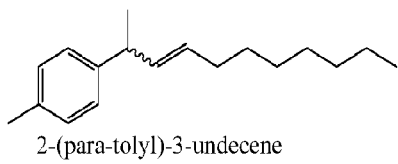
2-(para-tolyl)-3-undecene
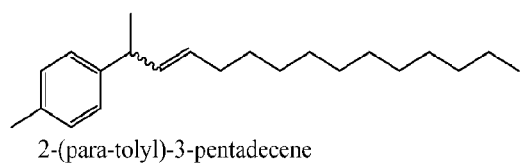
2-(para-tolyl)-3-pentadecene
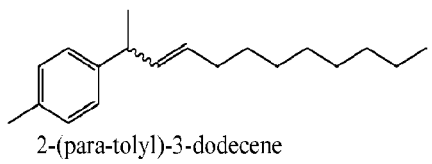
2-(para-tolyl)-3-dodecene
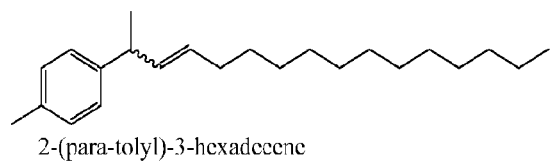
2-(para-tolyl)-3-hexadecene

PREPARATION OF SURFACTANTS VIA CROSS-METATHESIS

RELATED APPLICATIONS

This application claims the benefit of U.S. Provisional Patent Application No. 61/810,056, filed Apr. 9, 2013, and U.S. Provisional Patent Application No. 61/941,820, filed Feb. 19, 2014, and the contents of each are incorporated herein by reference.

TECHNICAL FIELD

This invention relates to compositions comprising alkene benzenes, compositions comprising alkene benzene sulfonates, methods for making alkene benzenes, methods for making alkene benzene sulfonates, compositions comprising alkylbenzenes, compositions comprising alkylbenzene sulfonates, methods for making alkylbenzenes, and methods for making alkylbenzene sulfonates. This invention relates to compositions comprising substituted alkene benzenes, compositions comprising substituted alkene benzene sulfonates, methods for making substituted alkene benzenes, methods for making substituted alkene benzene sulfonates, compositions comprising substituted alkylbenzenes, compositions comprising substituted alkylbenzene sulfonates, methods for making substituted alkylbenzenes, and methods for making substituted alkylbenzene sulfonates, where the benzene ring is substituted with one or more groups designated R*, where R* is defined herein. This invention describes a process to produce 2-phenyl linear alkyl benzene sulfonates (2-PhLAS) by cross metathesis of alpha-methyl styrene (AMS) or 3-phenyl-1-butene (3PhlC$_4$) with a linear alpha olefin (AO) or a linear internal olefin (IO) to produce 2-phenyl linear alkene benzenes (2-PhLAeB). The 2-phenyl linear alkene benzenes (2-PhLAeB) are hydrogenated and sulfonated by well-known methodologies to yield 2-phenyl linear alkylbenzene sulfonates (2-PhLAS). This invention describes a process to produce substituted 2-phenyl linear alkyl benzene sulfonates (2-Ph*LAS), where the benzene ring is substituted with one or more groups designated R*, by cross metathesis of substituted alpha-methyl styrene (AM*S), where the benzene ring is substituted with one or more groups designated R*, or substituted 3-phenyl-1-butene (3Ph*1C$_4$) where the benzene ring is substituted with one or more groups designated R*, with a linear alpha olefin (AO) or a linear internal olefin (IO) to produce substituted 2-phenyl linear alkene benzenes (2-Ph*LAeB), where the benzene ring is substituted with one or more groups designated R*, where R* is defined herein. The substituted 2-phenyl linear alkene benzenes (2-Ph*LAeB) are hydrogenated and sulfonated by well-known methodologies to yield substituted 2-phenyl linear alkylbenzene sulfonates (2-Ph*LAS). 2-Phenyl linear alkylbenzene sulfonates (2-PhLAS) and substituted 2-phenyl linear alkylbenzene sulfonates (2-Ph*LAS) are high-efficiency surfactants useful in hand soaps, dish soaps, hard surface cleaners, laundry detergents, and in cleaning supplies.

BACKGROUND

Global demand for linear alkylbenzene sulfonates (LAS) is 6.7 billion lb/yr ("The Future of LAB" Amandeep Singh, *Inform Magazine* AOCS, March 2012) with 2.7% demand growth. Alkylbenzene sulfonates, especially those made from linear alkylbenzenes (LAB), are primary surfactants used in household cleaners and detergents. The demand for linear alkyl benzene sulfonates continues to grow because of their low cost, strong performance, and biodegradability.

A limitation to increased use of LAS surfactants and related linear surfactants has been because they have poor solubility in cold water and hard water conditions (US 2012/0213726 and WO 2012/138423). This is supported by J. Scheibel in *Journal of Surfactants and Detergents*, (2004) 7, 319, which reported the 4-, 5-, and 6-PhLAS isomers are sensitive to calcium, which form aggregates and are less surface active than the 2-PhLAS and 3-PhLAS isomers. Also J. Scheibel reported that the 2-PhLAS surface activity (critical micelle concentration (CMC)) was 600 ppm while 3-PhLAS CMC was 700 ppm, under the same conditions. Therefore, it takes 15% less of the 2-PhLAS isomer to form a micelle compared to the 3-PhLAS isomer. This aligns well with the publicly communicated "green" initiatives of major detergent companies such as Proctor & Gamble, which by 2020 seeks a 20% reduction in packaging compared to 2010 levels, and a 20% reduction in truck transportation compared to 2010 levels (http://www.pg.com/en_US/sustainability/environmental_sustainability/environmental_vision-.shtml as accessed on Apr. 9, 2013).

One of the "holy grails" of the detergent industry is more concentrated cleaning power. Many industrial experts have described the superior cleaning performance of the 2-PhLAS isomer over the other LAS isomers (e.g., the 1-, 3-, 4-, 5- and 6-PhLAS). U.S. Pat. No. 6,887,839 describes high 2-PhLAS mixtures are more effective cleaning agents over their counterparts with lower 2-PhLAS isomeric content, this is attributed to an unexpected increase in tolerance of water hardness minerals usually associated with precipitation of the active detergent agent. Further fine-tuning of cleaning performance of 2-PhLAS-based agents may be achieved by substitution of additional functional groups on the aromatic ring. For example, 2-tolyl linear alkylbenzene sulfonates have been reported to have lower Krafft temperatures and superior hard water tolerance compared to commercial linear alkylbenzene sulfonate materials (U.S. Pat. No. 6,995, 127).

There are two currently used commercial production processes for LAS. The first, the HF alkylation of detergent (C$_{10}$-C$_{13}$) olefins, gives 18% of the 2-PhLAB isomer while the second, the Detal™ process (licensed by UOP), uses a zeolite catalyst to alkylate detergent olefins and produces 25-35% of 2-PhLAB (Zoller, U. "Handbook of Detergents: Part F Production," v. 142, CRC Press, Boca Raton, Fla., 2009, p 111). It is estimated that ~80% of current manufacturers use the HF process, but new capacity is typically based upon the Detal™ process which also enjoys lower capital costs. It is important to point out that both the HF and Detal™ processes have little control over the formation of the 2-PhLAB isomer as these processes are Friedel-Craft type alkylation of the aromatic ring with an olefin. Under these conditions the double bond of the olefin is isomerized (i.e. migrated along its backbone) resulting in positional-isomeric mixtures of PhLAB. (e.g. 1-PhLAB, 2-PhLAB, 3-PhLAB, 4-PhLAB, 5-PhLAB, 6-PhLAB, etc.).

Over the years efforts have been made to increase the concentration of 2-PhLAS isomer content over other LAS isomers. For example, U.S. Pat. No. 6,562,776 describes a mixture of salts of alkylbenzene sulfonates, prepared by the HF process, wherein the 2-phenyl isomer content of such alkylbenzene sulfonate salts is 42%-82% by weight based on the total weight of LAS isomers.

U.S. Pat. No. 6,887,839 is incorporated by reference and describes high content 2-phenyl linear alkyl benzene sulfonates having enhanced hard water tolerance. This patent does not produce 2-phenyl linear alkylbenzene sulfonates in >85% isomeric purity and does not describe olefin metathesis to produce 2-phenyl linear alkylbenzene sulfonates.

U.S. Pat. App. Pub. No 2012/0213726 is incorporated by reference and describes bio-based linear alkyl phenyl sulfonates (linear alkylbenzene sulfonates) incorporating $C_{10}$-$C_{14}$ olefins which at least 50% bio-based. The bio-based $C_{10}$-$C_{14}$ olefins may be produced by metathesis of seed oils as described in U.S. Pat. App. Pub. No US2010/0145086. U.S. Pat. App. Pub. No. 2012/0213726 does not describe olefin metathesis of alpha-methyl styrene or 3-phenyl-1-butene to produce linear alkyl phenyl sulfonates (linear alkylbenzene sulfonates).

WO Pat. App. Pub. No. 2012/138423 is incorporated by reference and describes $C_{10}$-$C_{13}$ linear alkyl phenyl sulfonates (linear alkylbenzene sulfonates) having a particular alkyl group distribution. This application describes using a particular $C_{10}$-$C_{13}$ olefin distribution to produce $C_{10}$-$C_{13}$ linear alkyl phenyl sulfonates (linear alkylbenzene sulfonates). It does not describe olefin metathesis of alpha-methyl styrene or 3-phenyl-1-butene to produce linear alkyl phenyl sulfonates (linear alkylbenzene sulfonates).

U.S. Pat. App. Pub. No. 2010/0145086 is incorporated by reference and is the seminal patent application describing the production of alpha olefins from alkenolysis of seed oils. It does not describe olefin metathesis of alpha-methyl styrene or 3-phenyl-1-butene to produce linear alkyl benzenes, linear 2-phenylalkylbenzenes, linear alkyl phenyl sulfonates, or linear alkylbenzene sulfonates.

U.S. Pat. No. 6,995,127 is incorporated by reference and describes relatively high content 2-tolyl linear alkyl benzene sulfonates having enhanced hard water tolerance. This patent does not produce 2-phenyl linear alkylbenzene sulfonates in >85% isomeric purity and does not describe olefin metathesis to produce 2-phenyl linear alkylbenzene sulfonates. Under the HF and Detal™ processes utilized, the resulting 2-tolyl linear alkyl benzene sulfonates predominantly comprise para-tolyl groups due to the ortho/para directing effects of methyl(alkyl) groups (combined with steric effects which disfavor ortho-substitution). Similarly, electron-withdrawing groups (i.e. $NO_2$, CN, etc.) would yield predominantly meta-substituted isomers. In contrast, the methods described herein would allow for controlled substitution at any particular position of the aromatic ring or any desired combination of these positions. For example, commercially available tolylstyrenes are available as a mixture of approximately 60% meta- and 40% para-methyl substitution, which will produce a 2-tolyl linear alkylbenzene sulfonate with the same 60% meta- and 40% para-methyl substitution, or in a nearly pure para-methyl form.

Therefore, despite advances achieved in the art, a continuing need exists for further improvement in a number of areas, including methods for the production of alkylbenzenes and alkylbenzene sulfonates having improved selectivity of 2-phenyl linear alkylbenzene isomer production as well as compositions comprising improved 2-phenyl linear alkylbenzene isomer content. In addition, despite advances achieved in the art, a continuing need exists for further improvement in a number of areas, including methods for the production of substituted alkylbenzenes and substituted alkylbenzene sulfonates having improved selectivity of substituted 2-phenyl linear alkylbenzene isomer production as well as compositions comprising improved substituted 2-phenyl linear alkylbenzene isomer content, where the benzene ring is substituted with one or more groups designated R*, where R* is defined herein.

SUMMARY OF INVENTION

The present invention relates to compositions comprising alkene benzenes, compositions comprising alkene benzene sulfonates, methods for making alkene benzenes, methods for making alkene benzene sulfonates, compositions comprising alkylbenzenes, compositions comprising alkylbenzene sulfonates, methods for making alkylbenzenes, and methods for making alkylbenzene sulfonates. More particularly, the present invention relates to compositions comprising 2-phenyl linear alkene benzenes, compositions comprising 2-phenyl linear alkene benzene sulfonates, compositions comprising 2-phenyl linear alkylbenzenes, and compositions comprising 2-phenyl linear alkylbenzene sulfonates, methods for making 2-phenyl alkene benzenes, methods for making 2-phenyl alkene benzene sulfonates, methods for making 2-phenyl alkylbenzenes, and methods for making 2-phenyl alkylbenzene sulfonates.

The present invention also relates to compositions comprising substituted alkene benzenes, compositions comprising substituted alkene benzene sulfonates, methods for making substituted alkene benzenes, methods for making substituted alkene benzene sulfonates, compositions comprising substituted alkylbenzenes, compositions comprising substituted alkylbenzene sulfonates, methods for making substituted alkylbenzenes, and methods for making substituted alkylbenzene sulfonates, where the benzene ring is substituted with one or more groups designated R*, where R* is defined herein. More particularly, the present invention relates to compositions comprising substituted 2-phenyl linear alkene benzenes, compositions comprising substituted 2-phenyl linear alkene benzene sulfonates, compositions comprising substituted 2-phenyl linear alkylbenzenes, and compositions comprising substituted 2-phenyl linear alkylbenzene sulfonates, methods for making substituted 2-phenyl alkene benzenes, methods for making substituted 2-phenyl alkene benzene sulfonates, methods for making substituted 2-phenyl alkylbenzenes, and methods for making substituted 2-phenyl alkylbenzene sulfonates, where the benzene ring is substituted with one or more groups designated R*, where R* is defined herein.

It is an object of the present invention to provide methods for making 2-phenyl linear alkylbenzene sulfonates, which overcome the disadvantages of the prior art. In particular, it is an object of the present invention to provide methods for the production of 2-phenyl linear alkylbenzene sulfonates having improved selectivity of 2-phenyl isomer production. Furthermore, it is an object of the present invention to provide linear alkylbenzene sulfonate compositions comprising increased 2-phenyl linear alkylbenzene sulfonate content compared to prior art compositions.

These objects are solved by the cross metathesis of at least one cross metathesis substrate, with at least one olefinic substrate, in the presence of at least one olefin metathesis catalyst to provide 2-phenyl linear alkene benzenes, which are hydrogenated and sulfonated to give 2-phenyl linear alkylbenzenes sulfonates.

It is an object of the present invention to provide methods for making substituted 2-phenyl linear alkylbenzene sulfonates, which overcome the disadvantages of the prior art, where the benzene ring of the substituted 2-phenyl linear alkylbenzene sulfonates is substituted with one or more groups designated R*, where R* is defined herein. In particular, it is an object of the present invention to provide methods for the production of substituted 2-phenyl linear alkylbenzene sulfonates having improved selectivity of 2-phenyl isomer production, where the benzene ring of the substituted 2-phenyl linear alkylbenzene sulfonates is substituted with one or more groups designated R*, where R* is defined herein. Furthermore, it is an object of the present invention to provide substituted linear alkylbenzene sulfonate compositions comprising increased substituted 2-phenyl linear alkylbenzene sulfonate content compared to prior art compositions, where the benzene ring of the substituted linear alkylbenzene sulfonate compositions is substituted with one or more groups designated R*, where R* is defined herein.

These objects are solved by the cross metathesis of at least one cross metathesis substrate, with at least one olefinic substrate, in the presence of at least one olefin metathesis catalyst to provide substituted 2-phenyl linear alkene benzenes, which are hydrogenated and sulfonated to give substituted 2-phenyl linear alkylbenzenes sulfonates, where the benzene ring of the 2-phenyl linear alkylbenzenes sulfonates is substituted with one or more groups designated R*, where R* is defined herein.

In one embodiment the present invention provides a linear alkylbenzene sulfonate composition, where the 2-phenyl isomer content is at least 85% by weight based on the total weight of linear alkyl benzene sulfonate isomers.

In another embodiment the present invention provides a substituted linear alkylbenzene sulfonate composition, where the substituted 2-phenyl isomer content is at least 85% by weight based on the total weight of substituted linear alkyl benzene sulfonate isomers, where the benzene ring of the substituted linear alkylbenzene sulfonate is substituted with one or more groups designated R*, where R* is defined herein.

In another embodiment the present invention provides a linear alkylbenzene composition, where the 2-phenyl isomer content is at least 85% by weight based on the total weight of linear alkylbenzene isomers.

In another embodiment the present invention provides a substituted linear alkylbenzene composition, where the substituted 2-phenyl isomer content is at least 85% by weight based on the total weight of substituted linear alkylbenzene isomers, where the benzene ring of the substituted linear alkylbenzene is substituted with one or more groups designated R*, where R* is defined herein.

In another embodiment the present invention provides a linear alkylbenzene composition, where the 2-phenyl isomer content is at least 85% by weight based on the total weight of linear alkylbenzene isomers described in the general formula:

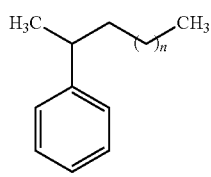

wherein n is equal to any integer between 2 and 18.

In another embodiment the present invention provides a substituted linear alkylbenzene composition, where the substituted 2-phenyl isomer content is at least 85% by weight based on the total weight of linear alkylbenzene isomers described in the general formula:

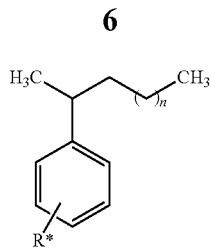

wherein n is equal to any integer between 2 and 18, where the benzene ring of the substituted linear alkylbenzene is substituted with one or more groups designated R*, where R* is defined herein.

In another embodiment of the present invention provides a salt of an alkylbenzene sulfonate, which salt comprises an amount of the 2-phenyl alkylbenzene isomer of alkylbenzenes described by the general formula:

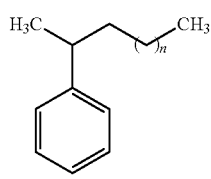

wherein n is equal to any integer between 2 and 18, wherein an amount of 2-phenyl alkylbenzene isomer in such alkylbenzene sulfonate salts is greater than 85% by weight based on the total weight of the alkylbenzene sulfonates, where the 2-phenyl alkylbenzene isomer is prepared by forming a first composition comprising styrene, at least one hydrovinylation catalyst, and ethylene, subjecting the first composition to conditions effective to promote a hydrovinylation reaction to form 3-phenyl-1-butene, forming a second composition comprising 3-phenyl-1-butene, at least one olefinic substrate, and at least one olefin metathesis catalyst, wherein the at least one olefinic substrate is selected from a linear alpha olefin, or a linear internal olefin, or a combination thereof, subjecting the second composition to conditions effective to promote a cross metathesis reaction to form at least one 2-phenyl linear alkene benzene, subjecting the at least one 2-phenyl linear alkene benzene to conditions effective to promote olefin hydrogenation to form at least one 2-phenyl linear alkylbenzene, subjecting the at least one 2-phenyl linear alkylbenzene to conditions effective to promote aromatic sulfonation of the at least one 2-phenyl linear alkylbenzene.

In another embodiment of the present invention provides a salt of an alkylbenzene sulfonate, which the salt comprises an amount of the substituted 2-phenyl alkylbenzene isomer of alkylbenzenes described by the general formula:

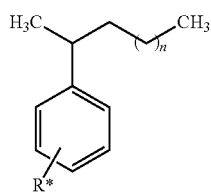

wherein n is equal to any integer between 2 and 18, wherein R* is defined herein, wherein an amount of substituted 2-phenyl alkylbenzene isomer in such alkylbenzene sulfonate salts is greater than 85% by weight based on the total weight of the alkylbenzene sulfonates, where the substituted 2-phenyl alkylbenzene isomer is prepared by forming a first composition comprising a substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form substituted 3-phenyl-1-butene, where the benzene ring of the substituted 3-phenyl-1-butene is substituted with one or more groups designated R*, where R* is defined herein; forming a second composition comprising substituted 3-phenyl-1-butene, at least one olefinic substrate, and at least one olefin metathesis catalyst, wherein the at least one olefinic substrate is selected from a linear alpha olefin, or a linear internal olefin, or a combination thereof, where the benzene ring of the substituted 3-phenyl-1-butene is substituted with one or more groups designated R*, where R* is defined herein; subjecting the second composition to conditions effective to promote a cross metathesis reaction to form at least one substituted 2-phenyl linear alkene benzene, where the benzene ring of the substituted 2-phenyl linear alkene benzene is substituted with one or more groups designated R*, where R* is defined herein; subjecting at least one substituted 2-phenyl linear alkene benzene to conditions effective to promote olefin hydrogenation to form at least one substituted 2-phenyl linear alkylbenzene, where the benzene ring of the substituted 2-phenyl linear alkylbenzene is substituted with one or more groups designated R*, where R* is defined herein; and subjecting at least one substituted 2-phenyl linear alkylbenzene to conditions effective to promote aromatic sulfonation of at least one substituted 2-phenyl linear alkylbenzene.

In another embodiment of the present invention provides a salt of an alkylbenzene sulfonate, which salt comprises an amount of the 2-phenyl alkylbenzene isomer of alkylbenzenes described by the general formula:

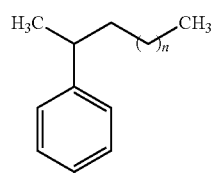

wherein n is equal to any integer between 2 and 18, wherein an amount of 2-phenyl alkylbenzene isomer in such alkylbenzene sulfonate salts is greater than 85% by weight based on the total weight of the alkylbenzene sulfonates, where the 2-phenyl alkylbenzene isomer is prepared by forming a composition comprising alpha-methyl styrene, at least one olefinic substrate, and at least one olefin metathesis catalyst, wherein the at least one olefinic substrate is selected from a linear alpha olefin, or a linear internal olefin, or a combination thereof, subjecting the composition to conditions effective to promote a cross metathesis reaction to form at least one 2-phenyl linear alkene benzene, subjecting the at least one 2-phenyl linear alkene benzene to conditions effective to promote olefin hydrogenation to form at least one 2-phenyl linear alkylbenzene, subjecting the at least one 2-phenyl linear alkylbenzene to conditions effective to promote aromatic sulfonation of the at least one 2-phenyl linear alkylbenzene.

In another embodiment of the present invention provides a salt of an alkylbenzene sulfonate, which salt comprises an amount of the substituted 2-phenyl alkylbenzene isomer of alkylbenzenes described by the general formula:

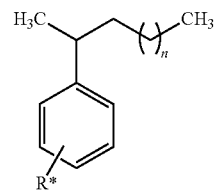

wherein n is equal to any integer between 2 and 18, wherein R* is defined herein, wherein an amount of substituted 2-phenyl alkylbenzene isomer in such alkylbenzene sulfonate salts is greater than 85% by weight based on the total weight of the alkylbenzene sulfonates, where the substituted 2-phenyl alkylbenzene isomer is prepared by forming a composition comprising substituted alpha-methyl styrene, at least one olefinic substrate, and at least one olefin metathesis catalyst, wherein at least one olefinic substrate is selected from a linear alpha olefin, or a linear internal olefin, or a combination thereof, where the benzene ring of the substituted alpha-methyl styrene is substituted with one or more groups designated R*, where R* is defined herein; subjecting the composition to conditions effective to promote a cross metathesis reaction to form at least one substituted 2-phenyl linear alkene benzene, where the benzene ring of the substituted 2-phenyl linear alkene benzene is substituted with one or more groups designated R*, where R* is defined herein; subjecting the at least one substituted 2-phenyl linear alkene benzene to conditions effective to promote olefin hydrogenation to form at least one substituted 2-phenyl linear alkylbenzene, where the benzene ring of the substituted 2-phenyl linear alkylbenzene is substituted with one or more groups designated R*, where R* is defined herein; subjecting at least one substituted 2-phenyl linear alkylbenzene to conditions effective to promote aromatic sulfonation of at least one substituted 2-phenyl linear alkylbenzene.

In another embodiment of the present invention provides a salt of an alkylbenzene sulfonate, which salt comprises an amount of the 2-phenyl isomer of alkylbenzenes described by the general formula:

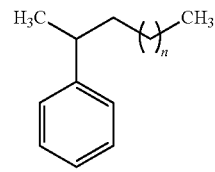

wherein n is equal to any integer between 2 and 18, wherein the amount of 2-phenyl isomer in such alkylbenzene sulfonate salts is greater than 85% by weight based on the total weight of the alkylbenzene sulfonates.

In another embodiment of the present invention provides a salt of an alkylbenzene sulfonate, which salt comprises an amount of the substituted 2-phenyl isomer of alkylbenzenes described by the general formula:

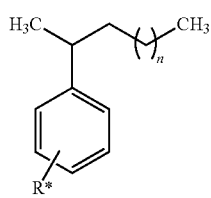

wherein n is equal to any integer between 2 and 18, wherein R* is defined herein, wherein the amount of substituted 2-phenyl isomer in such alkylbenzene sulfonate salts is greater than 85% by weight based on the total weight of the alkylbenzene sulfonates.

In another embodiment the present invention provides a method of making 2-phenyl alkene benzenes, the method comprising forming a composition comprising at least one cross metathesis substrate, at least one olefinic substrate, and at least one olefin metathesis catalyst, and subjecting the composition to conditions effective to promote a cross metathesis reaction between the at least one cross metathesis substrate and at least one olefinic substrate.

In another embodiment the present invention provides a method of making substituted 2-phenyl alkene benzenes, where the benzene ring of the substituted 2-phenyl alkene benzenes is substituted with one or more groups designated R*, where R* is defined herein, the method comprising forming a composition comprising at least one cross metathesis substrate, at least one olefinic substrate, and at least one olefin metathesis catalyst, and subjecting the composition to conditions effective to promote a cross metathesis reaction between the at least one cross metathesis substrate and at least one olefinic substrate.

In another embodiment the present invention provides a method of making 2-phenyl linear alkene benzenes, the method comprising forming a composition comprising at least one cross metathesis substrate, at least one olefinic substrate, and at least one olefin metathesis catalyst, wherein the at least one olefinic substrate is selected from at least one linear alpha olefin, at least one linear internal olefin, or a combination thereof, and subjecting the composition to conditions effective to promote a cross metathesis reaction between the at least one cross metathesis substrate and at least one olefinic substrate.

In another embodiment the present invention provides a method of making substituted 2-phenyl linear alkene benzenes, where the benzene ring of the substituted 2-phenyl linear alkene benzenes is substituted with one or more groups designated R*, where R* is defined herein, the method comprising forming a composition comprising at least one cross metathesis substrate, at least one olefinic substrate, and at least one olefin metathesis catalyst, wherein at least one olefinic substrate is selected from at least one linear alpha olefin, at least one linear internal olefin, or a combination thereof, and subjecting the composition to conditions effective to promote a cross metathesis reaction between at least one cross metathesis substrate and at least one olefinic substrate.

In another embodiment the present invention provides a method of making alkene benzenes, the method comprising forming a composition comprising at least one cross metathesis substrate, at least one olefinic substrate, and at least one olefin metathesis catalyst, and subjecting the composition to conditions effective to promote a cross metathesis reaction to form cross metathesis products, where the cross metathesis products comprise at least one alkene benzene.

In another embodiment the present invention provides a method of making substituted alkene benzenes, where the benzene ring of the substituted alkene benzenes is substituted with one or more groups designated R*, where R* is defined herein, the method comprising forming a composition comprising at least one cross metathesis substrate, at least one olefinic substrate, and at least one olefin metathesis catalyst, and subjecting the composition to conditions effective to promote a cross metathesis reaction to form cross metathesis products, where the cross metathesis products comprise at least one substituted alkene benzene.

In another embodiment the present invention provides a method of making alkyl benzenes, the method comprising forming a composition comprising at least one cross metathesis substrate, at least one olefinic substrate, and at least one olefin metathesis catalyst, and subjecting the composition to conditions effective to promote a cross metathesis reaction to form cross metathesis products where the cross metathesis products comprise at least one alkene benzene, and subjecting the at least one alkene benzene to conditions effective to promote olefinic hydrogenation.

In another embodiment the present invention provides a method of making substituted alkyl benzenes, where the benzene ring of the substituted alkyl benzenes is substituted with one or more groups designated R*, where R* is defined herein, the method comprising forming a composition comprising at least one cross metathesis substrate, at least one olefinic substrate, and at least one olefin metathesis catalyst; subjecting the composition to conditions effective to promote a cross metathesis reaction to form cross metathesis products where the cross metathesis products comprise at least one substituted alkene benzene, where the substituted alkene benzene is substituted with one or more groups designated R*, where R* is defined herein; and subjecting at least one substituted alkene benzene to conditions effective to promote olefinic hydrogenation.

In another embodiment the present invention provides a method of making alkylbenzene sulfonates, the method comprising forming a composition comprising at least one cross metathesis substrate, at least one olefinic substrate, and at least one olefin metathesis catalyst, and subjecting the composition to conditions effective to promote a cross metathesis reaction to form cross metathesis products where the cross metathesis products comprise at least one alkene benzene, and subjecting the at least one alkene benzene to conditions effective to promote olefinic hydrogenation to form hydrogenation products where the hydrogenation products comprise at least one alkylbenzene, and subjecting the at least one alkylbenzene to conditions effective to promote aromatic sulfonation.

In another embodiment the present invention provides a method of making substituted alkylbenzene sulfonates, where the benzene ring of the substituted alkylbenzene sulfonates is substituted with one or more groups designated R*, where R* is defined herein, the method comprising forming a composition comprising at least one cross metathesis substrate, at least one olefinic substrate, and at least one olefin metathesis catalyst; subjecting the composition to conditions effective to promote a cross metathesis reaction to form cross metathesis products where the cross metathesis products comprise at least one substituted alkene benzene, where the benzene ring of the substituted alkene benzene is substituted with one or more groups designated R*, where R* is defined herein; and subjecting at least one substituted alkene benzene to conditions effective to promote olefinic hydrogenation to form hydrogenation products where the hydrogenation products comprise at least one substituted alkylbenzene, where the benzene ring of the substituted alkylbenzene is substituted with one or more groups designated R*, where R* is defined herein; and subjecting at least one substituted alkylbenzene to conditions effective to promote aromatic sulfonation.

In another embodiment the present invention provides a method of making 2-phenyl linear alkene benzenes, the method comprising forming a composition comprising at least one cross metathesis substrate, at least one olefinic substrate, and at least one olefin metathesis catalyst, wherein the at least one olefinic substrate is selected from at least one linear alpha olefin, at least one linear internal olefin, or a combination thereof, subjecting the composition to conditions effective to promote a cross metathesis reaction to form cross metathesis products, where the cross metathesis products comprise at least one 2-phenyl linear alkene benzene, and separating at least a portion of the at least one 2-phenyl linear alkene benzene from the cross metathesis products.

In another embodiment the present invention provides a method of making substituted 2-phenyl linear alkene benzenes, where the benzene ring of the substituted 2-phenyl linear alkene benzenes is substituted with one or more groups designated R*, where R* is defined herein, the method comprising forming a composition comprising at least one cross metathesis substrate, at least one olefinic substrate, and at least one olefin metathesis catalyst, wherein at least one olefinic substrate is selected from at least one linear alpha olefin, at least one linear internal olefin, or a combination thereof; subjecting the composition to conditions effective to promote a cross metathesis reaction to form cross metathesis products, where the cross metathesis products comprise at least one substituted 2-phenyl linear alkene benzene, where the benzene ring of the substituted 2-phenyl linear alkene benzenes is substituted with one or more groups designated R*, where R* is defined herein; and separating at least a portion of at least one substituted 2-phenyl linear alkene benzene from the cross metathesis products.

In another embodiment the present invention provides a method of making 2-phenyl linear alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one olefinic substrate, and at least one olefin metathesis catalyst, where the at least one olefinic substrate is selected from at least one linear alpha olefin, at least one linear internal olefin, or a combination thereof, and subjecting the second composition to conditions effective to promote a cross metathesis reaction between 3-phenyl-1-butene and the at least one olefinic substrate.

In another embodiment the present invention provides a method of making substituted 2-phenyl linear alkene benzenes, where the benzene ring is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the substituted 3-phenyl-1-butene is substituted with one or more groups designated R*, where R* is defined herein; forming a second composition comprising the hydrovinylation products comprising substituted 3-phenyl-1-butene, at least one olefinic substrate, and at least one olefin metathesis catalyst, where at least one olefinic substrate is selected from at least one linear alpha olefin, at least one linear internal olefin, or a combination thereof, and subjecting the second composition to conditions effective to promote a cross metathesis reaction between substituted 3-phenyl-1-butene and the at least one olefinic substrate.

In another embodiment the present invention provides a method of making 2-phenyl linear alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between 3-phenyl-1-butene and at least one olefinic substrate, and separating at least a portion of the at least one 2-phenyl linear alkene benzene from the cross metathesis products.

In another embodiment the present invention provides a method of making substituted 2-phenyl linear alkene benzenes, where the benzene ring of the substituted 2-phenyl linear alkene benzenes is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the 3-phenyl-1-butene is substituted with one or more groups designated R*, where R* is defined herein; forming a second composition comprising the hydrovinylation products comprising substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where the at least one substituted 2-phenyl linear alkene benzene is derived from a cross metathesis reaction between substituted 3-phenyl-1-butene and at least one olefinic substrate, where the benzene ring of the substituted 2-phenyl linear alkene benzene is substituted with one or more groups designated R*, where R* is defined herein; and separating at least a portion of the at least one substituted 2-phenyl linear alkene benzene from the cross metathesis products.

In another embodiment the present invention provides a method of making 2-phenyl linear alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, separating at least a portion of the 3-phenyl-1-butene from the hydrovinylation products, forming a second composition comprising the separated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction between 3-phenyl-1-butene and at least one olefinic substrate.

In another embodiment the present invention provides a method of making substituted 2-phenyl linear alkene benzenes, where the benzene ring of the substituted 2-phenyl linear alkene benzenes is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the 3-phenyl-1-butene is substituted with one or more groups designated R*, where R* is defined herein; separating at least a portion of the substituted 3-phenyl-1-butene from the hydrovinylation products, forming a second composition comprising the separated substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction between substituted 3-phenyl-1-butene and at least one olefinic substrate.

In another embodiment the present invention provides a method of making 2-phenyl linear alkene benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, separating at least a portion of the 3-phenyl-1-butene from the hydrovinylation products, forming a second composition comprising the separated 3-phenyl-1-butene, at least one olefinic substrate, and at least one olefin metathesis catalyst, where the at least one olefin metathesis substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between 3-phenyl-1-butene and at least one olefinic substrate, and separating at least a portion of the at least one 2-phenyl linear alkene benzene from the cross metathesis products.

In another embodiment the present invention provides a method of making substituted 2-phenyl linear alkene benzenes, where the benzene ring of the 2-phenyl linear alkene benzenes is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the substituted 3-phenyl-1-butene is substituted with one or more groups designated R*, where R* is defined herein; separating at least a portion of the substituted 3-phenyl-1-butene from the hydrovinylation products, forming a second composition comprising the separated substituted 3-phenyl-1-butene, at least one olefinic substrate, and at least one olefin metathesis catalyst, where at least one olefin metathesis substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from a cross metathesis reaction between substituted 3-phenyl-1-butene and at least one olefinic substrate, where the benzene ring of the 2-phenyl linear alkene benzene is substituted with one or more groups designated R*, where R* is defined herein; and separating at least a portion of the at least one substituted 2-phenyl linear alkene benzene from the cross metathesis products.

In another embodiment the present invention provides a method of making 2-phenyl linear alkyl benzenes, the method comprising forming a first composition comprising alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the first composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between alpha-methyl styrene and at least one olefinic substrate, and subjecting the cross metathesis products comprising at least one 2-phenyl linear alkene benzene to conditions effective to promote olefin hydrogenation.

In another embodiment the present invention provides a method of making substituted 2-phenyl linear alkyl benzenes, where the benzene ring of the 2-phenyl linear alkyl benzenes is substituted with one or more groups designated R*, where R* is defined herein, the method comprising forming a first composition comprising substituted alpha-methyl styrene, at least one olefinic substrate, and at least one olefin metathesis catalyst, where at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the first composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from a cross metathesis reaction between substituted alpha-methyl styrene and at least one olefinic substrate, where the benzene ring of the substituted 2-phenyl linear alkene benzene is substituted with one or more groups designated R*, where R* is defined herein; and subjecting the cross metathesis products comprising at least one substituted 2-phenyl linear alkene benzene to conditions effective to promote olefin hydrogenation.

In another embodiment the present invention provides a method of making 2-phenyl linear alkyl benzenes, the method comprising forming a first composition comprising alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the first combination to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between alpha-methyl styrene and at least one olefinic substrate, separating at least a portion of the at least one 2-phenyl linear alkene benzene from the cross metathesis products, subjecting the separated at least one 2-phenyl linear alkene benzene to condition effective to promote olefin hydrogenation.

In another embodiment the present invention provides a method of making substituted 2-phenyl linear alkyl benzenes, where the benzene ring of the 2-phenyl linear alkyl benzenes is substituted with one or more groups designated R*, where R* is defined herein, the method comprising forming a first composition comprising substituted alpha-methyl styrene, at least one olefinic substrate, and at least one olefin metathesis catalyst, where at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the first combination to conditions effective to promote a cross metathesis reaction to form cross metathesis products, where the cross metathesis products comprise at least one substituted 2-phenyl linear alkene benzene, where at least one substituted 2-phenyl linear alkene benzene is derived from a cross metathesis reaction between substituted alpha-methyl styrene and at least one olefinic substrate, where the benzene ring of the substituted 2-phenyl linear alkene benzene is substituted with one or more groups designated R*, where R* is defined herein; separating at least a portion of the at least one substituted 2-phenyl linear alkene benzene from the cross metathesis products, subjecting the separated at least one substituted 2-phenyl linear alkene benzene to condition effective to promote olefin hydrogenation.

In another embodiment the present invention provides a method of making 2-phenyl linear alkyl benzenes, the method comprising forming a first composition comprising alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the first combination to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between alpha-methyl styrene and at least one olefinic substrate, separating at least a portion of the at least one 2-phenyl linear alkene benzene from the cross metathesis products; subjecting the separated at least one 2-phenyl linear alkene benzene to conditions effective to promote olefin hydrogenation to form hydrogenation products comprising at least one 2-phenyl linear alkyl benzene; and separating at least a portion of the 2-phenyl linear alkyl benzene from the hydrogenation products.

In another embodiment the present invention provides a method of making substituted 2-phenyl linear alkyl benzenes, where the benzene ring of the substituted 2-phenyl linear alkyl benzenes is substituted with one or more groups designated R*, where R* is defined herein, the method comprising forming a first composition comprising substituted alpha-methyl styrene, at least one olefinic substrate, and at least one olefin metathesis catalyst, where at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the first combination to conditions effective to promote a cross metathesis reaction to form cross metathesis products, where the cross metathesis products comprise at least one substituted 2-phenyl linear alkene benzene, where at least one substituted 2-phenyl linear alkene benzene is derived from a cross metathesis reaction between substituted alpha-methyl styrene and at least one olefinic substrate, where the benzene ring of the substituted 2-phenyl linear alkene benzene is substituted with one or more groups designated R*, where R* is defined herein; separating at least a portion of the at least one substituted 2-phenyl linear alkene benzene from the cross metathesis products; subjecting the separated at least one substituted 2-phenyl linear alkene benzene to conditions effective to promote olefin hydrogenation to form hydrogenation products comprising at least one substituted 2-phenyl linear alkyl benzene, where the benzene ring of the 2-phenyl linear alkyl benzene is substituted with one or more groups designated R*, where R* is defined herein, and separating at least a portion of the substituted 2-phenyl linear alkyl benzene from the hydrogenation products.

In another embodiment the present invention provides a method of making 2-phenyl linear alkyl benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between 3-phenyl-1-butene and at least one olefinic substrate, and subjecting the cross metathesis products comprising at least one 2-phenyl linear alkene benzene to conditions effective to promote olefin hydrogenation.

In another embodiment the present invention provides a method of making substituted 2-phenyl linear alkyl benzenes, where the benzene ring of the substituted 2-phenyl linear alkyl benzenes is substituted with one or more groups designated R*, where R* is defined herein, the method comprising forming a first composition comprising substituted styrene, at least one hydrovinylation catalyst, and ethylene, where the benzene ring of the substituted benzene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the substituted 3-phenyl-1-butene is substituted with one or more groups designated R*, where R* is defined herein; forming a second composition comprising the hydrovinylation products comprising substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from a cross metathesis reaction between substituted 3-phenyl-1-butene and at least one olefinic substrate, where the benzene ring of the substituted 2-phenyl linear alkene benzene is substituted with one or more groups designated R*, where R* is defined herein; and subjecting the cross metathesis products comprising at least one substituted 2-phenyl linear alkene benzene to conditions effective to promote olefin hydrogenation.

In another embodiment the present invention provides a method of making 2-phenyl linear alkyl benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, separating at least a portion of the 3-phenyl-1-butene from the hydrovinylation products, forming a second composition comprising the separated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between the separated 3-phenyl-1-butene and at least one olefinic substrate, and subjecting the cross metathesis products comprising at least one 2-phenyl linear alkene benzene to conditions effective to promote olefin hydrogenation.

In another embodiment the present invention provides a method of making substituted 2-phenyl linear alkyl benzenes, where the benzene ring of the substituted 2-phenyl linear alkyl benzenes is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the 3-phenyl-1-butene is substituted with one or more groups designated R*, where R* is defined herein; separating at least a portion of the substituted 3-phenyl-1-butene from the hydrovinylation products, forming a second composition comprising the separated substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where the at least one substituted 2-phenyl linear alkene benzene is derived from a cross metathesis reaction between the separated substituted 3-phenyl-1-butene and at least one olefinic substrate, where the benzene ring of the substituted 2-phenyl linear alkene benzene is substituted with one or more groups designated R*, where R* is defined herein; and subjecting the cross metathesis products comprising at least one substituted 2-phenyl linear alkene benzene to conditions effective to promote olefin hydrogenation.

In another embodiment the present invention provides a method of making substituted 2-phenyl linear alkyl benzenes, where the benzene ring of the substituted 2-phenyl linear alkyl benzenes is substituted with one or more groups designated R*, where R* is defined herein, whereas the substitution pattern of the substituted 2-phenyl linear alkyl benzenes is retained from the substitution pattern of the substituted 3-phenyl-1-butene, where the benzene ring of the substituted 3-phenyl-1-butene is substituted with one or more groups designated R*, where R* is defined herein, whereas the substitution pattern of substituted 3-phenyl-1-butene is that of the starting substituted styrene, where the benzene ring of the substituted styrene is substituted with one or more groups designated R*, where R* is defined herein. For example, commercially available tolylstyrene is a mixture of approximately 60% meta and 40% para methyl substitution, which will produce 3-tolyl-1-butene containing the same 60% meta and 40% para methyl substitution, which will produce 2-tolyl linear alkenylbenzene with the same 60% meta and 40% para methyl substitution, which will produce 2-tolyl linear alkylbenzene with the same 60% meta and 40% para methyl substitution and which will produce 2-tolyl linear alkylbenzene sulfonate with the same 60% meta and 40% para methyl substitution.

In another embodiment the present invention provides a method of making 2-phenyl linear alkyl benzenes, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, separating at least a portion of the 3-phenyl-1-butene from the hydrovinylation products, forming a second composition comprising the separated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from a cross metathesis reaction between the separated 3-phenyl-1-butene and at least one olefinic substrate, and subjecting the cross metathesis products comprising at least one 2-phenyl linear alkene benzene to conditions effective to promote olefin hydrogenation to form hydrogenation products comprising at least one 2-phenyl linear alkyl benzene, and separating at least a portion of the at least one 2-phenyl linear alkyl benzene from the hydrogenation products.

In another embodiment the present invention provides a method of making substituted 2-phenyl linear alkyl benzenes, where the benzene ring of the substituted 2-phenyl linear alkyl benzenes is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the 3-phenyl-1-butene is substituted with one or more groups designated R*, where R* is defined herein; separating at least a portion of the substituted 3-phenyl-1-butene from the hydrovinylation products, forming a second composition comprising the separated substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where the at least one substituted 2-phenyl linear alkene benzene is derived from a cross metathesis reaction between the separated substituted 3-phenyl-1-butene and at least one olefinic substrate, where the benzene ring of the 2-phenyl linear alkene benzene is substituted with one or more groups designated R*, where R* is defined herein; and subjecting the cross metathesis products comprising at least one substituted 2-phenyl linear alkene benzene to conditions effective to promote olefin hydrogenation to form hydrogenation products comprising at least one substituted 2-phenyl linear alkyl benzene, where the benzene ring of the 2-phenyl linear alkyl benzene is substituted with one or more groups designated R*, where R* is defined herein, and separating at least a portion of the at least one substituted 2-phenyl linear alkyl benzene from the hydrogenation products.

In another embodiment the present invention provides a method of making 2-phenyl linear alkyl benzene sulfonates, the method comprising forming a first composition comprising alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the first composition to conditions effective to promote a cross metathesis reaction to form cross metathesis products, where the cross metathesis products comprise at least one 2-phenyl linear alkene benzene, where the at least one 2-phenyl linear alkene benzene is derived from the cross metathesis reaction between alpha-methyl styrene and at least one olefinic substrate, separating at least a portion of the at least one 2-phenyl linear alkene benzene from the cross metathesis products, subjecting the separated at least one 2-phenyl linear alkene benzene to conditions effective to promote olefin hydrogenation to form hydrogenation products comprising at least one 2-phenyl linear alkyl benzene, separating at least a portion of the at least 2-phenyl linear alkyl benzene from the hydrogenation products, subjecting the separated at least one 2-phenyl linear alkyl benzene to conditions effective to promote aromatic sulfonation of the at least one 2-phenyl linear alkyl benzene to form sulfonation products comprising at least one 2-phenyl linear alkyl benzene sulfonate, and separating at least a portion of the at least one 2-phenyl linear alkyl benzene sulfonate from the sulfonation products.

In another embodiment the present invention provides a method of making substituted 2-phenyl linear alkyl benzene sulfonates, where the benzene ring of the 2-phenyl linear alkyl benzene sulfonates is substituted with one or more groups designated R*, where R* is defined herein, the method comprising forming a first composition comprising substituted alpha-methyl styrene, at least one olefinic substrate, and at least one olefin metathesis catalyst, where at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the first composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from the cross metathesis reaction between substituted alpha-methyl styrene and at least one olefinic substrate, where the benzene ring of the substituted 2-phenyl linear alkene benzene is substituted with one or more groups designated R*, where R* is defined herein; separating at least a portion of the at least one substituted 2-phenyl linear alkene benzene from the cross metathesis products, subjecting the separated at least one substituted 2-phenyl linear alkene benzene to conditions effective to promote olefin hydrogenation to form hydrogenation products comprising at least one substituted 2-phenyl linear alkyl benzene, where the benzene ring of the 2-phenyl linear alkyl benzene is substituted with one or more groups designated R*, where R* is defined herein; separating at least a portion of the at least one substituted 2-phenyl linear alkyl benzene from the hydrogenation products, subjecting the separated at least one substituted 2-phenyl linear alkyl benzene to conditions effective to promote aromatic sulfonation of the at least one substituted 2-phenyl linear alkyl benzene to form sulfonation products comprising at least one substituted 2-phenyl linear alkyl benzene sulfonate, where the benzene ring of the substituted 2-phenyl linear alkyl benzene sulfonate is substituted with one or more groups designated R*, where R* is defined herein; and separating at least a portion of the at least one substituted 2-phenyl linear alkyl benzene sulfonate from the sulfonation products.

In another embodiment the present invention provides a method of making 2-phenyl linear alkyl benzene sulfonates the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, forming a second composition comprising the hydrovinylation products comprising 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from the cross metathesis reaction between the 3-phenyl-1-butene and at least one olefinic substrate, subjecting the cross metathesis products comprising at least one 2-phenyl linear alkene benzene to conditions effective to promote olefin hydrogenation to form hydrogenation products comprising at least one 2-phenyl linear alkylbenzene, subjecting the hydrogenation products comprising at least one 2-phenyl linear alkylbenzene to conditions effective to promote an aromatic sulfonation of the at least one 2-phenyl linear alkylbenzene to form sulfonation products comprising at least one 2-phenyl linear alkylbenzene sulfonate.

In another embodiment the present invention provides a method of making substituted 2-phenyl linear alkyl benzene sulfonates, where the benzene ring of the substituted 2-phenyl linear alkyl benzene sulfonates is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the substituted 3-phenyl-1-butene is substituted with one or more groups designated R*, where R* is defined herein; forming a second composition comprising the hydrovinylation products comprising substituted 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from the cross metathesis reaction between the substituted 3-phenyl-1-butene and at least one olefinic substrate, where the benzene ring of the substituted 2-phenyl linear alkene benzene is substituted with one or more groups designated R*, where R* is defined herein; subjecting the cross metathesis products comprising at least one substituted 2-phenyl linear alkene benzene to conditions effective to promote olefin hydrogenation to form hydrogenation products comprising at least one substituted 2-phenyl linear alkylbenzene, where the benzene ring of the substituted 2-phenyl linear alkylbenzene is substituted with one or more groups designated R*, where R* is defined herein; subjecting the hydrogenation products comprising at least one substituted 2-phenyl linear alkylbenzene to conditions effective to promote an aromatic sulfonation of the at least one substituted 2-phenyl linear alkylbenzene to form sulfonation products comprising at least one substituted 2-phenyl linear alkylbenzene sulfonate, where the benzene ring of the substituted 2-phenyl linear alkyl benzene sulfonate is substituted with one or more groups designated R*, where R* is defined herein.

In another embodiment the present invention provides a method of making 2-phenyl linear alkyl benzene sulfonates, the method comprising forming a first composition comprising styrene, at least one hydrovinylation catalyst, and ethylene, subjecting the first composition to conditions effective to promote a hydrovinylation reaction to form 3-phenyl-1-butene, forming a second composition comprising 3-phenyl-1-butene, at least one olefinic substrate, and at least one olefin metathesis catalyst, wherein the at least one olefinic substrate is selected from a linear alpha olefin, or a linear internal olefin, or a combination thereof, subjecting the second composition to conditions effective to promote a cross metathesis reaction to form at least one 2-phenyl linear alkene benzene, subjecting the at least one 2-phenyl linear alkene benzene to conditions effective to promote olefin hydrogenation to form at least one 2-phenyl linear alkylbenzene, subjecting the at least one 2-phenyl linear alkylbenzene to conditions effective to promote aromatic sulfonation of the at least one 2-phenyl linear alkylbenzene.

In another embodiment the present invention provides a method of making substituted 2-phenyl linear alkyl benzene sulfonates, where the benzene ring of the substituted 2-phenyl linear alkyl benzene sulfonates is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form an substituted 3-phenyl-1-butene, where the benzene ring of the 3-phenyl-1-butene is substituted with one or more groups designated R*, where R* is defined herein; forming a second composition comprising substituted 3-phenyl-1-butene, at least one olefinic substrate, and at least one olefin metathesis catalyst, wherein the at least one olefinic substrate is selected from a linear alpha olefin, or a linear internal olefin, or a combination thereof, subjecting the second composition to conditions effective to promote a cross metathesis reaction to form at least one substituted 2-phenyl linear alkene benzene, where the benzene ring of the substituted 2-phenyl linear alkene benzene is substituted with one or more groups designated R*, where R* is defined herein; subjecting the at least one substituted 2-phenyl linear alkene benzene to conditions effective to promote olefin hydrogenation to form at least one substituted 2-phenyl linear alkylbenzene, where the benzene ring of the substituted 2-phenyl linear alkylbenzene is substituted with one or more groups designated R*, where R* is defined herein; subjecting the at least one substituted 2-phenyl linear alkylbenzene to conditions effective to promote aromatic sulfonation of the at least one substituted 2-phenyl linear alkylbenzene.

In another embodiment the present invention provides a method of making 2-phenyl linear alkyl benzene sulfonates, the method comprising forming a first composition comprising styrene, at least one hydrovinylation catalyst, and ethylene, subjecting the first composition to conditions effective to promote a hydrovinylation reaction to form hydrovinylation products, where the hydrovinylation products comprise 3-phenyl-1-butene, separating at least a portion of the 3-phenyl-1-butene from the hydrovinylation products, forming a second composition comprising the separated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one 2-phenyl linear alkene benzene, where the at least one 2-phenyl linear alkene benzene is derived from the cross metathesis reaction between the separated 3-phenyl-1-butene and at least one olefinic substrate, separating the at least one 2-phenyl linear alkene benzene from the cross metathesis products, subjecting the separated at least one 2-phenyl linear alkene benzene to conditions effective to promote olefin hydrogenation to form hydrogenation products comprising at least one 2-phenyl linear alkylbenzene; separating at least a portion of the at least one 2-phenyl linear alkylbenzene from the hydrogenation products, subjecting the separated at least one 2-phenyl linear alkylbenzene to conditions effective to promote aromatic sulfonation of the at least one 2-phenyl linear alkylbenzene to form sulfonation products comprising at least one 2-phenyl linear alkylbenzene sulfonate, and separating at least a portion of the at least one 2-phenyl linear alkylbenzene sulfonate from the sulfonation products.

In another embodiment the present invention provides a method of making substituted 2-phenyl linear alkyl benzene sulfonates, where the benzene ring of the substituted 2-phenyl linear alkyl benzene sulfonates is substituted with one or more groups designated R*, where R* is defined herein, the method comprising forming a first composition comprising substituted styrene, at least one hydrovinylation catalyst, and ethylene, where the benzene ring of the substituted styrene is substituted with one or more groups designated R*, where R* is defined herein; subjecting the first composition to conditions effective to promote a hydrovinylation reaction to form hydrovinylation products, where the hydrovinylation products comprise substituted 3-phenyl-1-butene, where the benzene ring of the 3-phenyl-1-butene is substituted with one or more groups designated R*, where R* is defined herein; separating at least a portion of the substituted 3-phenyl-1-butene from the hydrovinylation products, forming a second composition comprising the separated substituted 3-phenyl-1-butene, at least one olefinic substrate, and at least one olefin metathesis catalyst, where at least one olefinic substrate is selected from at least one linear alpha olefin, at least one linear internal olefin, or a combination thereof, subjecting the second composition to conditions effective to promote a cross metathesis reaction to form cross metathesis products, where the cross metathesis products comprise at least one substituted 2-phenyl linear alkene benzene, where at least one substituted 2-phenyl linear alkene benzene is derived from the cross metathesis reaction between the separated substituted 3-phenyl-1-butene and at least one olefinic substrate, where the benzene ring of the substituted 2-phenyl linear alkene benzene is substituted with one or more groups designated R*, where R* is defined herein; separating the at least one substituted 2-phenyl linear alkene benzene from the cross metathesis products, subjecting the separated at least one substituted 2-phenyl linear alkene benzene to conditions effective to promote olefin hydrogenation to form hydrogenation products comprising at least one substituted 2-phenyl linear alkylbenzene, where the benzene ring of the 2-phenyl linear alkylbenzene is substituted with one or more groups designated R*, where R* is defined herein; separating at least a portion of the at least one substituted 2-phenyl linear alkylbenzene from the hydrogenation products, subjecting the separated at least one substituted 2-phenyl linear alkylbenzene to conditions effective to promote aromatic sulfonation of the at least one substituted 2-phenyl linear alkylbenzene to form sulfonation products comprising at least one substituted 2-phenyl linear alkylbenzene sulfonate, where the benzene ring of the substituted 2-phenyl linear alkylbenzene sulfonate is substituted with one or more groups designated R*, where R* is defined herein; and separating at least a portion of the at least one substituted 2-phenyl linear alkylbenzene sulfonate from the sulfonation products.

In another embodiment the present invention provides a method of making 2-phenyl alkene benzene sulfonates, the method comprising forming a composition comprising sulfonated alpha-methyl styrene, at least one olefinic substrate, and at least one olefin metathesis catalyst, and subjecting the composition to conditions effective to promote a cross metathesis reaction.

In another embodiment the present invention provides a method of making substituted 2-phenyl alkene benzene sulfonates, where the benzene ring of the substituted 2-phenyl alkene benzene sulfonates is substituted with one or more groups designated R*, where R* is defined herein, the method comprising forming a composition comprising sulfonated substituted alpha-methyl styrene, at least one olefinic substrate, and at least one olefin metathesis catalyst, where the benzene ring of the substituted alpha-methyl styrene is substituted with one or more groups designated R*, where R* is defined herein; and subjecting the composition to conditions effective to promote a cross metathesis reaction.

In another embodiment the present invention provides a method of making 2-phenyl alkene benzene sulfonates, the method comprising forming a composition comprising sulfonated 3-phenyl-1-butene, at least one olefinic substrate, and at least one olefin metathesis catalyst, and subjecting the composition to conditions effective to promote a cross metathesis reaction.

In another embodiment the present invention provides a method of making substituted 2-phenyl alkene benzene sulfonates, where the benzene ring of the substituted 2-phenyl alkene benzene sulfonates is substituted with one or more groups designated R*, where R* is defined herein, the method comprising forming a composition comprising sulfonated substituted 3-phenyl-1-butene, at least one olefinic substrate, and at least one olefin metathesis catalyst, where the benzene ring of the sulfonated substituted 3-phenyl-1-butene is substituted with one or more groups designated R*, where R* is defined herein; and subjecting the composition to conditions effective to promote a cross metathesis reaction.

In another embodiment the present invention provides a method of making 2-phenyl linear alkene benzene sulfonates, the method comprising forming a composition comprising sulfonated alpha-methyl styrene, at least one olefinic substrate, and at least one olefin metathesis catalyst, wherein the at least one olefinic substrate is selected from at least one linear internal olefin, at least one linear alpha olefin, or a combination thereof, and subjecting the composition to conditions effective to promote a cross metathesis reaction.

In another embodiment the present invention provides a method of making substituted 2-phenyl linear alkene benzene sulfonates, where the benzene ring of the substituted 2-phenyl linear alkene benzene sulfonates is substituted with one or more groups designated R*, where R* is defined herein, the method comprising forming a composition comprising sulfonated substituted alpha-methyl styrene, at least one olefinic substrate, and at least one olefin metathesis catalyst, wherein at least one olefinic substrate is selected from at least one linear internal olefin, at least one linear alpha olefin, or a combination thereof, where the benzene ring of the substituted alpha-methyl styrene is substituted with one or more groups designated R*, where R* is defined herein; and subjecting the composition to conditions effective to promote a cross metathesis reaction.

In another embodiment the present invention provides a method of making 2-phenyl linear alkene benzene sulfonates, the method comprising forming a composition comprising sulfonated 3-phenyl-1-butene, at least one olefinic substrate, and at least one olefin metathesis catalyst, wherein the at least one olefinic substrate is selected from at least one linear internal olefin, at least one linear alpha olefin, or a combination thereof, and subjecting the composition to conditions effective to promote a cross metathesis reaction.

In another embodiment the present invention provides a method of making substituted 2-phenyl linear alkene benzene sulfonates, where the benzene ring of the substituted 2-phenyl linear alkene benzene sulfonates is substituted with one or more groups designated R*, where R* is defined herein, the method comprising forming a composition comprising sulfonated substituted 3-phenyl-1-butene, at least one olefinic substrate, and at least one olefin metathesis catalyst, wherein the at least one olefinic substrate is selected from at least one linear internal olefin, at least one linear alpha olefin, or a combination thereof, where the benzene ring of the sulfonated substituted 3-phenyl-1-butene is substituted with one or more groups designated R*, where R* is defined herein; and subjecting the composition to conditions effective to promote a cross metathesis reaction.

In another embodiment the present invention provides a method of making 2-phenyl linear alkene benzene sulfonates, the method comprising forming a composition comprising sulfonated alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction to form cross metathesis products comprising at least one 2-phenyl linear alkene benzene sulfonate, and separating at least a portion of the at least one 2-phenyl linear alkyl benzene sulfonate from the cross metathesis products.

In another embodiment the present invention provides a method of making substituted 2-phenyl linear alkene benzene sulfonates, where the benzene ring of the substituted 2-phenyl linear alkene benzene sulfonates is substituted with one or more groups designated R*, where R* is defined herein, the method comprising forming a composition comprising sulfonated substituted alpha-methyl styrene, at least one olefinic substrate, and at least one olefin metathesis catalyst, where the at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the composition to conditions effective to promote a cross metathesis reaction to form cross metathesis products comprising at least one substituted 2-phenyl linear alkene benzene sulfonate, where the benzene ring of the substituted 2-phenyl linear alkene benzene sulfonate is substituted with one or more groups designated R*, where R* is defined herein; and separating at least a portion of the substituted 2-phenyl linear alkyl benzene sulfonate from the cross metathesis products.

In another embodiment the present invention provides a method of making 2-phenyl linear alkene benzene sulfonates, the method comprising forming a composition comprising sulfonated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction to form cross metathesis products comprising at least one 2-phenyl linear alkene benzene sulfonate, and separating at least a portion of the at least one 2-phenyl linear alkyl benzene sulfonate from the cross metathesis products.

In another embodiment the present invention provides a method of making substituted 2-phenyl linear alkene benzene sulfonates, where the benzene ring of the substituted 2-phenyl linear alkene benzene sulfonates is substituted with one or more groups designated R*, where R* is defined herein, the method comprising forming a composition comprising sulfonated substituted 3-phenyl-1-butene, at least one olefinic substrate, and at least one olefin metathesis catalyst, where the at least one olefinic substrate is selected from at least one linear alpha olefin, at least one linear internal olefin, or a combination thereof, where the benzene ring of the substituted 3-phenyl-1-butene is substituted with one or more groups designated R*, where R* is defined herein, subjecting the composition to conditions effective to promote a cross metathesis reaction to form cross metathesis products comprising at least one substituted 2-phenyl linear alkene benzene sulfonate, where the benzene ring of the substituted 2-phenyl linear alkene benzene sulfonate is substituted with one or more groups designated R*, where R* is defined herein; and separating at least a portion of the substituted 2-phenyl linear alkyl benzene sulfonate from the cross metathesis products.

In another embodiment the present invention provides a method of making 2-phenyl linear alkyl benzene sulfonates, the method comprising forming a composition comprising sulfonated alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction.

In another embodiment the present invention provides a method of making substituted 2-phenyl linear alkyl benzene sulfonates, where the benzene ring of the substituted 2-phenyl linear alkyl benzene sulfonates is substituted with one or more groups designated R*, where R* is defined herein, the method comprising forming a composition comprising sulfonated substituted alpha-methyl styrene, at least one olefinic substrate, and at least one olefin metathesis catalyst, where the at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the composition to conditions effective to promote a cross metathesis reaction.

In another embodiment the present invention provides a method of making 2-phenyl linear alkylbenzene sulfonates, the method comprising forming a composition comprising sulfonated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction.

In another embodiment the present invention provides a method of making substituted 2-phenyl linear alkylbenzene sulfonates, where the benzene ring of the substituted 2-phenyl linear alkylbenzene sulfonates is substituted with one or more groups designated R*, where R* is defined herein, the method comprising forming a composition comprising sulfonated substituted 3-phenyl-1-butene, at least one olefinic substrate, and at least one olefin metathesis catalyst, where the at least one olefinic substrate is selected from at least one linear alpha olefin, at least one linear internal olefin, or a combination thereof, where the benzene ring of the substituted 3-phenyl-1-butene is substituted with one or more groups designated R*, where R* is defined herein, and subjecting the composition to conditions effective to promote a cross metathesis reaction.

In another embodiment the present invention provides a method of making 2-phenyl linear alkylbenzene sulfonates, the method comprising forming a composition comprising sulfonated alpha-methyl styrene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction to form cross metathesis products where the cross metathesis products comprise at least one 2-phenyl linear alkene benzene sulfonate, where the at least one 2-phenyl linear alkene benzene sulfonate is derived from a cross metathesis reaction between alpha-methyl styrene sulfonate and at least one olefinic substrate, and subjecting the cross metathesis products comprising at least one 2-phenyl linear alkene benzene sulfonate to conditions effective to promote olefin hydrogenation.

In another embodiment the present invention provides a method of making substituted 2-phenyl linear alkylbenzene sulfonates, where the benzene ring of the substituted 2-phenyl linear alkylbenzene sulfonates is substituted with one or more groups designated R*, where R* is defined herein, the method comprising forming a composition comprising sulfonated substituted alpha-methyl styrene, at least one olefinic substrate, and at least one olefin metathesis catalyst, where the at least one olefinic substrate is selected from at least one linear alpha olefin, at least one linear internal olefin, or a combination thereof, where the benzene ring of the substituted alpha-methyl styrene is substituted with one or more groups designated R*, where R* is defined herein; subjecting the composition to conditions effective to promote a cross metathesis reaction to form cross metathesis products where the cross metathesis products comprise at least one substituted 2-phenyl linear alkene benzene sulfonate, where the at least one substituted 2-phenyl linear alkene benzene sulfonate is derived from a cross metathesis reaction between substituted alpha-methyl styrene sulfonate and at least one olefinic substrate, where the benzene ring of the substituted 2-phenyl linear alkene benzene sulfonate is substituted with one or more groups designated R*, where R* is defined herein; and subjecting the cross metathesis products comprising at least one substituted 2-phenyl linear alkene benzene sulfonate to conditions effective to promote olefin hydrogenation.

In another embodiment the present invention provides a method of making 2-phenyl linear alkylbenzene sulfonates, the method comprising forming a composition comprising sulfonated 3-phenyl-1-butene, at least one olefinic substrate, and at least one olefin metathesis catalyst, where the at least one olefinic substrate is selected from at least one linear alpha olefin, at least one linear internal olefin, or a combination thereof, subjecting the composition to conditions effective to promote a cross metathesis reaction to form cross metathesis products where the cross metathesis products comprise at least one 2-phenyl linear alkene benzene sulfonate, where the at least one 2-phenyl linear alkene benzene sulfonate is derived from a cross metathesis reaction between sulfonated 3-phenyl-1-butene and at least one olefinic substrate, and subjecting the cross metathesis products comprising at least one 2-phenyl linear alkene benzene sulfonate to conditions effective to promote olefin hydrogenation.

In another embodiment the present invention provides a method of making substituted 2-phenyl linear alkylbenzene sulfonates, where the benzene ring of the substituted 2-phenyl linear alkylbenzene sulfonates is substituted with one or more groups designated R*, where R* is defined herein, the method comprising forming a composition comprising sulfonated substituted 3-phenyl-1-butene, at least one olefinic substrate, and at least one olefin metathesis catalyst, where the at least one olefinic substrate is selected from at least one linear alpha olefin, at least one linear internal olefin, or a combination thereof, where the benzene ring of the substituted 3-phenyl-1-butene is substituted with one or more groups designated R*, where R* is defined herein; subjecting the composition to conditions effective to promote a cross metathesis reaction to form cross metathesis products where the cross metathesis products comprise at least one substituted 2-phenyl linear alkene benzene sulfonate, where the at least one substituted 2-phenyl linear alkene benzene sulfonate is derived from a cross metathesis reaction between substituted 3-phenyl-1-butene and at least one olefinic substrate, where the benzene ring of the substituted 2-phenyl linear alkene benzene is substituted with one or more groups designated R*, where R* is defined herein, and subjecting the cross metathesis products comprising at least one substituted 2-phenyl linear alkene benzene sulfonate to conditions effective to promote olefin hydrogenation.

In another embodiment, the present invention provides compositions having the following structure,

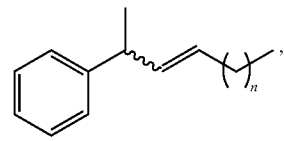

wherein n≥5.

In another embodiment, the present invention provides compositions having the following structure,

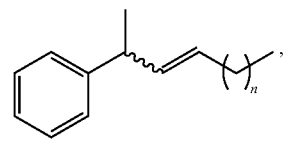

wherein n≥5, wherein the compositions may be optionally hydrogenated to an alkyl benzene and/or optionally aromatically sulfonated.

In another embodiment, the present invention provides compositions having the following structure,

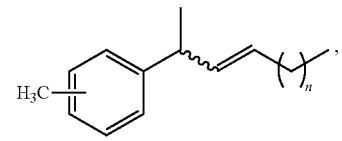

wherein n≥3, but n may not be 5 if —CH$_3$ is para.

In another embodiment, the present invention provides compositions having the following structure,

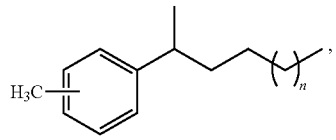

wherein n≥3, wherein the compositions may be optionally aromatically sulfonated.

In another embodiment, the present invention provides compositions having the following structure,

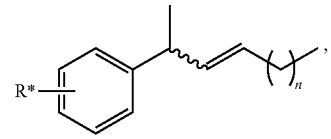

wherein n≥3, where R* is defined herein, with the proviso that R* may not be —CH$_3$.

In another embodiment, the present invention provides compositions having the following structure,

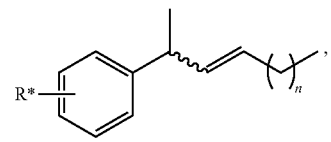

wherein n≥3, where R* is defined herein, with the proviso that R* may not be —CH$_3$— wherein the compositions may be optionally hydrogenated to a substituted alkyl benzene and/or optionally aromatically sulfonated.

In another embodiment, the present invention provides compositions having the structures as shown in FIG. 5, FIG. 6, FIG. 7, and/or FIG. 8.

In another embodiment, the present invention provides comp

In another embodiment, the present invention provides compositions prepared by methods of the present invention, where the methods are described herein.

In another embodiment, the present invention provides use of the compositions of the present invention.

In another embodiment, the present invention provides use of the compositions of the present invention, including but not limited to, use as surfactants for use in, including but not limited to, hand soaps, dish soaps, hard surface cleaners, laundry detergents, and in cleaning supplies.

In another embodiment, the present invention provides use of the compositions of the present invention, including but not limited to, use as fuels (e.g., diesel fuel and/or jet fuel) or fuel additives, lubricants, surfactants, cosmetics, flavors, fragrances, polymers, plastic additives, home and personal care products, or as precursors for preparing such materials.

These and other aspects and embodiments of the present invention will be apparent to the skilled artisan in light of the following detailed description and examples.

BRIEF DESCRIPTION OF THE DRAWINGS

FIG. 1 Chemical structures of hydrovinylation catalysts HV-1 to HV-16.
FIG. 2 $^1$H NMR of 3-phenyl-1-butene in CDCl$_3$.
FIG. 3 $^1$H NMR of 3-tolyl-1-butene in CDCl$_3$.
FIG. 4 $^{13}$C NMR of 3-tolyl-1-butene in CDCl$_3$.
FIG. 5 Representative 2-phenyl-3-alkene structures.
FIG. 6 Representative 2-(ortho-tolyl)-3-alkene structures
FIG. 7 Representative 2-(meta-tolyl)-3-alkene structures
FIG. 8 Representative 2-(para-tolyl)-3-alkene structures

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl (Ph), naphthyl, biphenyl, diphenylether, diphenylamine, benzophenone, and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as -D-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkenyl wherein "alkyl," "aryl", "aralkyl", "alkaryl", "alkenyl", and "alkynyl" are as defined above. The acetoxy group (—O(CO)CH$_3$; often abbreviated as OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a fluoro, chloro, bromo, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

The term "heterocyclic carbene" refers to a neutral electron donor ligand comprising a carbene molecule, where the carbenic carbon atom is contained within a cyclic structure and where the cyclic structure also contains at least one heteroatom. Examples of heterocyclic carbenes include "N-heterocyclic carbenes" wherein the heteroatom is nitrogen and "P-heterocyclic carbenes" wherein the heteroatom is phosphorus.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl((CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N ($C_5$-$C_{24}$ aryl)$_2$), di-N—($C_1$-$C_{24}$ alkyl),N—($C_5$-$C_{24}$ aryl)-substituted carbamoyl((CO)—N($C_1$-$C_{24}$ alkyl)($C_5$-$C_{24}$ aryl), thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N ($C_1$-$C_{24}$ alkyl)($C_5$-$C_{24}$ aryl), carbamido (—NH—(CO)—NH$_2$), cyano(—CI), cyanato (—O—C≡N), thiocyanato (—S—CI), isocyanate (—N═C═O), thioisocyanate (—N═C═S), formyl (—(CO)—H), thioformyl (—(CS)—H), amino (—NH$_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR═NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R includes without limitation hydrogen, CI—$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl (—SO$_2$—N(H)alkyl), $C_1$-$C_{24}$ dialkylaminosulfonyl (—SO$_2$—N(alkyl)$_2$), $C_5$-$C_{24}$ arylsulfonyl (—SO$_2$-aryl), boryl (—BH$_2$), borono (—B(OH)$_2$), boronato (—B(OR)$_2$ where R includes without limitation alkyl or other hydrocarbyl), phosphono (—P(O)(OH)$_2$), phosphonato (—P(O) (O⁻)$_2$), phosphinato (—P(O)(O⁻)), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

The term "ethenolysis" refers to the cross metathesis of a substrate with ethylene. For example, ethenolysis of methyl oleate produces methyl 9-decenoate and 1-decene. For ethenolysis references see Burdett, K. A.; Harris, L. D.; Margl, P.; Maughon, B. R.; Mokhtar-Zadeh, T.; Saucier, P. C.;

Wasserman, E. P. *Organometallics* 2004, 23, 2027; Nickel, A.; Ung, T., Mkrtumyan, G., Uy, J., Lee, C. H., Stoianova, D., Papazian, J., Wei, W.-H., Mallari, A., Schrodi, Y., Pederson, R. L. *Topic in Catalysis,* 2012, 55, 518-523; Warwel, S.; Brüse, F.; Demes, C.; Kunz, M.; Rüsch gen. Klaas M., *Chemosphere* 2001, 43, 39; Anderson, D. R.; Ung, T.; Mkrtumyan, G.; Bertrand, G.; Grubbs, R. H.; Schrodi, Y. *Organometallics* 2008, 27, 563.; Schrodi, Y.; Ung, T.; Vargas, A.; Mkrtumyan, G.; Lee, C. W.; Champagne, T. M.; Pederson, R. L.; Hong, S. H. *Clean—Soil, Air, Water* 2008, 36, 669.

The term "alkenolysis" refers to a cross metathesis reaction where a terminal olefin is used in a cross metathesis reaction with an internal double bond to produce different terminal olefins, where the initial terminal olefin cannot be ethylene. For example alkenolysis of methyl oleate with 1-butene produces methyl 9-decenoate, 1-decene, methyl-9-dodecenoate and 3-dodecene. For alkenolysis references see Schrodi, Y.; Pederson, R. L.; Kaido, H.; Tupy, M. J. US Pat. App. 2010/0145086, assigned to Elevance Renewable Sciences, Inc; and Nickel, A.; Ung, T., Mkrtumyan, G., Uy, J., Lee, C. H., Stoianova, D., Papazian, J., Wei, W.-H., Mallari, A., Schrodi, Y., Pederson, R. L. *Topic in Catalysis,* 2012, 55, 518-523, are incorporated by reference.

Optional" or "optionally" means that the subsequently described circumstance may or may not occur, so that the description includes instances where the circumstance occurs and instances where it does not. For example, the phrase "optionally substituted" means that a nonhydrogen substituent may or may not be present on a given atom, and, thus, the description includes structures wherein a nonhydrogen substituent is present and structures wherein a nonhydrogen substituent is not present.

The term "linear" when referring to a hydrocarbon or to an alkyl chain that is part of an alkylbenzene, whether the alkylbenzene is sulfonated or not, means a hydrocarbon comprising between 6 and 22 carbon atoms linked to one another to form a straight chain, wherein the carbon atoms of the straight chain may have only hydrogen atoms or a methyl group bonded to them as appendages.

The term "branched alkyl" when referring to a hydrocarbon or to an alkyl chain that is part of an alkylbenzene, whether the alkylbenzene is sulfonated or not, means a hydrocarbon comprising between 7 and 22 carbon atoms linked to one another to form a straight chain, wherein one or more of the carbon atoms of the straight chain may have a hydrogen atom or any alkyl group other than a methyl group (including without limitation, ethyl, propyl, and butyl groups), bonded to them as appendages.

The term "branched alkylbenzene" means a molecular species which comprises a branched alkyl chain appended to a benzene ring.

The term "branched alkylbenzene sulfonate" means a water soluble salt of a branched alkylbenzene that has been sulfonated.

The term "2-phenyl linear alkyl benzenes" or "2-PhLAB" means a benzene ring having at least one linear alkyl group attached to it, where the linear alkyl group comprises any number of carbon atoms between 6 and 22 (including every integral number there between) linked to one another so as to form a straight chain, wherein the carbon atoms of the straight chain (longest continuous carbon chain) may have only hydrogen atoms, or one or two methyl groups bonded to them as appendages, and wherein the benzene ring is attached to the linear alkyl group at a carbon atom that is adjacent to the terminal carbon atom of the straight chain (longest continuous carbon chain). In a 2-phenyl linear alkylbenzene the number of carbon atoms in the straight chain (longest continuous carbon chain) attached to the benzene ring is preferably 6 to 22, more preferably 7 to 16, and most preferably 9 to 14. Furthermore, for the purposes of this application, the benzene ring may also be substituted with one or more groups designated R*, where R* is $C_1$-$C_{12}$ alkyl, $C_5$-$C_{14}$ aryl, halo, amino, hydroxyl, alkoxy, acetoxy, nitro, cyano, substituted amino, napthyl, or biphenyl. Preferably R* is $C_1$-$C_{12}$ alkyl, $C_5$-$C_{14}$ aryl, halo, nitro, cyano, acetoxy, hydroxyl, and amino. More preferably R* is $C_1$-$C_6$ alkyl.

The terms "sulfonated 2-phenyl linear alkylbenzenes" or "2-phenyl linear alkylbenzene sulfonates" or "2-PhLAS" means 2-phenyl linear alkylbenzenes as defined above which further comprise a sulfonate group attached to the benzene ring of a 2-phenyl linear alkylbenzene as described above, regardless of the position of the sulfonate group on the benzene ring with respect to the location of the linear alkyl group; however, it is most common and preferred that the sulfonate group is attached to the benzene ring in the para-position with respect to the linear alkyl group. In addition, when the benzene ring is substituted with one or more groups designated R*, it is most common and preferred that the sulfonate group is attached to the benzene ring in the ortho, meta, or para-position with respect to the linear alkyl group.

The term "sulfonated" refers to the aryl ring (e.g., benzene ring) being substituted with at least one $SO_3M_x$ group which includes, sulfonic acid when $M_x$=H, methyl sulfonate when $M_x$=$CH_3$, ammonium sulfonate salt when $M_x$=$NH_4^+$; lithium, sodium, or potassium sulfonate salt with $M_x$=$Li^+$, $Na^+$, or $K^+$; respectively, magnesium, calcium or strontium sulfonate salts when $M_x$=$Mg^{+2}$, $Ca^{+2}$, or $Sr^{+2}$; respectively. Examples of sulfonated aryl rings (e.g., sulfonated benzene rings) are represented in Schemes 4 through 8.

The terms "2-$C_4$ to 20-$C_{40}$" refer to a short hand method of naming olefins. The first number represents the position of the double bond and the subscript number after carbon represents the number of carbons on the chain. For example, 2-$C_4$ stand for 2-butene, 3-$C_6$ stands for 3-hexene, up to 20-$C_{40}$ stands for 20-tetracontene.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn. If an olefinic structure is depicted which could potentially exist in either cis (Z) or trans (E) configuration, the use of a wavy line in the depiction indicates that the configuration may be either cis or trans or a combination of the two:

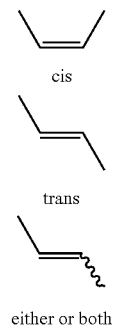

2-Phenyl Linear AlkylBenzene Sulfonates

The present invention provides a method of making 2-phenyl linear alkylbenzene sulfonates. More particularly, herein is described a method of making 2-phenyl linear alkene benzenes by cross metathesis of at least one cross metathesis substrate with at least one olefinic substrate in the presence of at least one olefin metathesis catalyst, where the at least one cross metathesis substrate is selected from alpha-methyl styrene, substituted alpha-methyl styrene, sulfonated alpha-methyl styrene (AMS), sulfonated substituted alpha-methyl styrene, 3-phenyl-1-butene (3PhlC$_4$), substituted 3-phenyl-1-butene, sulfonated 3-phenyl-1-butene, and sulfonated substituted 3-phenyl-1-butene, where the at least one olefinic substrate is selected from at least one linear alpha olefin, at least one linear internal olefin, or a combination thereof. The 2-phenyl linear alkene benzene (2-PhLAeB or 2-Ph*LAeB) product is hydrogenated to yield 2-phenyl alkylbenzene. The 2-phenyl linear alkylbenzene product is sulfonated to yield high isomeric purity 2-phenyl linear alkylbenzene sulfonate (2-PhLAS or 2-Ph*LAS), where the isomeric purity is at least 85% by weight based on the total weight of linear alkyl benzene sulfonate isomers. Scheme 1 below shows a general synthesis of 2-phenyl linear alkyl benzene sulfonates using cross metathesis.

Hydrovinylation

Hydrovinylation is an atom-efficient process to add ethylene to a double bond (see Scheme 2). Several recent hydrovinylation reviews include Jolly, P. W.; Wilke, G. In Applied Homogeneous Catalysis with Organometallic Compounds; Cornils, B., Herrmann, W. A., Eds.; VCH: New York, 2002; Vol. 3, p 1164, RajanBabu, T. V.; Chem. Rev. 2003, 103, 2845-2860, RajanBabu, T. V.; Synlett 2009, 6, 853-885 and Ceder, R. M.; Grabulosa, A.; Muller, G.; Rocamora, M. Catalysis Science and Technology 2013, (manuscript accepted, DOI: 10.1039/C3CY00084B) describe numerous hydrovinylation catalysts and reactions, which are incorporated herein by reference. These reviews disclose asymmetric hydrovinylation reactions. Any racemic or asymmetric hydrovinylation catalyst can be used in the present invention.

Scheme 2. General hydrovinylation reaction

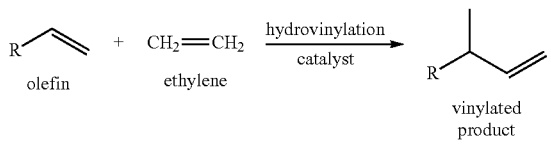

R = hydrocarbyl, substituted hydrocarbyl, heteroatom-containing hydrocarbyl, substituted heteroatom-containing hydrocarbyl, and functional groups.

Scheme 1. General synthesis of 2-phenyl linear alkylbenzene sulfonates using cross methathesis.

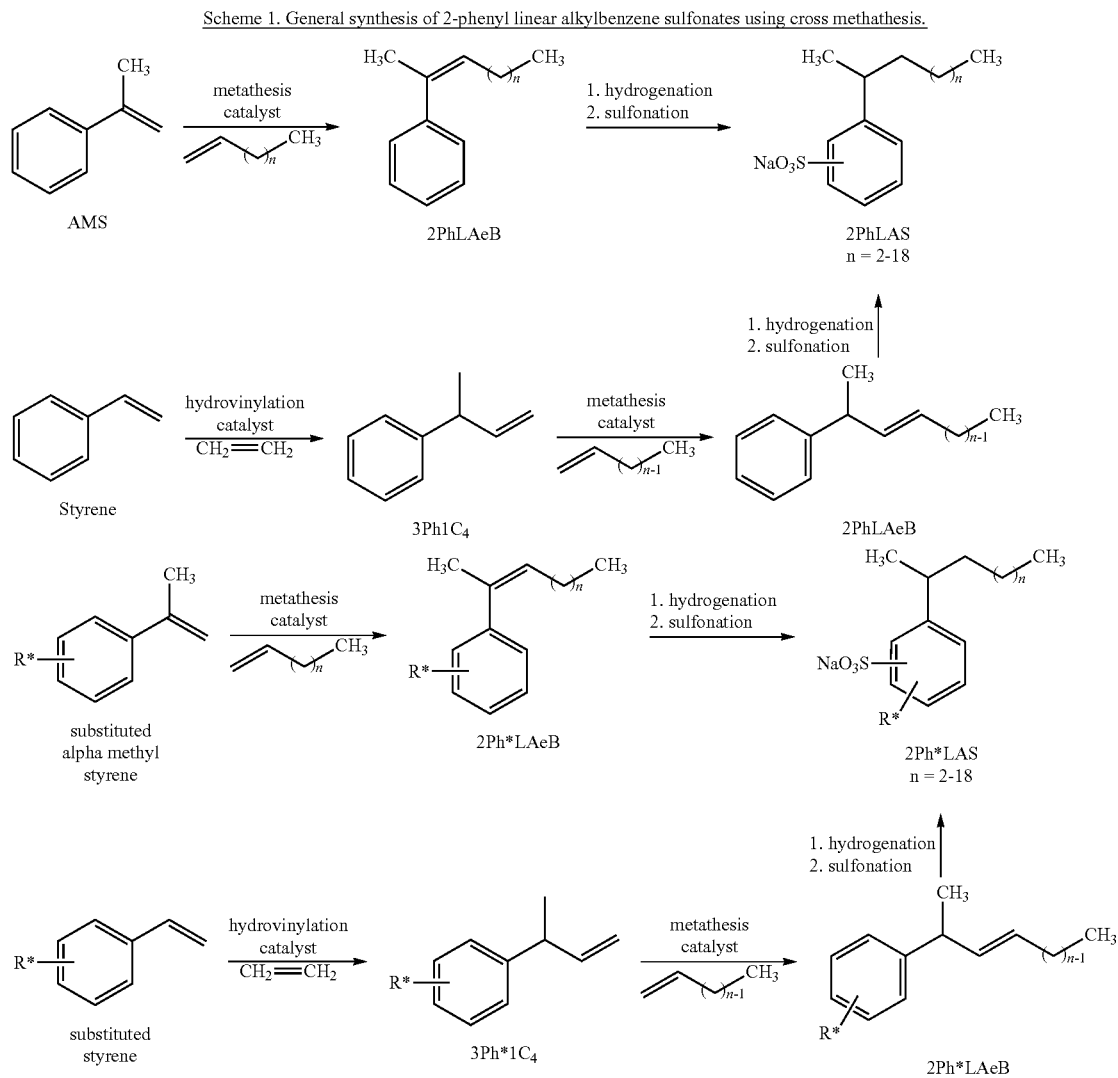

Numerous embodiments of catalysts that affect the hydrovinylation of styrene and other olefins [i.e., codimerization of styrene and ethylene] have been reported in academic and patent literature. These include but are not limited to:

Hydrates of RuCl$_3$ and RhCl$_3$ [Alderson, T.; Jenner, E. L.; Lindsey, R. V., Jr. J. Am. Chem. Soc. 1965, 87, 5638.] is incorporated by reference.

Ni(II) hydrovinylation complexes include:

NiCl$_2$(PBu$_3$)$_2$AlEt$_2$Cl [Dzhemilev, U. M.; Gubaidullin, L. Y.; Tolstikov, G. A. Bull. Acad. Sci. USSR 1976, 2009.] Ni(acac)$_2$Et$_3$Al/BF$_3$.OEt$_2$P(OPh)$_3$ [Azizov, A. G.; Mamedaliev, G. A.; Aliev, S. M.; Aliev, V. S. Azerb. Khim. Zh. 1979, 3.] Ni(Ar)(Br)$_2$(PPh$_3$)$_2$/BF$_3$.OEt$_2$ where Ar=o-tolyl, 1-naphthyl or mesityl [Kawata, N.; Maruya, K.; Mizoroki, T.; Ozaki, A. Bull. Chem. Soc. Jpn. 1971, 44, 3217. Kawata, N.; Maruya, K.; Mizoroki, T.; Ozaki, A. Bull. Chem. Soc., Jpn. 1974, 47, 413. Kawakami, K.; Kawata, N.; Maruya, K.; Mizoroki, T.; Ozaki, A. J. Catal. 1975, 39, 134.] NiX$_2$/AlEt$_3$/BF$_3$.OEt$_2$/P(OPh)$_3$ [Mamedaliev, G. A.; Azizov, A. G.; Yu, G. Pol. J. (Japan) 1985, 17, 1075. Azizov, A. G.; Mamedaliev, G. A.; Aliev, S. M.; Aliev, V. S. Azerb. Khim. Zh. 1978, 3.] [Ni($\eta^3$-allyl)Br]$_2$/PPh$_3$/AgOTf [Nomura, N.; Jin, J.; Park, H.; Rajan-Babu, T. V. J. Am. Chem. Soc. 1998, 120, 459.] [Ni(MeCN)$_6$][BF$_4$]$_2$, L, AlEt$_2$Cl (L=monophosphine, diphosphine, aminophosphine) [Fassina, V.; Ramminger, C.; Seferin, M.; Monteiro, A. L. Tetrahedron 2000, 56, 7403-7409.] trans-[Ni(2,4,6-Me$_3$C$_6$H$_2$)(CH$_3$CN)(P(CH$_2$Ph)$_3$)$_2$]BF$_4$ [Ceder, R.; Muller, G.; Ordinas, J. I. J. Mol. Catal. 1994, 92, 127, and Muller, G.; Ordinas, J. I. J. Mol. Catal. A: Chem. 1997, 125, 97] are all incorporated by reference.

Pd(II) hydrovinylation complexes include:

PdCl$_2$(PhCN)$_2$ [Barlow, M. G.; Bryant, M. J.; Haszeldine, R. N.; Mackie, A. G. J. Organomet. Chem. 1970, 21, 215.] Pd(OAc)$_2$/Et$_2$P(CH$_2$)$_3$PEt$_2$/PTSA [Drent, E. U.S. Pat. No. 5,227,561, 1993. Kawamoto, K.; Tatani, A.; Imanaka, T.; Teranishi, S. Bull. Chem. Soc., Jpn. 1971, 44, 1239.] (PPh$_3$)$_2$Pd(Ph)(X)/H$_2$O, where X=Br or I [Nozima, H.; Kawata, N.; Nakamura, Y.; Maruya, K.; Mizoroki, T.; Ozaki, A. Chem. Lett. 1973, 1163] are all incorporated by reference.

Co(II) hydrovinylation complexes include:

CoL$_2$Cl$_2$, AlEt$_2$Cl (L=monophosphine or L$_2$=diphosphine) [Grutters, M. M. P.; van der Vlugt, J. I.; Pei, Y.; Mills, A. M.; Lutz, M.; Spek, A. L.; Müller, C.; Moberg, C.; Vogt, D. Adv. Synth. Catal. 2009, 351, 2199-2208] are all incorporated by reference.

Ru(II) hydrovinylation complexes include:

(PCy$_3$)$_2$(CO)RuHCl/HBF$_4$.OEt$_2$ [Yi, C. S.; He, Z.; Lee, D. W. Organometallics 2001, 20, 802-804.] (L)(CO)RuHCl/AgX (L=2 PCy$_3$, diphosphine, X=OTf, SbF$_6$) [Rajan-Babu, T. V.; Nomura, N.; Jin, J.; Nandi, M.; Park, H.; Sun, X. J. Org. Chem. 2003, 68, 8431. Sanchez, R. P. Jr.; Connell, B. T. Organometallics 2008, 27, 2902-2904] are all incorporated by reference.

Scheme 3 below shows a general preparation of 3-phenyl-1-butene (3Ph1C$_4$) by the hydrovinylation of styrene and a general preparation of substituted 3-phenyl-1-butene (3Ph*1C$_4$) by the hydrovinylation of substituted styrene.

Scheme 3. Hydrovinylation of styrene to give 3-phenyl-1-butene (3Ph1C$_4$) and hydrovinylation of substituted styrene to give substituted 3-phenyl-1-butene (3Ph*1C$_4$).

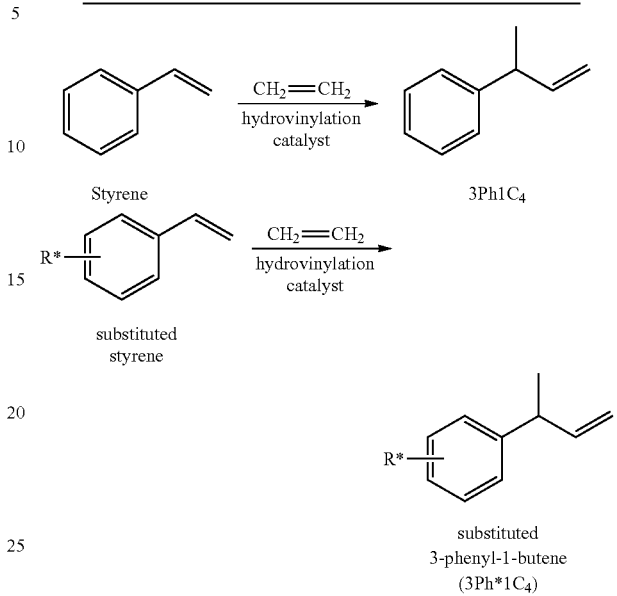

Examples of compounds useful in the hydrovinylation reaction include but are not limited to compounds which are also useful as cross metathesis substrates including substituted styrenic compounds, non-substituted styrenic compounds, substituted styrenes, non-substituted styrenes, substituted divinylbenzenes, non-substituted divinylbenzenes, substituted allylbenzenes, non-substituted allylbenzenes, sulfonated substituted styrenic compounds, sulfonated non-substituted styrenic compounds, sulfonated substituted styrenes, sulfonated non-substituted styrenes, sulfonated substituted divinylbenzenes, sulfonated non-substituted divinylbenzenes, sulfonated substituted allylbenzenes, and sulfonated non-substituted allylbenzenes. Any of the substituted styrenic compounds, substituted styrenes, substituted divinylbenzenes, substituted allylbenzenes, sulfonated substituted styrenic compounds, sulfonated substituted styrenes, sulfonated substituted divinylbenzenes, and sulfonated substituted allylbenzenes may be ortho, meta, para substituted with various R* substituent groups, where R* is defined herein. Also combinations of various R* substituent groups may be present on the phenyl ring.

Preferred examples of unsubstituted compounds useful in the hydrovinylation reaction include styrene, and sulfonated styrene, where styrene is more preferred.

Examples of substituted styrenes useful in the hydrovinylation reaction include but are not limited to the ortho, meta or para substituted isomers of tolyl styrene, ethylstyrene, propylstyrene, isopropylstyrene, butylstyrene, sec-butylstyrene, isobutylstyrene, tert-butylstyrene, fluorostyrene, chlorostyrene, bromostyrene, iodostyrene, nitrostyrene, cyanostyrene, acetoxystyrene, hydroxystyrene, alkoxystyrene compounds, aminostyrene, and substituted aminostyrene compounds, styrenes derived from phenyl fused rings like naphthylstyrene and biphenylstyrene. Also combinations of any of these various R* substituent groups may be present on the same phenyl ring. The R* substituent group may be substituted on the aromatic ring in one or more ortho, meta or para-positions.

Preferred examples of substituted styrenes useful in the hydrovinylation reaction include but are not limited to the ortho, meta or para substituted isomers of tolyl styrene, ethylstyrene, propylstyrene, isopropylstyrene, fluorostyrene, chlorostyrene, bromostyrene, iodostyrene, nitrostyrene, cyanostyrene, acetoxystyrene, hydroxystyrene, and aminostyrene. Also combinations of any of these various R* substituent groups may be present on the same phenyl ring. The R* substituent group may be substituted on the aromatic ring in one or more ortho, meta or para-positions.

More preferred examples of substituted styrenes useful in the hydrovinylation reaction include but are not limited to the ortho, meta or para substituted isomers of tolyl styrene and ethylstyrene. Also combinations of any of these various R* substituent groups may be present on the same phenyl ring. The R* substituent group may be substituted on the aromatic ring in one or more ortho, meta or para-positions.

Alternative routes into 3-phenyl-1-butene and substituted 3-phenyl-1-butene include but not limited to; 1) nucleophilic substitution of methyl Grignard with a 3-phenyl-2-propenyl halide or substituted 3-phenyl-2-propenyl halide (Alexakis, A.; Backvall, J. E.; Krause, N.; Pamies, O.; Dieguez, M. Chem. Rev. 2008, 108, 2796; Trost, B. M.; Crawley, M. L. Chem. Rev. 2003, 103, 2921; Trost, B. M.; Van Vranken, D. L. Chem. Rev. 1996, 96, 395); 2) 1,4-butadiene hydroarylation with benzene; and 3) Wittig reaction of 2-phenyl propanal or substituted 2-phenyl propanal (Marshall, J. A.; DeHoff, B. S., Cleary, D. G. J. Org. Chem. 1986, 51, 1735; Bussas, R.; Muenster, H.; Kresze, G. J. Org. Chem. 1983, 48, 2828).

Hydrovinylation catalysts suitable for the present invention include but are not limited to hydrates of $RuCl_3$ and $RhCl_3$, $NiCl_2(PBu_3)_2/AlEt_2Cl$, $Ni(acac)_2/Et_3Al/BF_3.OEt_2/P(OPh)_3$, $Ni(Ar)(Br)(PR_3)_2/BF_3.OEt_2$, $NiX_2/AlEt_3/BF_3.OEt_2/P(OPh)_3$, $[Ni(\eta^3\text{-allyl})Br]_2/PPh_3/AgOTf$ (X=Cl, Br, I), $[Ni(MeCN)_6][BF_4]_2L/AlEt_2Cl$ (L=monophosphine, diphosphine, aminophosphine), trans-$[Ni(2,4,6\text{-}Me_3C_6H_2)(CH_3CN)(P(CH_2Ph)_3)_2]BF_4$, $PdCl_2(PhCN)_2$, $Pd(OAc)_2/Et_2P(CH_2)_3PEt_2/PTSA$, $(PPh_3)_2Pd(Ph)(X/H_2O)$ (X=OTf, $SbF_6$), $CoL_2Cl_2/AlEt_2Cl$ (L=monophosphine or $L_2$=diphosphine), $(PCy_3)_2(CO)RuHCl/HBF_4.OEt_2$, and (L)(CO)RuHCl/AgX (L=2 $PCy_3$, diphosphine, X=OTf, $SbF_6$).

Additional hydrovinylation catalysts suitable for use in the present invention include hydrovinylation catalysts HV-1 to HV-16 shown in FIG. 1.

Preferred hydrovinylation catalysts suitable for the present invention include:
$[Ni(MeCN)_6][BF_4]_2PPh_3/AlEt_2Cl$, $Co(PPh_3)_2Cl_2/AlEt_2Cl$, $(PCy_3)_2(CO)RuHCl/HBF_4.OEt_2$ and $(PCy_3)_2(CO)RuHCl/AgOTf$.

More preferred hydrovinylation catalysts suitable for the present invention include: $Co(PPh_3)_2Cl_2/AlEt_2Cl$ and $(PCy_3)_2(CO)RuHCl/HBF_4.OEt_2$.

Cross Metathesis Substrates

Cross metathesis substrates for use with the present invention include substituted and non-substituted styrenic compounds, substituted and non-substituted styrenes, substituted and non-substituted divinylbenzenes, substituted and non-substituted allylbenzenes, substituted and non-substituted 4-phenyl-1-butene, substituted and non-substituted alpha-methyl styrenes, sulfonated alpha-methyl styrenes, sulfonated substituted alpha-methyl styrenes, 3-phenyl-1-butenes, substituted 3-phenyl-1-butenes, sulfonated 3-phenyl-1-butenes, and sulfonated substituted 3-phenyl-1-butenes. Preferred cross metathesis substrates for use with the present invention include 3-phenyl-1-butenes, substituted 3-phenyl-1-butenes, More preferred cross metathesis substrates for use with the present invention include 3-phenyl-1-butenes, substituted 3-phenyl-1-butenes, 3-tolyl-1-butenes, alpha-methyl styrenes, and substituted alpha-methyl styrenes. 3-phenyl-1-butene and 3-tolyl-1-butene may be prepared as described herein.

The term "substituted AM*S" refers to the aryl ring (benzene ring) of alpha-methyl styrene being substituted with one or more R* substituent groups (see Scheme 4).

Scheme 4. Substituted AM*S

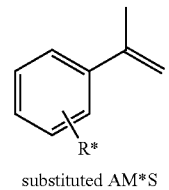

substituted AM*S

The terms "sulfonated AMS" and "sulfonated substituted AM*S" refers to the aryl ring (benzene ring) of alpha-methyl styrene and substituted alpha-methyl styrene being substituted with at least one $SO_3M_x$ group (see Scheme 5) which includes, sulfonic acid when $M_x$=H, methyl sulfonate when $M_x$=$CH_3$, ammonium sulfonate salt when $M_x$=$NH_4^+$; lithium, sodium, or potassium sulfonate salt with $M_x$=$Li^+$, $Na^+$, or $K^+$; respectively, magnesium, calcium or strontium sulfonate salts when $M_x$=$Mg^{+2}$, $Ca^{+2}$, or $Sr^{+2}$; respectively.

Scheme 5. Sulfontated AMS and Sulfonated Substituted AM*S

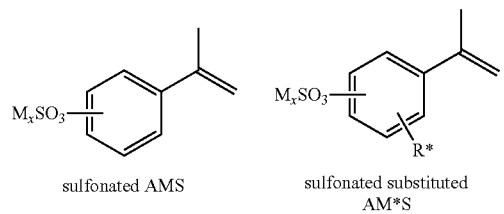

sulfonated AMS sulfonated substituted AM*S $M_x$ = H, $CH_3$, $NH_4^+$, $Li^+$, $Na^+$, $K^+$, $Cs^+$, $Mg^{+2}$, $Ca^{+2}$, or $Sr^{+2}$ The term "substituted 3-phenyl-1-butene" refers to the phenyl ring (benzene ring) of substituted 3-phenyl-1-butene being substituted with one or more R* substituent groups (see Scheme 6).

Scheme 6. Substituted 3-phenyl-1-butene

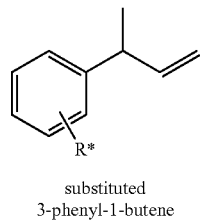

substituted
3-phenyl-1-butene

Examples of substituted 3-phenyl-1-butene produced in this reaction include but not limited to 3-tolyl-1-butene, 3-ethylphenyl-1-butene, 3-propylphenyl-1-butene, 3-isopropylphenyl-1-butene, 3-butylphenyl-1-butene, 3-sec-butylphenyl-1-butene, 3-isobutylphenyl-1-butene, 3-tert-butylphenyl-1-butene, 3-fluorophenyl-1-butene, 3-chlorophenyl-1-butene, 3-bromophenyl-1-butene, 3-iodophenyl-1-butene, 3-nitrophenyl-1-butene, 3-cyanophenyl-1-butene, 3-acetoxyphenyl-1-butene, 3-hydroxyphenyl-1-butene, substituted 3-hydroxyphenyl-1-butene compounds, 3-aminophenyl-1-butene, and substituted 3-aminophenyl-1-butene compounds, styrenes derived from phenyl fused rings like 3-naphthyl-1-butene and 3-biphenyl-1-butene. Also combinations of any of these various R* substituent groups may be present on the same phenyl ring. The R* substituent group may be substituted on the aromatic ring in one or more ortho, meta or para-positions.

Preferred examples of substituted 3-phenyl-1-butene produced in this reaction include but not limited to 3-tolyl-1-butene, 3-ethylphenyl-1-butene, 3-propylphenyl-1-butene, 3-isopropylphenyl-1-butene, 3-fluorophenyl-1-butene, 3-chlorophenyl-1-butene, 3-bromophenyl-1-butene, 3-iodophenyl-1-butene, 3-nitrophenyl-1-butene, 3-cyanophenyl-1-butene, 3-acetoxyphenyl-1-butene, 3-hydroxyphenyl-1-butene, 3-aminophenyl-1-butene, and styrenes derived from phenyl fused rings like 3-naphthyl-1-butene and 3-biphenyl-1-butene. Also combinations of any of these various R* substituent groups may be present on the same phenyl ring. The R* substituent group may be substituted on the aromatic ring in one or more ortho, meta or para-positions.

Even more referred examples of substituted 3-phenyl-1-butene produced in this reaction include but not limited to 3-tolyl-1-butene and 3-ethylphenyl-1-butene. Also combinations of any of these various R* substituent groups may be present on the same phenyl ring. The R* substituent group may be substituted on the aromatic ring in one or more ortho, meta or para-positions.

The term "sulfonated 3-phenyl-1-butene" refers to the phenyl ring (benzene ring) of substituted 3-phenyl-1-butene being substituted with at least one or more R* groups and at least one $SO_3M_x$ group (see Scheme 7) which includes, sulfonic acid when $M_x$=H, methyl sulfonate when $M_x$=$CH_3$, ammonium sulfonate salt when $M_x$=$NH_4^+$; lithium, sodium, or potassium sulfonate salt with $M_x$=$Li^+$, $Na^+$, or $K^+$; respectively, magnesium, calcium or strontium sulfonate salts when $M_x$=$Mg^{+2}$, $Ca^{+2}$, or $Sr^{+2}$; respectively.

The term "sulfonated 3-phenyl-1-butene" refers to the aryl ring (benzene ring) of 3-phenyl-1-butene being substituted with at least one $SO_3M_x$ group (see Scheme 7) which includes, sulfonic acid when $M_x$=H, methyl sulfonate when $M_x$=$CH_3$, ammonium sulfonate salt when $M_x$=$NH_4^+$; lithium, sodium, or potassium sulfonate salt with $M_x$=$Li^+$, $Na^+$, or $K^+$; respectively, magnesium, calcium or strontium sulfonate salts when $M_x$=$Mg^{+2}$, $Ca^{+2}$, or $Sr^{+2}$; respectively.

Scheme 7. Sulfonated 3-phenyl-1-butene

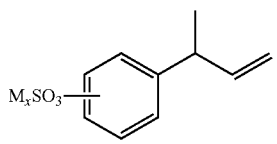

sulfonated 3-phenyl-1-butene $M_x$ = H, $CH_3$, $NH_4^+$, $Li^+$, $Na^+$,
$K^+$, $Cs^+$, $Mg^{+2}$, $Ca^{+2}$, or $Sr^{+2}$ The term "sulfonated substituted 3-phenyl-1-butene" refers to the aryl ring (benzene ring) of substituted 3-phenyl-1-butene being substituted with at least one $SO_3M_x$ group (see Scheme 8) which includes, sulfonic acid when $M_x$=H, methyl sulfonate when $M_x$=$CH_3$, ammonium sulfonate salt when $M_x$=$NH_4^+$; lithium, sodium, or potassium sulfonate salt with $M_x$=$Li^+$, $Na^+$, or $K^+$; respectively, magnesium, calcium or strontium sulfonate salts when $M_x$=$Mg^{+2}$, $Ca^{+2}$, or $Sr^{+2}$; respectively.

Scheme 8. Sulfonated substituted 3-phenyl-1-butene

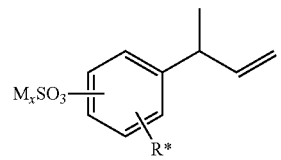

sulfonated substituted 3-phenyl-1-butene $M_x$ = H, $CH_3$, $NH_4^+$, $Li^+$, $Na^+$,
$K^+$, $Cs^+$, $Mg^{+2}$, $Ca^{+2}$, or $Sr^{+2}$ Examples of sulfonated substituted 3-phenyl-1-butene produced in this reaction include but not limited to the sulfonate of 3-tolyl-1-butene, 3-ethylphenyl-1-butene, 3-propylphenyl-1-butene, 3-isopropylphenyl-1-butene, 3-butylphenyl-1-butene, 3-sec-butylphenyl-1-butene, 3-isobutylphenyl-1-butene, 3-tert-butylphenyl-1-butene, 3-fluorophenyl-1-butene, 3-chlorophenyl-1-butene, 3-bromophenyl-1-butene, 3-iodophenyl-1-butene, 3-nitrophenyl-1-butene, 3-cyanophenyl-1-butene, 3-acetoxyphenyl-1-butene, 3-hydroxyphenyl-1-butene, substituted 3-hydroxyphenyl-1-butene compounds, 3-aminophenyl-1-butene, and substituted 3-aminophenyl-1-butene compounds, styrenes derived from phenyl fused rings like 3-naphthyl-1-butene and 3-biphenyl-1-butene. Also combinations of any of these various R* substituent groups may be present on the same phenyl ring. The R* substituent group may be substituted on the aromatic ring in one or more ortho, meta or para-positions.

Olefinic Substrates

Olefinic substrates for use with the present invention include internal olefins, alpha olefins, and combinations thereof. Preferred, olefinic substrates for use with the present invention include linear internal olefins, linear alpha olefins, and combinations thereof.

The term "internal olefin" as used herein means an olefin wherein each of the olefinic carbons is substituted by at least one non-hydrogen substituent. The non-hydrogen substituents are selected from hydrocarbyl, and substituted hydrocarbyl, heteroatom-containing hydrocarbyl, substituted heteroatom-containing hydrocarbyl, and functional groups. The internal olefin is therefore at least disubstituted, and may further include additional non-hydrogen substituents such that the internal olefin is tri- or tetra-substituted. Each of the substituents on the internal olefinic carbons may be further substituted as described herein. The internal olefin may be in the Z- or E-configuration.

The internal olefin may be a single compound or a mixture of compounds. The internal olefin may comprise a single internal olefin or a plurality of internal olefins. A mixture of internal olefins may be used. The internal olefin may be hydrophobic or hydrophilic, although in a preferred embodiment, the internal olefin is hydrophobic.

For example, the internal olefin may be represented by the formula $(R^I)(R^{II})C=C(R^{III})(R^{IV})$, wherein $R^I$, $R^{II}$, $R^{III}$, and $R^{IV}$ are independently selected from H, hydrocarbyl, and substituted hydrocarbyl, provided that at least one of $R^I$ and $R^{II}$ and at least one of $R^{III}$ and $R^{IV}$ is other than H. In a preferred embodiment, either $R^I$ or $R^{II}$ and either $R^{III}$ or $R^{IV}$ is H, such that the internal olefin is di-substituted.

Examples of internal di-substituted olefins may be represented by the formula $(R^I)(R^{II})C=C(R^{III})(R^{IV})$, wherein $R^I$, $R^{II}$, $R^{III}$, and $R^{IV}$ are independently selected from H, 2-$C_4$ to 20-$C_{40}$, and substituted 2-$C_4$ to 20-$C_{40}$, provided that at least one of $R^I$ and $R^{II}$ and at least one of $R^{III}$ and $R^{IV}$ is other than H. In a preferred embodiment, either $R^I$ or $R^{II}$ and either $R^{III}$ or $R^{IV}$ is H, such that the internal olefin is di-substituted.

The term "linear internal olefin" as used herein means an internal di-substituted olefin represented by the formula $(R^I)(R^{II})C=C(R^{III})(R^{IV})$, wherein $R^I$, $R^{II}$, $R^{III}$, and $R^{IV}$ are independently selected from H, 2-$C_4$ to 20-$C_{40}$, provided that either $R^I$ or $R^{II}$ and either $R^{III}$ or $R^{IV}$ is H, where the carbon atoms in the chain may have only hydrogen atoms or a methyl group bonded to them. In other words, for example, if $R^I$ and $R^{II}$ are both H, then $R^{III}$ and $R^{IV}$ may be $C_2$-$C_{19}$ alkyl, where the carbon atoms in the alkyl chain may have only hydrogen atoms or a methyl group bonded to them. The term "linear internal olefin" as used herein also means any internal tri-substituted olefin represented by the formula $(R^I)(R^{II})C=C(R^{III})(R^{IV})$, where $R^I$ and $R^{II}$ are either H or methyl, but not both H and not both methyl, $R^{III}$ and $R^{IV}$ may be independently $C_2$-$C_{19}$ alkyl, where the carbon atoms of the alkyl chain may have only hydrogen atoms or a methyl group bonded to them. The term "linear internal olefin" as used herein also means an internal tetra-substituted olefin represented by the formula $(R^I)(R^{II})C=C(R^{III})(R^{IV})$, where $R^I$ and $R^{III}$ are both methyl and $R^{II}$ and $R^{IV}$ may be independently $C_2$-$C_{19}$ alkyl, where the carbon atoms of the alkyl chain may have only hydrogen atoms or a methyl group bonded to them. The linear internal olefin may be in the Z- or E-configuration.

Examples of linear internal olefins that may be used for the cross-metathesis partner with alpha-methyl styrene (AMS) or sulfonated alpha-methyl styrene (sulfonated AMS) to produce 2-PhLAeB and sulfonated 2-PhLAeB are shown in Scheme 9.

Scheme 9.
Cross metathesis of linear internal olefins with alpha-methyl styrene or sulfonated alpha-methyl styrene.

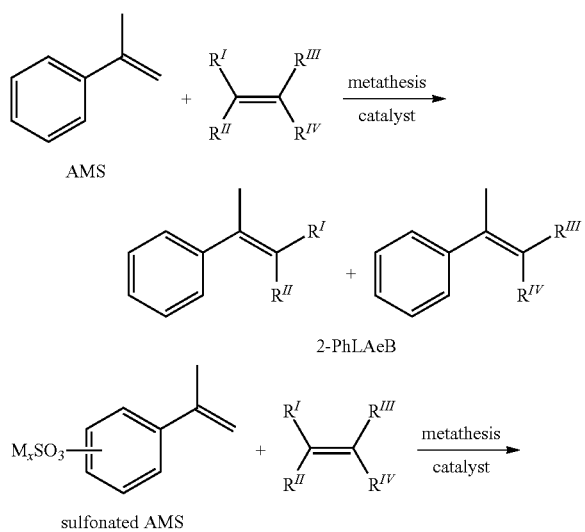

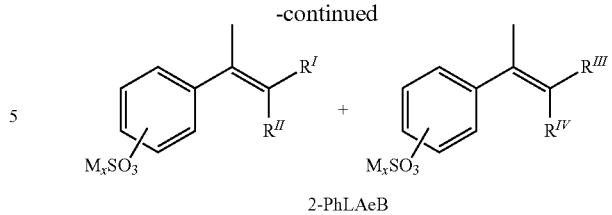

2-PhLAeB when $R^I$ and $R^{III}$ are H and $R^{II}$ and $R^{IV}$ are $C_3$ to $C_{19}$ alkyl
$M_x$ = H, $CH_3$, $NH_4^+$, $Li^+$, $Na^+$, $K^+$, $Cs^+$, $Mg^{+2}$, $Ca^{+2}$, or $Sr^{+2}$ Examples of linear internal olefins that may be used for the cross-metathesis partner with substituted alpha-methyl styrene (substituted AM*S) to produce 2-Ph*LAeB (substituted 2-phenyl alkenylbenzene) and 2-Ph*LAeS (substituted 2-phenyl alkenylbenzene sulfonate) are shown in Scheme 10.

Scheme 10.
Cross metathesis of linear internal olefins with substituted alpha-methyl styrene or sulfonated substituted alpha-methyl styrene.

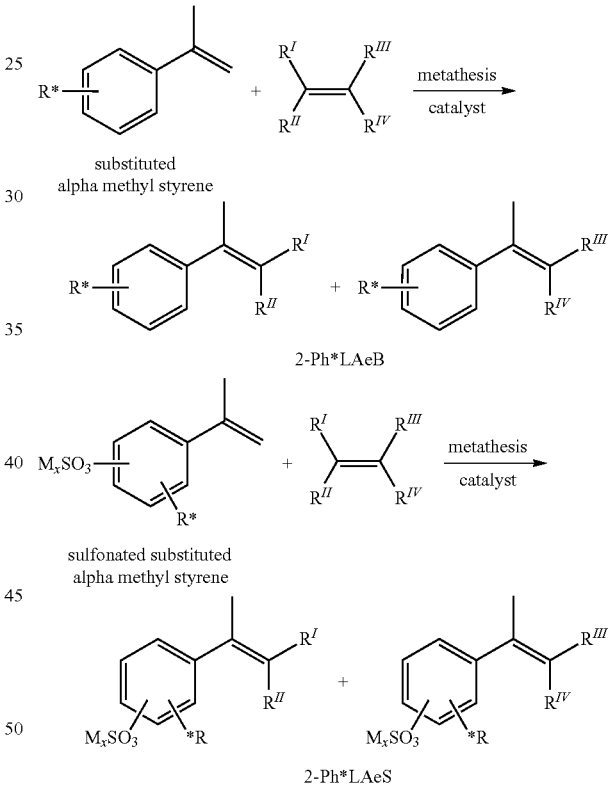

2-Ph*LAeS when $R^I$ and $R^{III}$ are H and $R^{II}$ and $R^{IV}$ are $C_3$ to $C_{19}$ alkyl
$M_x$ = H, $CH_3$, $NH_4^+$, $Li^+$, $Na^+$, $K^+$, $Cs^+$, $Mg^{+2}$, $Ca^{+2}$, or $Sr^{+2}$ Examples of preferred linear internal olefins that may be used for the cross metathesis with cross metathesis substrates such as alpha-methyl styrene (AMS), sulfonated AMS, substituted alpha-methyl styrene (AM*S), and sulfonated substituted AM*S include 2-butene, 3-hexene, 4-octene, 5-decene, 6-dodecene, 7-teradecene, 8-hexadecene, 9-octadecene, 10-$C_{20}$, 11-$C_{22}$, 12-$C_{24}$, 13-$C_{26}$, 14-$C_{28}$, 15-$C_{30}$, 16-$C_{32}$, 17-$C_{34}$, 18-$C_{36}$, 19-$C_{38}$, and 20-$C_{40}$.

Examples of more preferred linear internal olefins that may be used for the cross metathesis with cross metathesis substrates such as alpha-methyl styrene, and sulfonated alpha-methyl styrene, substituted alpha-methyl styrene, and sulfonated substituted alpha-methyl styrene include 5-decene, 6-dodecene, 7-teradecene, 8-hexadecene, 9-octadecene, 10-$C_{20}$, 11-$C_{22}$, 12-$C_{24}$, and 13-$C_{26}$.

Examples of the most preferred linear internal olefins that may be used for the cross metathesis with cross metathesis substrates such as alpha-methyl styrene, sulfonated alpha-methyl styrene, substituted alpha-methyl styrene, and sulfonated substituted alpha-methyl styrene include 9-octadecene, 10-$C_{20}$, and 11-$C_{22}$.

Examples of linear internal olefins that may be used for the cross-metathesis partner with 3-phenyl-1-butene or sulfonated 3-phenyl-1-butene to produce 2-PhLAeB and sulfonated 2-PhLAeB are shown in Scheme 11.

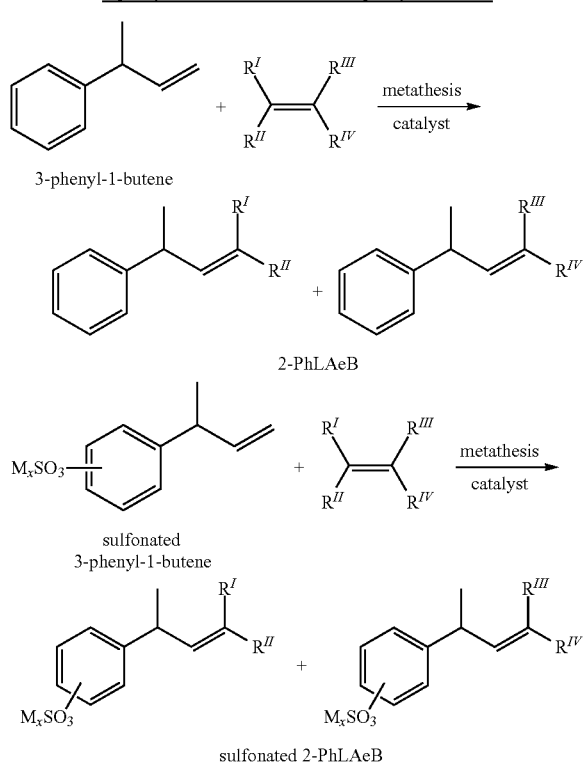

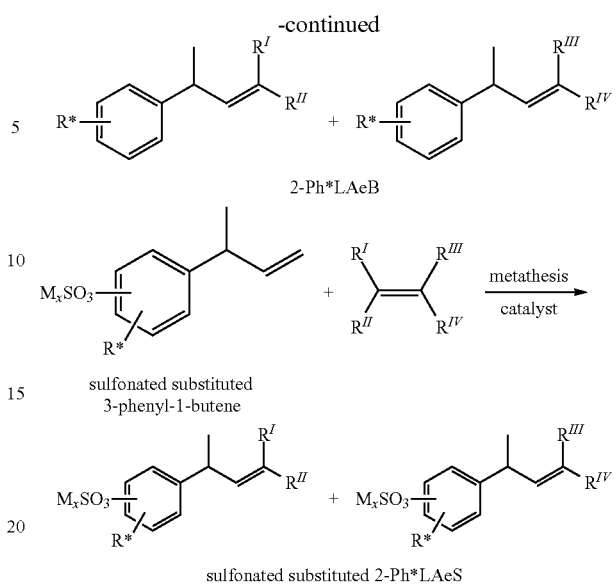

when $R^I$ and $R^{III}$ are H and $R^{II}$ and $R^{IV}$ are $C_2$ to $C_{18}$ alkyl
$M_x$ = H, $CH_3$, $NH_4^+$, $Li^+$, $Na^+$, $K^+$, $Cs^+$, $Mg^{+2}$, $Ca^{+2}$, or $Sr^{+2}$ Examples of preferred linear internal olefins that may be used for the cross metathesis with cross metathesis substrates such as 3-phenyl-1-butene, sulfonated 3-phenyl-1-butene, substituted 3-phenyl-1-butene, and sulfonated substituted 3-phenyl-1-butene include 2-butene, 3-hexene, 4-octene, 5-decene, 6-dodecene, 7-teradecene, 8-hexadecene, 9-octadecene, 10-$C_{20}$, 11-$C_{22}$, 12-$C_{24}$, 13-$C_{26}$, 14-$C_{28}$, 15-$C_{30}$, 16-$C_{32}$, 17-$C_{34}$, 18-$C_{36}$, 19-$C_{38}$, and 20-$C_{40}$.

Examples of more preferred linear internal olefins that may be used for the cross metathesis with cross metathesis substrates such as 3-phenyl-1-butene, sulfonated 3-phenyl-1-butene, substituted 3-phenyl-1-butene, and sulfonated substituted 3-phenyl-1-butene include 5-decene, 6-dodecene, 7-teradecene, 8-hexadecene, 9-octadecene, 10-$C_{20}$, 11-$C_{22}$, 12-$C_{24}$, and 13-$C_{26}$.

Examples of the most preferred linear internal olefins that may be used for the cross metathesis with cross metathesis substrates such as 3-phenyl-1-butene, sulfonated 3-phenyl-1-butene, substituted 3-phenyl-1-butene, and sulfonated substituted 3-phenyl-1-butene include 8-hexadecene, 9-octadecene, 10-$C_{20}$.

The term "alpha olefin" as used herein refers to organic compounds which are terminal olefins or alkenes with a chemical formula RR'C=$CH_2$, where R and R' are each independently H, alkyl, aryl, heteroalkyl, heteroaryl, alkoxy, alkylene, alkenyl, alkenylene, alkynyl, alkynylene, aryloxy, alkaryl, or acyl and R and R' are not both H.

The alpha olefin may be a single compound or a mixture of compounds. The internal olefin may comprise a single alpha olefin or a plurality of alpha olefins. A mixture of alpha olefins may be used. The alpha olefin may be hydrophobic or hydrophilic, although in a preferred embodiment, the alpha olefin is hydrophobic.

The alpha olefin may be wherein one olefinic carbon is unsubstituted and the other olefinic carbon is substituted with one or two non-hydrogen substituents. The substituted olefinic carbon may therefore be mono-substituted or di-substituted.

The alpha olefin may comprise substituents selected from any of the substituents listed herein above. For example, the alpha olefin may comprises a substituent comprising 1 to about 20 carbon atoms, about 10 carbon atoms, or about 6 carbon atoms.

Examples of linear internal olefins that may be used for the cross-metathesis partner with substituted 3-phenyl-1-butene or sulfonated substituted 3-phenyl-1-butene to produce substituted 2-Ph*LAeB and sulfonated substituted 2-Ph*LAeS are shown in Scheme 12.

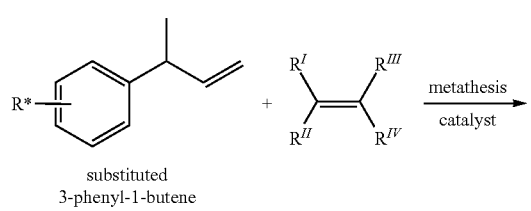

For example the alpha olefin may have the structure $H_2C=C(R^{IX})(R^X)$, wherein $R^{IX}$ and $R^X$ are independently selected from hydrogen, hydrocarbyl, substituted hydrocarbyl, heteroatom-containing hydrocarbyl, substituted heteroatom-containing hydrocarbyl and functional groups, provided that at least one of $R^{IX}$ and $R^X$ is a non-hydrogen substituent. Furthermore, $R^{IX}$ and $R^X$ may be linked to form a cycle. In a preferred embodiment, $R^{IX}$ and $R^X$ are independently selected from substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted heteroatom-containing $C_1$-$C_{20}$ alkyl, substituted or unsubstituted heteroatom-containing $C_2$-$C_{20}$ alkenyl, substituted or unsubstituted heteroatom-containing $C_2$-$C_{20}$ alkynyl, substituted or unsubstituted $C_5$-$C_{24}$ aryl, substituted or unsubstituted $C_5$-$C_{24}$ alkaryl, or substituted or unsubstituted $C_5$-$C_{24}$ aralkyl, substituted or unsubstituted heteroatom-containing $C_5$-$C_{24}$ aryl, substituted or unsubstituted heteroatom-containing $C_5$-$C_{24}$ alkaryl, substituted or unsubstituted heteroatom-containing $C_5$-$C_{24}$ aralkyl, and functional groups, with the proviso that when $R^{IX}$ equals $R^X$ $R^{IX}$ and $R^X$ are not equal hydrogen.

The term "linear alpha olefin" as used herein means an alpha olefin with a chemical formula $RR'C=CH_2$, where R is H or methyl and R' is a $C_2$ to $C_{19}$ alkyl group, where the carbon atoms in the alkyl chain may have only hydrogen atoms or a methyl group bonded to them.

Examples of linear alpha olefins that may be used for the cross metathesis reaction with alpha-methyl styrene (AMS) or sulfonated AMS to produce 2-PhLAeB and sulfonated 2-PhLAeB are shown in Scheme 13.

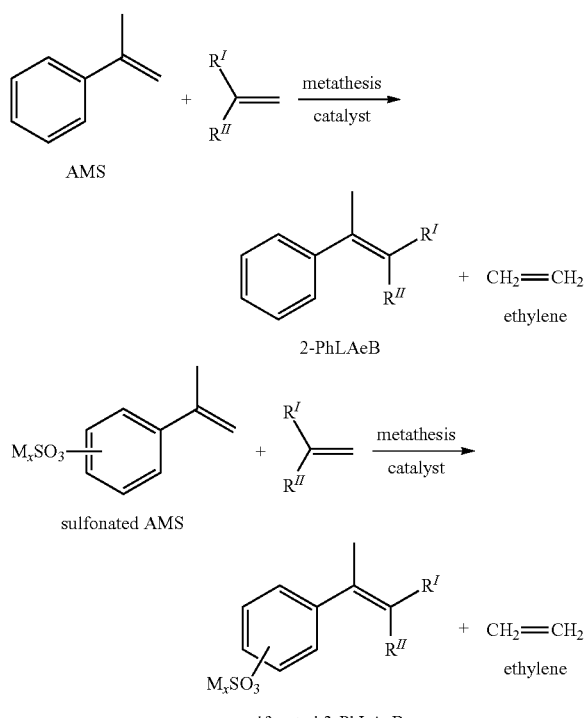

when $R^I$ is H and $R^{II}$ is $C_3$ to $C_{19}$ alkyl
$M_x$ = H, CH$_3$, NH$_4^+$, Li$^+$, Na$^+$, K$^+$, Cs$^+$, Mg$^{+2}$, Ca$^{+2}$, or Sr$^{+2}$ Examples of linear alpha olefins that may be used for the cross metathesis reaction with substituted alpha-methyl styrene (AM*S) or sulfonated substituted AM*S to produce substituted 2-Ph*LAeB and sulfonated substituted 2-Ph*LAeS are shown in Scheme 14.

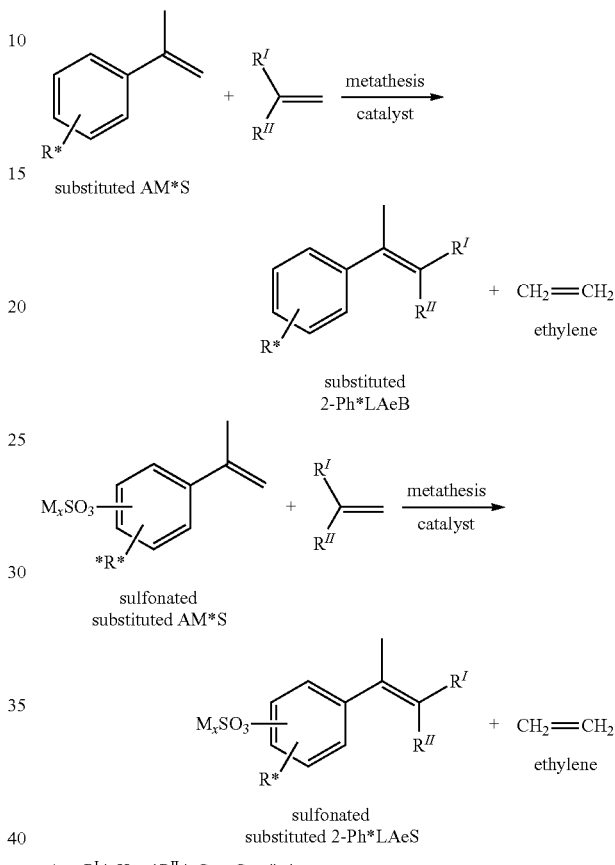

where $R^I$ is H and $R^{II}$ is $C_3$ to $C_{19}$ alkyl
$M_x$ = H, CH$_3$, NH$_4^+$, Li$^+$, Na$^+$, K$^+$, Cs$^+$, Mg$^{+2}$, Ca$^{+2}$, or Sr$^{+2}$ Examples of linear alpha olefins that may be used for the cross-metathesis with cross metathesis substrates such as alpha-methyl styrene, sulfonated alpha-methyl styrene, substituted alpha-methyl styrene, and sulfonated substituted alpha-methyl styrene include 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene.

Examples of preferred linear alpha olefins that may be used for the cross-metathesis with cross metathesis substrates such as alpha-methyl styrene, sulfonated alpha-methyl styrene, substituted alpha-methyl styrene, and sulfonated substituted alpha-methyl styrene include 1-hexene, 1-heptene, 1-octene, 1-nonene, 1-decene, 1-undecene, 1-dodecene, 1-tridecene, and 1-tetradecene.

Examples of preferred linear alpha olefins that may be used for the cross-metathesis with cross metathesis substrates such as alpha-methyl styrene, sulfonated alpha-methyl styrene, substituted alpha-methyl styrene, and sulfonated substituted alpha-methyl styrene include terpenes and related isoprenoids. Non-limiting examples of terpenes include alpha- or beta-farnesenes.

Examples of the most preferred linear alpha olefins that may be used for the cross-metathesis with cross metathesis substrates such as alpha-methyl styrene, sulfonated alpha-methyl styrene, substituted alpha-methyl styrene, and sulfonated substituted alpha-methyl styrene include 1-decene, 1-undecene and 1-dodecene.

Examples of linear alpha olefins that may be used for the cross metathesis reaction with 3-phenyl-1-butene or sulfonated 3-phenyl-1-butene to produce 2-PhLAeB and sulfonated 2-PhLAeB are shown in Scheme 15.

Scheme 15.
Cross metathesis of linear alpha olefins with
3-phenyl-1-butene or sulfonated 3-phenyl-1-butene.

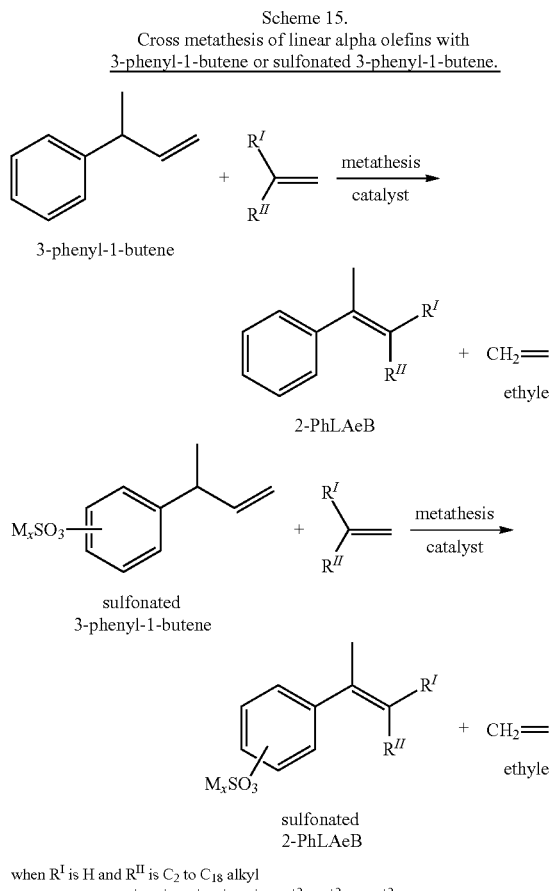

when $R^I$ is H and $R^{II}$ is $C_2$ to $C_{18}$ alkyl
$M_x$ = H, $CH_3$, $NH_4^+$, $Li^+$, $Na^+$, $K^+$, $Cs^+$, $Mg^{+2}$, $Ca^{+2}$, or $Sr^{+2}$ Examples of linear alpha olefins that may be used for the cross metathesis reaction with substituted 3-phenyl-1-butene or sulfonated substituted 3-phenyl-1-butene to produce substituted 2-Ph*LAeB and sulfonated substituted 2-Ph*LAeS are shown in Scheme 16.

Scheme 16.
Cross metathesis of linear alpha olefins with substituted
3-phenyl-1-butene or sulfonated substituted 3-phenyl-1-butene.

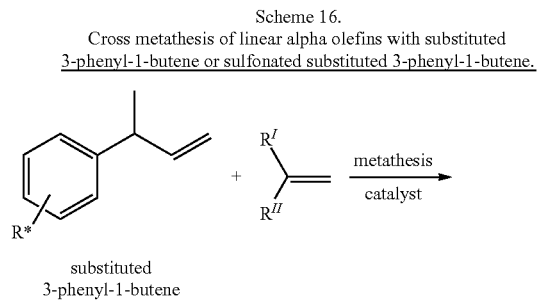

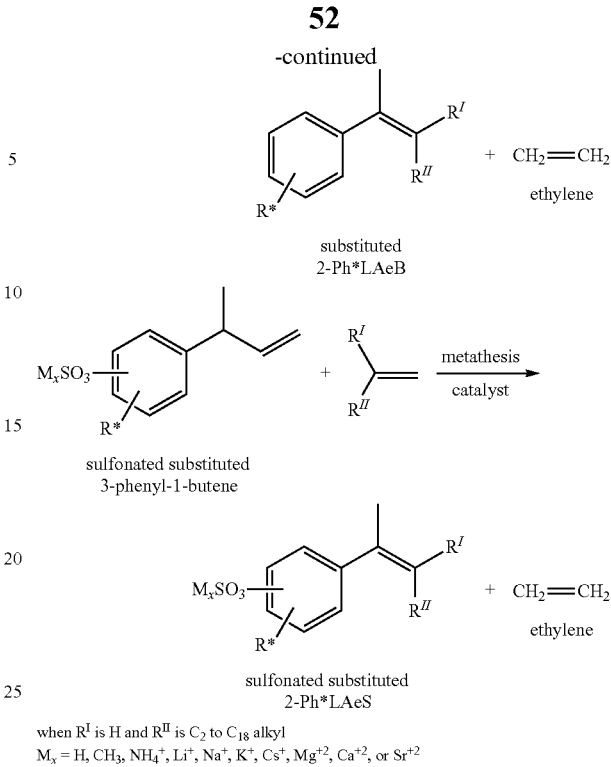

when $R^I$ is H and $R^{II}$ is $C_2$ to $C_{18}$ alkyl
$M_x$ = H, $CH_3$, $NH_4^+$, $Li^+$, $Na^+$, $K^+$, $Cs^+$, $Mg^{+2}$, $Ca^{+2}$, or $Sr^{+2}$ Examples of linear alpha olefins that may be used for the cross-metathesis with cross metathesis substrates such as 3-phenyl-1-butene, sulfonated 3-phenyl-1-butene, substituted 3-phenyl-1-butene, and sulfonated substituted 3-phenyl-1-butene include 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene.

Examples of preferred linear alpha olefins that may be used for the cross-metathesis with cross metathesis substrates such as 3-phenyl-1-butene, sulfonated 3-phenyl-1-butene, substituted 3-phenyl-1-butene, and sulfonated substituted 3-phenyl-1-butene include 1-hexene, 1-heptene, 1-octene, 1-nonene, 1-decene, 1-undecene, 1-dodecene, 1-tridecene, and 1-tetradecene.

Examples of the most preferred linear alpha olefins that may be used for the cross-metathesis with cross metathesis substrates such as 3-phenyl-1-butene, sulfonated 3-phenyl-1-butene, substituted 3-phenyl-1-butene, and sulfonated substituted 3-phenyl-1-butene include 1-nonene, 1-decene, and 1-undecene.

Methyl groups on the alkene backbone may improve solubility of PhLAS, examples of methyl substituted linear alpha olefins that may be used for the cross-metathesis with cross metathesis substrates such as alpha-methyl styrene, sulfonated alpha-methyl styrene, substituted alpha-methyl styrene, sulfonated substituted alpha-methyl styrene, 3-phenyl-1-butene, sulfonated 3-phenyl-1-butene, substituted 3-phenyl-1-butene, or sulfonated substituted 3-phenyl-1-butene include 3-methylbut-1-ene, 3-methylpent-1-ene, 4-methylpent-1-ene, 3-methylhex-1-ene, 4-methylhex-1-ene, 5-methylhex-1-ene, 3-methylhept-1-ene, 4-methylhept-1-ene, 5-methylhept-1-ene, 6-methylhept-1-ene, 3-methyloct-1-ene, 4-methyloct-1-ene, 5-methyloct-1-ene, 6-methyloct-1-ene, 7-methyloct-1-ene, 3-methylnon-1-ene, 4-methylnon-1-ene, 5-methylnon-1-ene, 6-methylnon-1-ene, 7-methylnon-1-ene, 8-methylnon-1-ene, 3-methyldec- 1-ene, 4-methyldec-1-ene, 5-methyldec-1-ene, 6-methyldec-1-ene, 7-methyldec-1-ene, 8-methyldec-1-ene, 9-methyldec-1-ene, 3-methylundec-1-ene, 4-methylundec-1-ene, 5-methylundec-1-ene, 6-methylundec-1-ene, 7-methylundec-1-ene, 8-methylundec-1-ene, 9-methylundec-1-ene, 10-methylundec-1-ene, 3-methyldodec-1-ene, 4-methyldodec-1-ene, 5-methyldodec-1-ene, 6-methyldodec-1-ene, 7-methyldodec-1-ene, 8-methyldodec-1-ene, 9-methyldodec-1-ene, 10-methyldodec-1-ene, 11-methyldodec-1-ene, 3-methyltridec-1-ene, 4-methyltridec-1-ene, 5-methyltridec-1-ene, 6-methyltridec-1-ene, 7-methyltridec-1-ene, 8-methyltridec-1-ene, 9-methyltridec-1-ene, 10-methyltridec-1-ene, 11-methyltridec-1-ene, 12-methyltridec-1-ene, 3-methyltetradec-1-ene, 4-methyltetradec-1-ene, 5-methyltetradec-1-ene, 6-methyltetradec-1-ene, 7-methyltetradec-1-ene, 8-methyltetradec-1-ene, 9-methyltetradec-1-ene, 10-methyltetradec-1-ene, 11-methyltetradec-1-ene, 12-methyltetradec-1-ene, and 13-methyltetradec-1-ene.

More preferred examples of methyl substituted linear alpha olefins that may be used for the cross-metathesis with cross metathesis substrates such as alpha-methyl styrene, sulfonated alpha-methyl styrene, substituted alpha-methyl styrene, sulfonated substituted alpha-methyl styrene, 3-phenyl-1-butene, sulfonated 3-phenyl-1-butene, substituted 3-phenyl-1-butene, or sulfonated substituted 3-phenyl-1-butene include 3-methylnon-1-ene, 4-methylnon-1-ene, 5-methylnon-1-ene, 6-methylnon-1-ene, 7-methylnon-1-ene, 8-methylnon-1-ene, 3-methyldec-1-ene, 4-methyldec-1-ene, 5-methyldec-1-ene, 6-methyldec-1-ene, 7-methyldec-1-ene, 8-methyldec-1-ene, 9-methyldec-1-ene, 3-methylundec-1-ene, 4-methylundec-1-ene, 5-methylundec-1-ene, 6-methylundec-1-ene, 7-methylundec-1-ene, 8-methylundec-1-ene, 9-methylundec-1-ene, 10-methylundec-1-ene, 3-methyldodec-1-ene, 4-methyldodec-1-ene, 5-methyldodec-1-ene, 6-methyldodec-1-ene, 7-methyldodec-1-ene, 8-methyldodec-1-ene, 9-methyldodec-1-ene, 10-methyldodec-1-ene, 11-methyldodec-1-ene, 3-methyltridec-1-ene, 4-methyltridec-1-ene, 5-methyltridec-1-ene, 6-methyltridec-1-ene, 7-methyltridec-1-ene, 8-methyltridec-1-ene, 9-methyltridec-1-ene, 10-methyltridec-1-ene, 11-methyltridec-1-ene, 12-methyltridec-1-ene, 3-methyltetradec-1-ene, 4-methyltetradec-1-ene, 5-methyltetradec-1-ene, 6-methyltetradec-1-ene, 7-methyltetradec-1-ene, 8-methyltetradec-1-ene, 9-methyltetradec-1-ene, 10-methyltetradec-1-ene, 11-methyltetradec-1-ene, 12-methyltetradec-1-ene, and 13-methyltetradec-1-ene.

Most preferred examples of methyl substituted linear alpha olefins that may be used for the cross-metathesis with cross metathesis substrates such as alpha-methyl styrene, sulfonated alpha-methyl styrene, substituted alpha-methyl styrene, sulfonated substituted alpha-methyl styrene, 3-phenyl-1-butene, sulfonated 3-phenyl-1-butene, substituted 3-phenyl-1-butene, or sulfonated substituted 3-phenyl-1-butene include 3-methylnon-1-ene, 4-methylnon-1-ene, 5-methylnon-1-ene, 6-methylnon-1-ene, 7-methylnon-1-ene, 8-methylnon-1-ene, 3-methyldec-1-ene, 4-methyldec-1-ene, 5-methyldec-1-ene, 6-methyldec-1-ene, 7-methyldec-1-ene, 8-methyldec-1-ene, 9-methyldec-1-ene, 3-methylundec-1-ene, 4-methylundec-1-ene, 5-methylundec-1-ene, 6-methylundec-1-ene, 7-methylundec-1-ene, 8-methylundec-1-ene, 9-methylundec-1-ene, 10-methylundec-1-ene, 3-methyldodec-1-ene, 4-methyldodec-1-ene, 5-methyldodec-1-ene, 6-methyldodec-1-ene, 7-methyldodec-1-ene, 8-methyldodec-1-ene, 9-methyldodec-1-ene, 10-methyldodec-1-ene, and 11-methyldodec-1-ene.

Methyl groups on the alkene backbone improves solubility of PhLAS, examples of dimethyl substituted linear internal olefins that may be used for the cross metathesis with cross metathesis substrates such as alpha-methyl styrene, sulfonated alpha-methyl styrene, substituted alpha-methyl styrene, or sulfonated substituted alpha-methyl styrene, 3-phenyl-1-butene, sulfonated 3-phenyl-1-butene, substituted 3-phenyl-1-butene, sulfonated substituted 3-phenyl-1-butene include the self-metathesized methyl substituted linear alpha olefins, listed earlier, to yield symmetrical dimethyl linear internal olefins.

Examples of symmetrical dimethyl substituted linear internal olefins produced by self-metathesis of methyl substituted alpha olefins include 3-methylpent-1-ene to yield 3,6-dimethyl-4-octene, 4-methylpent-1-ene to yield 2,7-dimethyl-4-octene, 3-methylhex-1-ene to yield 4,7-dimethyl-5-decene, etc.

Examples of symmetrical dimethyl substituted linear internal olefins that may be used for the cross metathesis with cross metathesis substrates such as 3-phenyl-1-butene, sulfonated 3-phenyl-1-butene, substituted 3-phenyl-1-butene, or sulfonated substituted 3-phenyl-1-butene include dimethyl 3-hexene, dimethyl 4-octene, dimethyl 5-decene, dimethyl 6-dodecene, dimethyl 7-teradecene, dimethyl 8-hexadecene, dimethyl 9-octadecene, dimethyl 10-$C_{20}$, dimethyl 11-$C_{22}$, dimethyl 12-$C_{24}$, dimethyl 13-$C_{26}$, dimethyl 14-$C_{28}$, dimethyl 15-$C_{30}$, dimethyl 16-$C_{32}$, dimethyl 17-$C_{34}$, dimethyl 18-$C_{36}$, dimethyl 19-$C_{38}$, and dimethyl 20-$C_{40}$.

More preferred examples of symmetrical dimethyl substituted linear internal olefins that may be used for the cross metathesis with cross metathesis substrates such as 3-phenyl-1-butene, sulfonated 3-phenyl-1-butene, substituted 3-phenyl-1-butene, or sulfonated substituted 3-phenyl-1-butene include dimethyl 7-tetradecene, dimethyl 8-hexadecene, dimethyl 9-octadecene, dimethyl 10-$C_{20}$, dimethyl 11-$C_{22}$, dimethyl 12-$C_{24}$, and dimethyl 13-$C_{26}$.

Most preferred examples of symmetrical dimethyl substituted linear internal olefins that may be used for the cross metathesis with cross metathesis substrates such as 3-phenyl-1-butene, sulfonated 3-phenyl-1-butene, substituted 3-phenyl-1-butene, or sulfonated substituted 3-phenyl-1-butene include dimethyl 7-tetradecene, dimethyl 8-hexadecene, dimethyl 9-octadecene, dimethyl 10-$C_{20}$, and dimethyl 11-$C_{22}$.

It will be appreciated by those of skill in the art that the use of a mixture of alpha olefins subjected to cross-metathesis conditions may yield a mixture of internal olefins. It will be appreciated by those of skill in the art that the use of a mixture of linear alpha olefins subjected to cross metathesis conditions may yield a mixture of linear internal olefins. For example, a mixture of 1-nonene, 1-decene, and 1-undecene subjected to cross-metathesis conditions will yield a mixture of 8-hexadecene (8-$C_{16}$), 8-heptadecene (8-$C_{17}$), 8-octadecene (8-$C_{18}$), 9-octadecene (9-$C_{18}$), 9-nonadecene (9-$C_{19}$) and 10-eicosene (10-$C_{20}$).

Therefore any mixture of alpha olefins and branched alpha olefins, di-substituted and branched di-substituted olefin may be used. Therefore, any mixture of linear alpha olefins, methyl substituted linear alpha olefins, linear internal olefins, methyl substituted linear internal olefins, etc. may be used.

Examples of 2-phenyl linear alkene benzenes include 2-phenyl-2-hexene, 2-phenyl-3-hexene, 2-phenyl-2-heptene, 2-phenyl-3-heptene, 2-phenyl-2-octene, 2-phenyl-3-octene, 2-phenyl-2-nonene, 2-phenyl-3-nonene, 2-phenyl-2-decene, 2-phenyl-3-decene, 2-phenyl-2-undecene, 2-phenyl-3-undecene, 2-phenyl-2-dodecene, 2-phenyl-3-dodecene, 2-phenyl-2-tridecene, 2-phenyl-3-tridecene, 2-phenyl-2-tetradecene, 2-phenyl-3-tetradecene, 2-phenyl-2-pentadecene, 2-phenyl-3-pentadecene, 2-phenyl-2-hexadecene, 2-phenyl-3-hexadecene, 2-phenyl-2-heptadecene, 2-phenyl-3-heptadecene, 2-phenyl-2-octadecene, 2-phenyl-3-octadecene, 2-phenyl-2-nonadecene, 2-phenyl-3-nonadecene, 2-phenyl-2-eicosene, and 2-phenyl-3-eicosene.

Examples of the more preferred 2-phenyl linear alkene benzenes include 2-phenyl-2-octene, 2-phenyl-3-octene, 2-phenyl-2-nonene, 2-phenyl-3-nonene, 2-phenyl-2-decene, 2-phenyl-3-decene, 2-phenyl-2-undecene, 2-phenyl-3-undecene, 2-phenyl-2-dodecene, 2-phenyl-3-dodecene, 2-phenyl-2-tridecene and 2-phenyl-3-tridecene.

Examples of the most preferred 2-phenyl linear alkene benzenes include 2-phenyl-2-undecene, 2-phenyl-2-dodecene, 2-phenyl-2-tridecene, 2-phenyl-3-undecene, 2-phenyl-3-dodecene, and 2-phenyl-3-tridecene.

Examples of substituted 2-phenyl linear alkene benzenes, where the benzene ring is substituted with one or more groups designated R*, include substituted 2-phenyl-2-hexene, substituted 2-phenyl-3-hexene, substituted 2-phenyl-2-heptene, substituted 2-phenyl-3-heptene, substituted 2-phenyl-2-octene, substituted 2-phenyl-3-octene, substituted 2-phenyl-2-nonene, substituted 2-phenyl-3-nonene, substituted 2-phenyl-2-decene, substituted 2-phenyl-3-decene, substituted 2-phenyl-2-undecene, substituted 2-phenyl-3-undecene, substituted 2-phenyl-2-dodecene, substituted 2-phenyl-3-dodecene, substituted 2-phenyl-2-tridecene, substituted 2-phenyl-3-tridecene, substituted 2-phenyl-2-tetradecene, substituted 2-phenyl-3-tetradecene, substituted 2-phenyl-2-pentadecene, substituted 2-phenyl-3-pentadecene, substituted 2-phenyl-2-hexadecene, substituted 2-phenyl-3-hexadecene, substituted 2-phenyl-2-heptadecene, substituted 2-phenyl-3-heptadecene, substituted 2-phenyl-2-octadecene, substituted 2-phenyl-3-octadecene, substituted 2-phenyl-2-nonadecene, substituted 2-phenyl-3-nonadecene, substituted 2-phenyl-2-eicosene, and substituted 2-phenyl-3-eicosene.

Examples of the more preferred substituted 2-phenyl linear alkene benzenes, where the benzene ring is substituted with one or more groups designated R*, include substituted 2-phenyl-2-octene, substituted 2-phenyl-3-octene, substituted 2-phenyl-2-nonene, substituted 2-phenyl-3-nonene, substituted 2-phenyl-2-decene, substituted 2-phenyl-3-decene, substituted 2-phenyl-2-undecene, substituted 2-phenyl-3-undecene, substituted 2-phenyl-2-dodecene, substituted 2-phenyl-3-dodecene, substituted 2-phenyl-2-tridecene and substituted 2-phenyl-3-tridecene.

Examples of the most preferred substituted 2-phenyl linear alkene benzenes, where the benzene ring is substituted with one or more groups designated R*, include substituted 2-phenyl-2-undecene, substituted 2-phenyl-2-dodecene, substituted 2-phenyl-2-tridecene, substituted 2-phenyl-3-undecene, substituted 2-phenyl-3-dodecene, and substituted 2-phenyl-3-tridecene.

Examples of 2-PhLABs following hydrogenation are 2-phenyl-pentane, 2-phenyl-hexane, 2-phenyl-heptane, 2-phenyl-octane, 2-phenyl-nonane, 2-phenyl-decane, 2-phenyl-undecane, 2-phenyl-dodecane, 2-phenyl-tridecane, 2-phenyl-tetradecane, 2-phenyl-pentadecane, 2-phenyl-hexadecane, 2-phenyl-heptadecane, 2-phenyl-octadecane, 2-phenyl-nonadecane, and 2-phenyl-eicosane.

Examples of the more preferred 2-PhLABs following hydrogenation are 2-phenyl-octane, 2-phenyl-nonane, 2-phenyl-decane, 2-phenyl-undecane, 2-phenyl-dodecane, and 2-phenyl-tridecane.

Examples of the most preferred 2-PhLABs following hydrogenation are 2-phenyl-undecane, 2-phenyl-dodecane, and 2-phenyl-tridecane.

Examples of 2-Ph*LABs following hydrogenation are substituted 2-phenyl-pentane, substituted 2-phenyl-hexane, substituted 2-phenyl-heptane, substituted 2-phenyl-octane, substituted 2-phenyl-nonane, substituted 2-phenyl-decane, substituted 2-phenyl-undecane, substituted 2-phenyl-dodecane, substituted 2-phenyl-tridecane, substituted 2-phenyl-tetradecane, substituted 2-phenyl-pentadecane, substituted 2-phenyl-hexadecane, substituted 2-phenyl-heptadecane, substituted 2-phenyl-octadecane, substituted 2-phenyl-nonadecane, and substituted 2-phenyl-eicosane.

Examples of the more preferred 2-Ph*LABs following hydrogenation are substituted 2-phenyl-octane, substituted 2-phenyl-nonane, substituted 2-phenyl-decane, substituted 2-phenyl-undecane, substituted 2-phenyl-dodecane, and substituted 2-phenyl-tridecane.

Examples of the most preferred 2-Ph*LABs following hydrogenation are substituted 2-phenyl-undecane, substituted 2-phenyl-dodecane, and substituted 2-phenyl-tridecane.

It will be appreciated by those of skill in the art that the methods described herein are not limited to making 2-phenyl linear alkene benzenes, 2-phenyl linear alkene benzene sulfonates, 2-phenyl linear alkylbenzenes, 2-phenyl linear alkyl benzene sulfonates, substituted 2-phenyl linear alkene benzenes, substituted 2-phenyl linear alkene benzene sulfonates, substituted 2-phenyl linear alkylbenzenes, and substituted 2-phenyl linear alkyl benzene sulfonates. Other alkene benzenes, alkylbenzenes, alkene benzene sulfonates, and alkyl benzene sulfonates may also be prepared by the methods described herein including without limitation alkene benzenes, functionalized alkene benzenes, branched alkene benzenes, substituted and non-substituted alkene benzenes, alkene benzene sulfonates, functionalized alkene benzene sulfonates, branched alkene benzene sulfonates, substituted and non-substituted alkene benzene sulfonates, alkylbenzenes, functionalized alkyl benzenes, branched alkylbenzenes, substituted and non-substituted alkylbenzenes, linear alkylbenzenes, functionalized linear alkyl benzenes, branched alkylbenzenes, substituted and non-substituted linear alkylbenzenes, functionalized alkyl benzene sulfonates, branched alkylbenzene sulfonates, substituted and non-substituted alkylbenzene sulfonates, linear alkylbenzene sulfonates, functionalized linear alkylbenzene sulfonates linear alkylbenzene sulfonates, substituted and non-substituted linear alkylbenzene sulfonates.

It will be appreciated by those of skill in the art that the use of olefinic substrates containing, for example, long alkyl substituents enables liquid-phase, room temperature (or greater) reactions and/or the use of reactors working at near atmospheric or slightly higher pressures.

In some preferred embodiments, the cross metathesis substrate is soluble in the olefinic substrate. The cross metathesis substrate may have a solubility of at least 0.25 M, at least 1 M, at least 3 M, or at least 5 M in the olefinic substrate. The cross metathesis substrate and the olefinic substrate may also be miscible at all concentrations.

As another example, the cross metathesis substrate has a low solubility in the olefinic substrate, and the cross metathesis reaction occurs as an interfacial reaction. It should be noted that, when one or more of the reactants is solid or gaseous, the reactions may still be carried out in the liquid phase by dissolving any solid or gaseous reactants in the liquid reactants, or by employing a solvent, as described herein.

The olefinic substrate and/or cross metathesis substrate may be provided in the form of a gas. Typically, the pressure of a gaseous cross-metathesis partner over the reaction solution is maintained in a range that has a minimum of about 10 psig, 15 psig, 50 psig, or 80 psig, and a maximum of about 250 psig, 200 psig, 150 psig, or 130 psig. Embodiments wherein the reaction pressures are lowered till near atmospheric pressure and in particular till pressures slightly above atmospheric allow for a reduction in equipment costs compared to embodiments performed at high pressure (e.g., pressures greater than 250 psi).

The olefin metathesis reactions (e.g. cross metathesis) of the disclosure are catalyzed by any of the metathesis catalysts that are described herein. The catalyst is typically added to the reaction medium as a solid, but may also be added as a solution wherein the catalyst is dissolved in an appropriate solvent. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or $$\text{ppm catalyst} = \frac{\text{moles catalyst}}{\text{moles olefinic substrate double bonds}} * 1{,}000{,}000$$

1000 ppm relative to the amount of the olefinic substrate. Catalyst loading, when measured in ppm relative to the amount of the olefinic substrate, is calculated using the equation Alternatively, the amount of catalyst can be measured in terms of mol % relative to the amount of olefinic substrate, using the equation $$\text{mol \% catalyst} = \frac{\text{moles catalyst}}{\text{moles olefinic substrate double bonds}} * 100$$

Thus, the catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

In a preferred embodiment, the reactions of the disclosure are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions of the disclosure may also be carried out in an oxygen-containing and/or a water-containing atmosphere, and in one embodiment, the reactions are carried out under ambient conditions. The presence of oxygen, water, or other impurities in the reaction may, however, necessitate the use of higher catalyst loadings as compared with reactions performed under an inert atmosphere.

In another preferred embodiment, the reactions of this invention can be run as to be completely atom efficient. For example, in the alpha olefin self-metathesis reaction to yield an internal olefin, the ethylene generated can be used in the hydrovinylation reaction to yield 3-phenyl-1-butene. Internal olefin cross metathesis with 3-phenyl-1-butene will yield 2-PhLAeB and an alpha olefin or ethylene. The alpha olefin is recycled back into the internal olefin reaction, as shown in Scheme 17. One skilled in the art can appreciate that in each step by-products may be form which can be recycled at the appropriate step, i.e. in III. Cross Metathesis Reaction, two 2-PhLAeB and ethylene may be formed; the ethylene is used in II. Hydrovinylation Reaction. The net result is no wasted carbon atoms in this invention.

Scheme 17.
Atom efficiency of this invention.

I. Alpha-Olefin (AO) to Internal Olefin (IO) Reaction

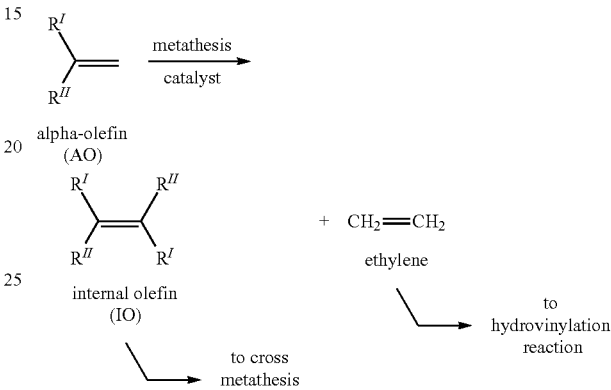

II. Hydrovinylation Reaction

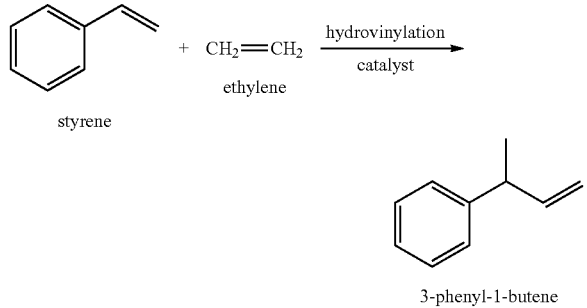

III. Cross Metathesis Reaction

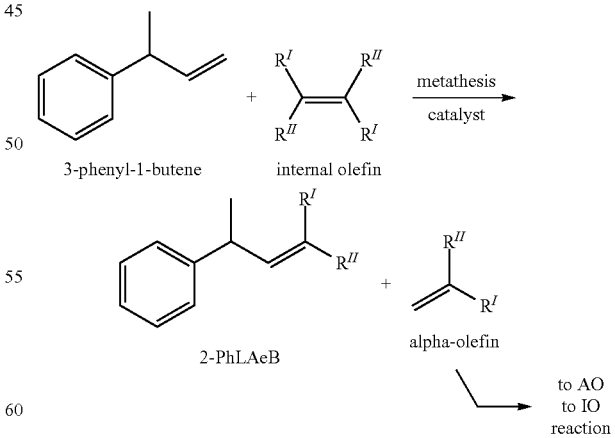

when $R^I$ is H and $R^{II}$ is $C_2$ to $C_{18}$ alkyl

In another preferred embodiment, the reactions of this invention can be run as to be completely atom efficient. For example, in the alpha olefin self-metathesis reaction to yield an internal olefin, the ethylene generated can be used in the hydrovinylation reaction to yield substituted 3-phenyl-1-butene. Internal olefin cross metathesis with substituted 3-phenyl-1-butene will yield 2-Ph*LAeB and an alpha olefin or ethylene. The alpha olefin is recycled back into the internal olefin reaction, as shown in Scheme 18. One skilled in the art can appreciate that in each step by-products may be form which can be recycled at the appropriate step, i.e. in III. Cross Metathesis Reaction, two 2-Ph*LAeB and ethylene may be formed; the ethylene is used in II. Hydrovinylation Reaction. The net result is no wasted carbon atoms in this invention.

Scheme 18.
Atom efficiency of this invention.

I. Alpha-Olefin (AO) to Internal Olefin (IO) Reaction

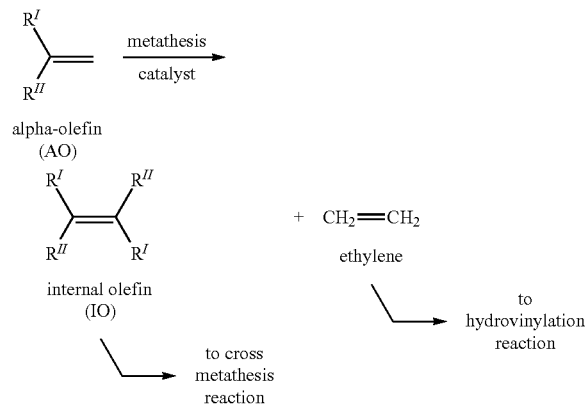

II. Hydrovinylation Reaction

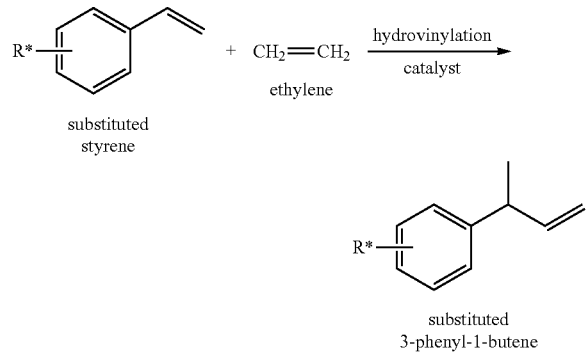

III. Cross Metathesis Reaction

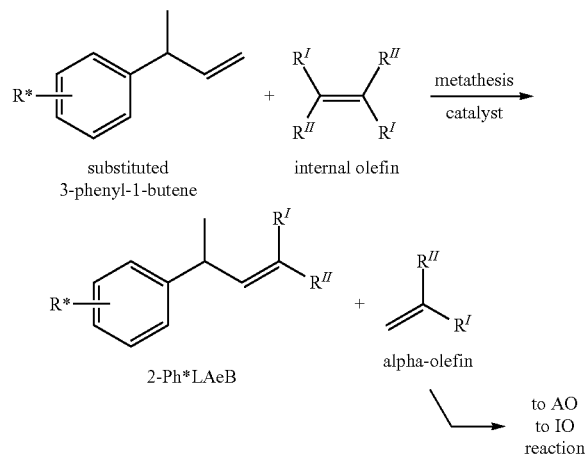

when $R^I$ is H and $R^{II}$ is $C_2$ to $C_{18}$ alkyl

Olefin Metathesis Catalyst

This invention is useful for the synthesis of high purity 2-PhLAB and high purity 2-Ph*LAB by any suitable olefin metathesis catalyst. Such metathesis reactions are not specifically limited, and include cross metathesis (CM), self-metathesis, ethenolysis, alkenolysis, and combinations thereof.

An Olefin metathesis catalyst according to the invention, is preferably a Group 8 transition metal complex having the structure of formula (I)

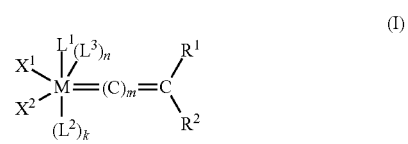

(I)

in which:
M is a Group 8 transition metal;
$L^1$, $L^2$, and $L^3$ are neutral electron donor ligands;
n is 0 or 1, such that $L^3$ may or may not be present;
m is 0, 1, or 2;
k is 0 or 1;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Additionally, in formula (I), one or both of $R^1$ and $R^2$ may have the structure $—(W)_n—U^+V^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1. Furthermore, $R^1$ and $R^2$ may be taken together to form an indenylidene moiety.

Preferred catalysts contain Ru or Os as the Group 8 transition metal, with Ru particularly preferred.

Numerous embodiments of the catalysts useful in the reactions disclosed herein are described in more detail infra. For the sake of convenience, the catalysts are described in groups, but it should be emphasized that these groups are not meant to be limiting in any way. That is, any of the catalysts useful in the invention may fit the description of more than one of the groups described herein.

A first group of catalysts, then, are commonly referred to as First Generation Grubbs-type catalysts, and have the structure of formula (I). For the first group of catalysts, M is a Group 8 transition metal, m is 0, 1, or 2, and n, k, $X^1$, $X^2$, $L^1$, $L^2$, $L^3$, $R^1$ and $R^2$ are described as follows.

For the first group of catalysts, n is 0 or 1, k is 0 or 1, and $L^1$ and $L^2$ are independently selected from phosphine, sulfonated phosphine, phosphite, phosphinite, phosphonite, arsine, stibine, ether, (including cyclic ethers), amine, amide, imine, sulfoxide, carboxyl, nitrosyl, pyridine, substituted pyridine, imidazole, substituted imidazole, pyrazine, substituted pyrazine and thioether. Exemplary ligands are trisubstituted phosphines. Preferred trisubstituted phosphines are of the formula $PR^{H1}R^{H2}R^{H3}$, where $R^{H1}$, $R^{H2}$, and $R^{H3}$ are each independently substituted or unsubstituted aryl or $C_1$-$C_{10}$ alkyl, particularly primary alkyl, secondary alkyl, or cycloalkyl. In the most preferred, $L^1$ and $L^2$ are independently selected from the group consisting of trimethylphosphine ($PMe_3$), triethylphosphine ($PEt_3$), tri-n-butylphosphine ($PBu_3$), tri(ortho-tolyl)phosphine (P-o-tolyl$_3$), tri-tert-butylphosphine (P-tert-Bu$_3$), tri-sec-butylphosphine, tricyclopentylphosphine ($PCp_3$), tricyclohexylphosphine ($PCy_3$), triisopropylphosphine (P-i-Pr$_3$), trioctylphosphine ($POct_3$), triisobutylphosphine, (P-i-Bu$_3$), triphenylphosphine ($PPh_3$), tri(pentafluorophenyl)phosphine (P($C_6F_5$)$_3$), methyldiphenylphosphine ($PMePh_2$), dimethylphenylphosphine ($PMe_2Ph$), and diethylphenylphosphine ($PEt_2Ph$).

Alternatively, $L^1$ and $L^2$ may be independently selected from phosphabicycloalkane (e.g. monosubstituted 9-phosphabicyclo-[3.3.1]nonane, or monosubstituted 9-phosphabicyclo[4.2.1]nonane] such as cyclohexylphoban, isopropylphoban, ethylphoban, methylphoban, butylphoban, pentylphoban and the like).

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, $NO_3$, —N=C=O, —N=C=S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate ($CF_3SO_3$ or commonly abbreviated as OTf). In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —CH=C(CH$_3$)$_2$.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940, the disclosure of which is incorporated herein by reference. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as Second Generation Grubbs-type catalysts, have the structure of formula (I), wherein $L^1$ is a carbene ligand having the structure of formula (II)

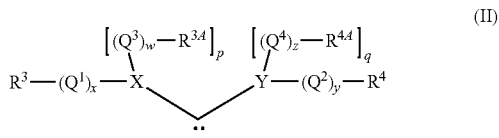

such that the complex may have the structure of formula (III)

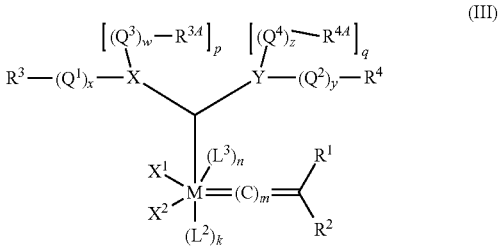

wherein M, m, n, k, $X^1$, $X^2$, $L^2$, $L^3$, $R^1$, and $R^2$ are as defined for the first group of catalysts, and the remaining substituents are as follows;

X and Y are heteroatoms typically selected from N, O, S, and P. Since O and S are divalent, p is necessarily zero when X is O or S, q is necessarily zero when Y is O or S. However, when X is N or P, then p is 1, and when Y is N or P, then q is 1. In a preferred embodiment, both X and Y are N;

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form a cyclic group; and $R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl. In addition, X and Y may be independently selected from carbon and one of the heteroatoms mentioned above, preferably no more than one of X or Y is carbon. Also, $L^2$ and $L^3$ may be taken together to form a single bidentate electron-donating ligand. Furthermore, $R^1$ and $R^2$ may be taken together to form an indenylidene moiety. Moreover, $X^1$, $X^2$, $L^2$, $L^3$, X and Y may be further coordinated to boron or to a carboxylate.

In addition, any two or more of $X^1$, $X^2$, $L^1$, $L^2$, $L^3$, $R^1$, $R^2$, $R^3$, $R^{3A}$, $R^4$, $R^{4A}$, $Q^1$, $Q^2$, $R^3$ and $Q^4$ can be taken together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support. Any two or more of $X^1$, $X^2$, $L^1$, $L^2$, $L^3$, $R^1$, $R^2$, $R^3$, $R^{3A}$, $R^4$, and $R^{4A}$ can also be taken to be -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or together to form a cyclic group, and any one or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to a support.

A particular class of carbene ligands having the structure of formula (II), where $R^{3A}$ and $R^{4A}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC) ligands.

Preferably, $R^{3A}$ and $R^{4A}$ are linked to form a cyclic group so that the carbene ligand has the structure of formula (IV)

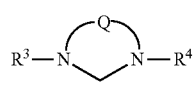

(IV)

wherein $R^3$ and $R^4$ are as defined for the second group of catalysts above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although not necessarily, a two-atom linkage or a three-atom linkage.

Examples of N-heterocyclic carbene (NHC) ligands and acyclic diaminocarbene ligands suitable as $L^1$ thus include, but are not limited to, the following where DIPP or DiPP is diisopropylphenyl and Mes is 2,4,6-trimethylphenyl:

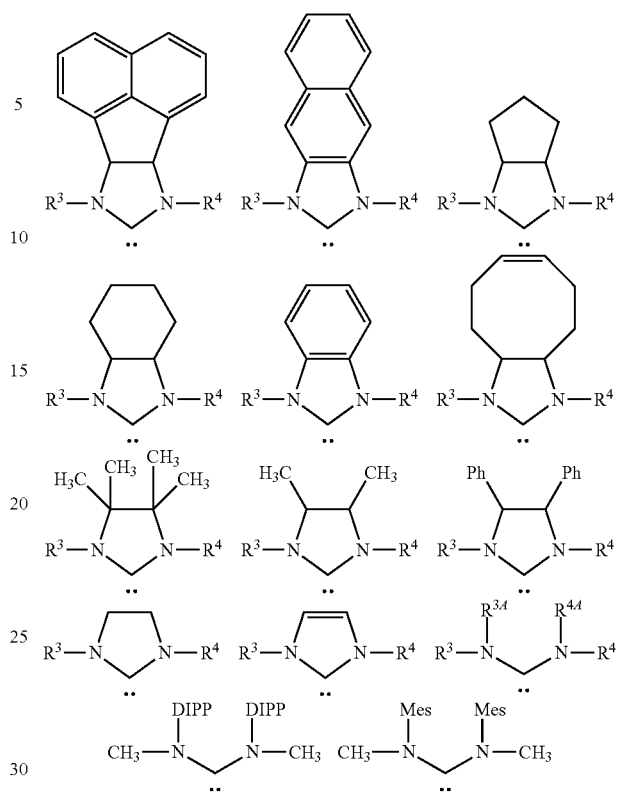

Additional examples of N-heterocyclic carbene (NHC) ligands and acyclic diaminocarbene ligands suitable as $L^1$ thus include, but are not limited to the following:

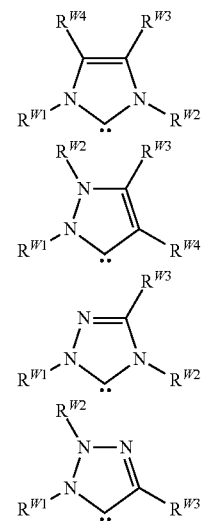

wherein $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be in independently selected from halogen, nitro, amido, carboxyl, alkoxy, aryloxy, sulfonyl, carbonyl, thio, or nitroso groups.

Additional examples of N-heterocyclic carbene (NHC) ligands suitable as $L^1$ are further described in U.S. Pat. Nos.

7,378,528; 7,652,145; 7,294,717; 6,787,620; 6,635,768; and 6,552,139 the contents of each are incorporated herein by reference.

Additionally, thermally activated N-Heterocyclic Carbene Precursors as disclosed in U.S. Pat. No. 6,838,489, the contents of which are incorporated herein by reference, may also be used with the present invention.

When M is ruthenium, then, the preferred complexes have the structure of formula (V)

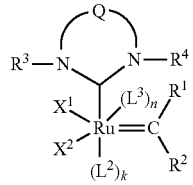

(V)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$ and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include, without limitation, carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers. Additionally, $R^3$ and $R^4$ may be unsubstituted phenyl or phenyl substituted with one or more substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Furthermore, $X^1$ and $X^2$ may be halogen.

When $R^3$ and $R^4$ are aromatic, they are typically, although not necessarily, composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl (i.e. Mes as defined herein).

In a third group of catalysts having the structure of formula (I), M, m, n, k, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole. Additionally, the nitrogen-containing heterocycles may be optionally substituted on a non-coordinating heteroatom with a non-hydrogen substituent.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl),N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In certain embodiments, $L^2$ and $L^3$ may also be taken together to form a bidentate or multidentate ligand containing two or more, generally two, coordinating heteroatoms such as N, O, S, or P, with preferred such ligands being diimine ligands. One representative bidentate ligand has the structure of formula (VI)

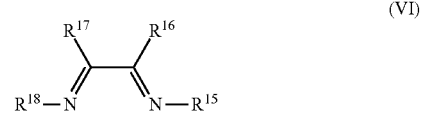

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, L', $L^2$, $L^3$, R', and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein Y is coordinated to the metal are examples of a fifth group of catalysts, and are commonly called "Grubbs-Hoveyda" catalysts. Grubbs-Hoveyda metathesis-active metal carbene complexes may be described by the formula (VII)

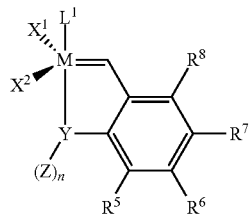

(VII)

wherein,

M is a Group 8 transition metal, particularly Ru or Os, or, more particularly, Ru;

$X^1$, $X^2$, and $L^1$ are as previously defined herein for the first and second groups of catalysts;

Y is a heteroatom selected from nil, N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, amino sulfonyl, mono alkylamino sulfonyl, dialkylaminosulfonyl, alkylsulfonyl, nitrile, nitro, alkylsulfinyl, trihalo alkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein "A" and Fn have been defined above; and any combination of Y, Z, $R^5$, $R^6$, $R^7$, and $R^8$ can be linked to form one or more cyclic groups;

n is 0, 1, or 2, such that n is 1 for the divalent heteroatoms O or S, and n is 2 for the trivalent heteroatoms N or P; and Z is a group selected from hydrogen, alkyl, aryl, functionalized alkyl, functionalized aryl where the functional group(s) may independently be one or more or the following: halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $X^2$, $L^1$, Y, Z, $R^5$, $R^6$, $R^7$, and $R^8$ may be linked to a support. Additionally, $R^5$, $R^6$, $R^7$, $R^8$, and Z may independently be thioisocyanate, cyanato, or thiocyanato.

Examples of complexes comprising Grubbs-Hoveyda ligands suitable in the invention include:

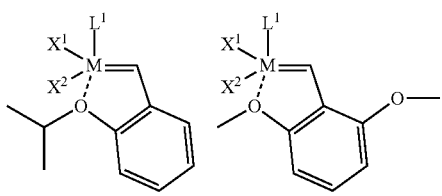

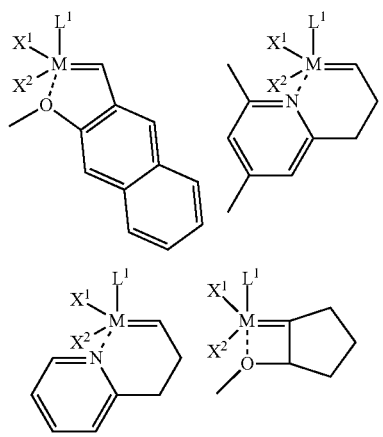

wherein, $L^1$, $X^1$, $X^2$, and M are as described for any of the other groups of catalysts. Suitable chelating carbenes and carbene precursors are further described by Pederson et al. (U.S. Pat. Nos. 7,026,495 and 6,620,955, the disclosures of both of which are incorporated herein by reference) and Hoveyda et al. (U.S. Pat. No. 6,921,735 and WO0214376, the disclosures of both of which are incorporated herein by reference).

Other useful complexes include structures wherein $L^2$ and $R^2$ according to formulae (I), (III), or (V) are linked, such as styrenic compounds that also include a functional group for attachment to a support. Examples in which the functional group is a trialkoxysilyl functionalized moiety include, but are not limited to, the following:

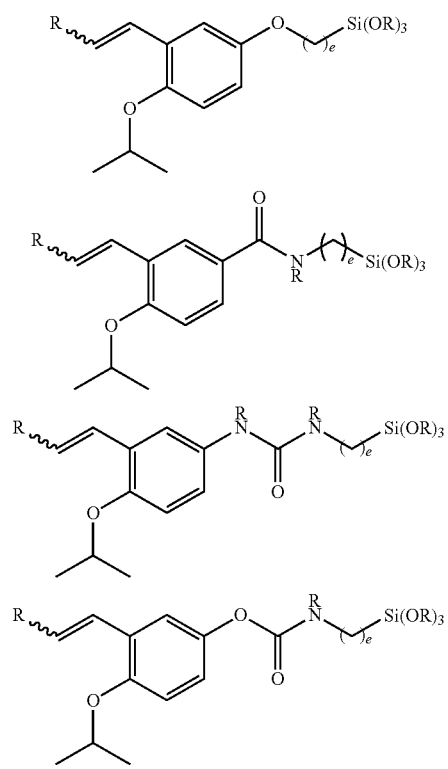

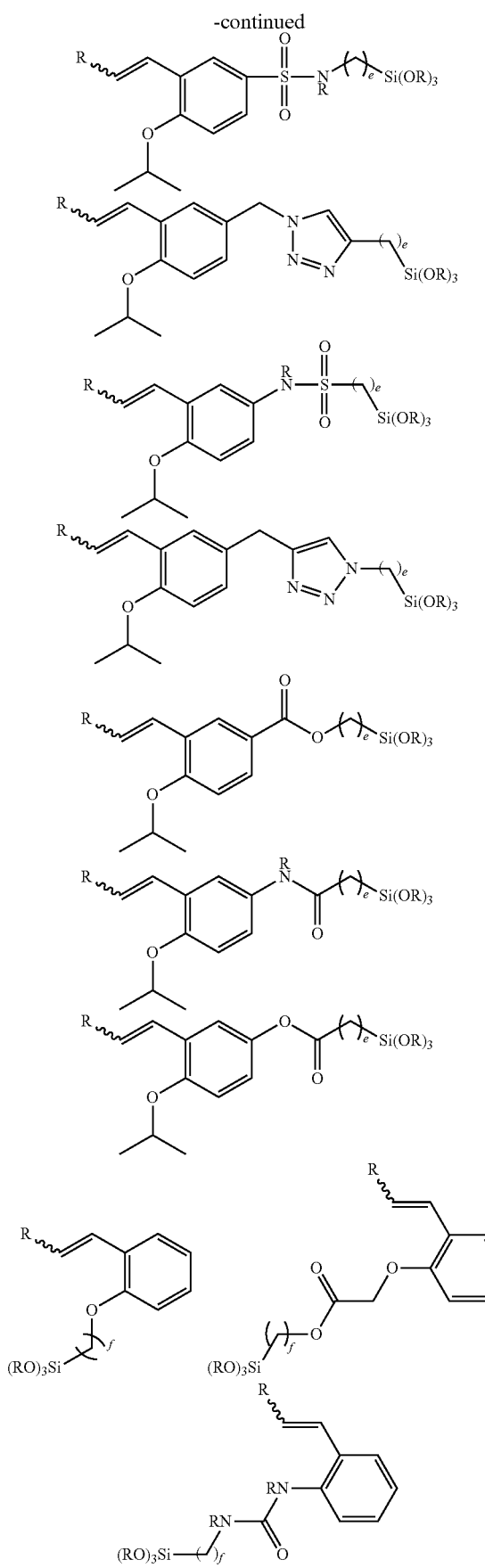

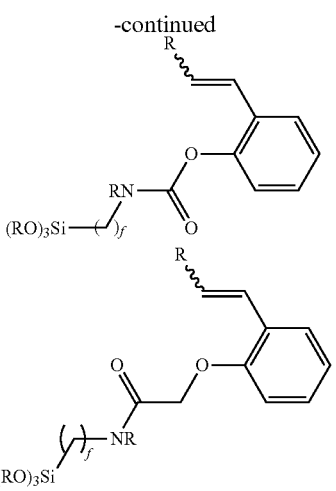

Further examples of complexes having linked ligands include those having linkages between a neutral NHC ligand and an anionic ligand, a neutral NHC ligand and an alkylidine ligand, a neutral NHC ligand and an $L^2$ ligand, a neutral NHC ligand and an $L^3$ ligand, an anionic ligand and an alkylidine ligand, and any combination thereof. While the possible structures are too numerous to list herein, some suitable structures based on formula (III) include:

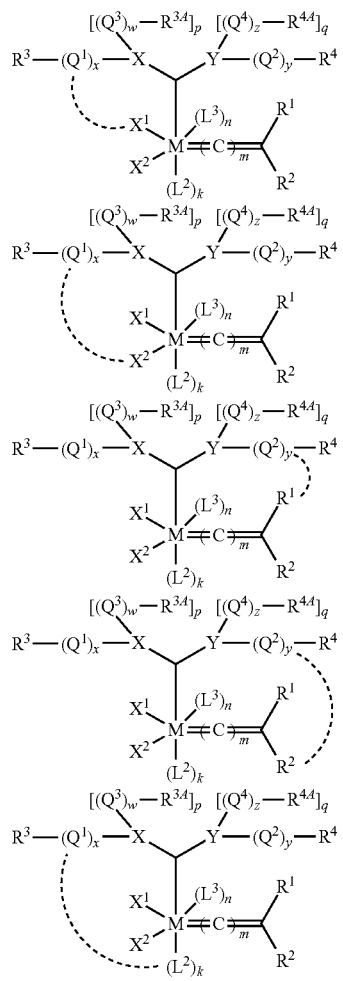

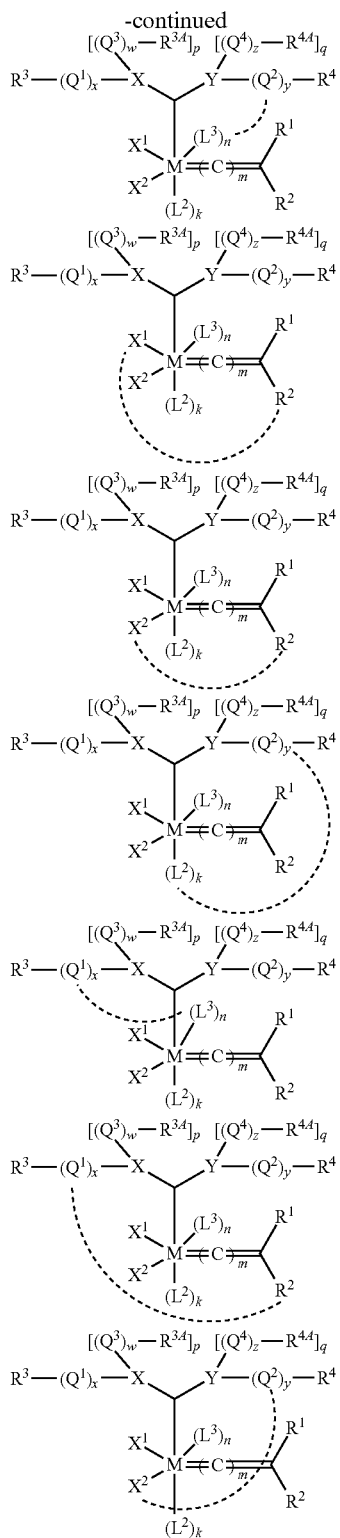

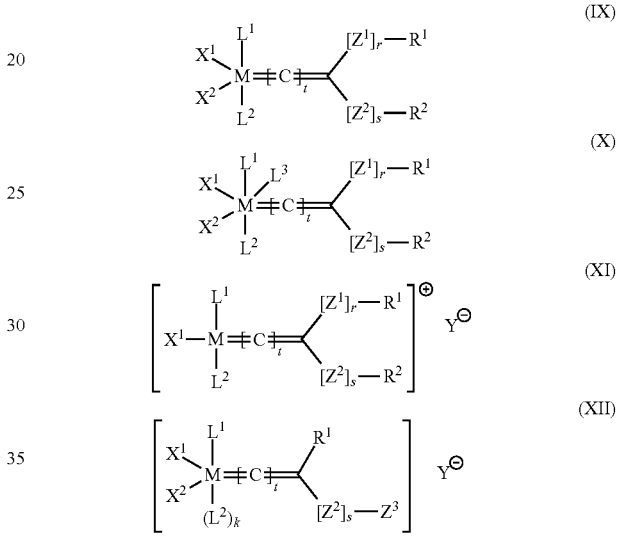

In addition to the catalysts that have the structure of formula (I), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14 or 16, are tetra-coordinated or penta-coordinated, respectively, and are of the general formula (XII)

wherein:

$M$, $X^1$, $X^2$, $L^1$, $L^2$, $L^3$, $R^1$, and $R^2$ are as defined for any of the previously defined four groups of catalysts;

r and s are independently zero or 1;

t is an integer in the range of zero to 5;

k is an integer in the range of zero to 1;

Y is any non-coordinating anion (e.g., a halide ion, $BF_4^-$, etc.);

$Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, —S(=O)$_2$—, —, and an optionally substituted and/or optionally heteroatom-containing $C_1$-$C_{20}$ hydrocarbylene linkage;

$Z^3$ is any cationic moiety such as —P($R^2$)$_3^+$ or —N($R^2$)$_3^+$; and any two or more of $X^1$, $X^2$, $L^1$, $L^2$, $L^3$, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, $L^3$, $Z^1$, $Z^2$, $Z^3$, $R^1$, and $R^2$ may be attached to a support.

Additionally, another group of olefin metathesis catalysts that may be used in the invention disclosed herein, is a Group 8 transition metal complex having the structure of formula (XIII):

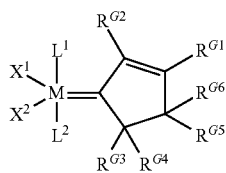

(XIII)

wherein M is a Group 8 transition metal, particularly ruthenium or osmium, or more particularly, ruthenium;

$X^1$, $X^2$, $L^1$ and $L^2$ are as defined for the first and second groups of catalysts defined above; and $R^{G1}$, $R^{G2}$, $R^{G3}$, $R^{G4}$, $R^{G5}$, and $R^{G6}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or any one or more of the $R^{G1}$, $R^{G2}$, $R^{G3}$, $R^{G4}$, $R^{G5}$, and $R^{G6}$ may be linked together to form a cyclic group, or any one or more of the $R^{G1}$, $R^{G2}$, $R^{G3}$, $R^{G4}$, $R^{G5}$, and $R^{G6}$ may be attached to a support.

Additionally, one preferred embodiment of the Group 8 transition metal complex of formula XIII is a Group 8 transition metal complex of formula (XIV):

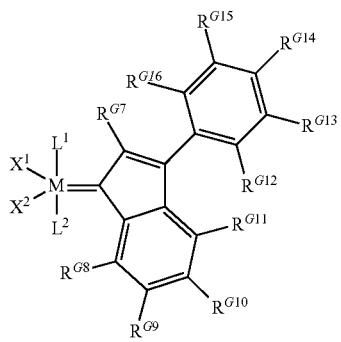

(XIV)

wherein M, $X^1$, $X^2$, $L^1$, $L^2$, are as defined above for Group 8 transition metal complex of formula XIII; and $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ are as defined above for $R^{G1}$, $R^{G2}$, $R^{G3}$, $R^{G4}$, $R^{G5}$, and $R^{G6}$ for Group 8 transition metal complex of formula XIII or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be linked together to form a cyclic group, or any one or more of the $R^{G7}$, $R^{G8}$, $R^{G9}$, $R^{G10}$, $R^{G11}$, $R^{G12}$, $R^{G13}$, $R^{G14}$, $R^{G15}$ and $R^{G16}$ may be attached to a support.

Additionally, another preferred embodiment of the Group 8 transition metal complex of formula XIII is a Group 8 transition metal complex of formula (XV):

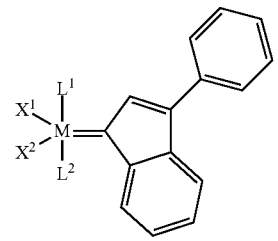

(XV)

wherein M, $X^1$, $X^2$, $L^1$, $L^2$, are as defined above for Group 8 transition metal complex of formula XIII.

Additionally, another group of olefin metathesis catalysts that may be used in the invention disclosed herein, is a Group 8 transition metal complex comprising a Schiff base ligand having the structure of formula (XVI):

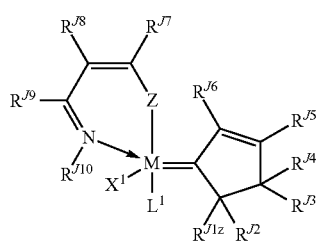

(XVI)

wherein M is a Group 8 transition metal, particularly ruthenium or osmium, or more particularly, ruthenium;

$X^1$ and $L^1$ are as defined for the first and second groups of catalysts defined above;

Z is selected from the group consisting of oxygen, sulfur, selenium, $NR^{J11}$, $PR^{J11}$, $AsR^{J11}$, and $SbR^{J11}$; and $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be linked together to form a cyclic group, or any one or more of the $R^{J1}$, $R^{J2}$, $R^{J3}$, $R^{J4}$, $R^{J5}$, $R^{J6}$, $R^{J7}$, $R^{J8}$, $R^{J9}$, $R^{J10}$, and $R^{J11}$ may be attached to a support.

Additionally, one preferred embodiment of the Group 8 transition metal complex of formula (XVI) is a Group 8 transition metal complex comprising a Schiff base ligand having the structure of formula (XVII):

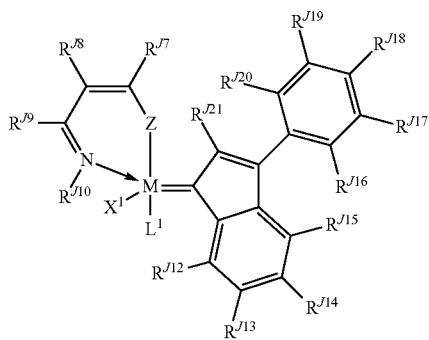

(XVII)

wherein M, $X^1$, $L^1$, Z, $R^{J7}$, $R^{J8}$, $R^{J9}$, $R^{J10}$, and $R^{J11}$ are as defined above for Group 8 transition metal complex of formula XVI; and $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ are as defined above for $R^{J1}$, $R^{J2}$, $R^{J3}$, $R^{J4}$, $R^{J5}$, and $R^{J6}$ for Group 8 transition metal complex of formula XVI, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be linked together to form a cyclic group, or any one or more of the $R^{J7}$, $R^{J8}$, $R^{J9}$, $R^{J10}$, $R^{J11}$, $R^{J12}$, $R^{J13}$, $R^{J14}$, $R^{J15}$, $R^{J16}$, $R^{J17}$, $R^{J18}$, $R^{J19}$, $R^{J20}$, and $R^{J21}$ may be attached to a support.

Additionally, another preferred embodiment of the Group 8 transition metal complex of formula (XVI) is a Group 8 transition metal complex comprising a Schiff base ligand having the structure of formula (XVIII):

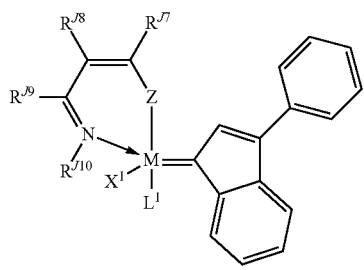

(XVIII)

wherein M, $X^1$, $L^1$, Z, $R^{J7}$, $R^{J8}$, $R^{J9}$, $R^{J10}$, and $R^{J11}$ are as defined above for Group 8 transition metal complex of formula (XVI).

Additionally, another group of olefin metathesis catalysts that may be used in the invention disclosed herein, is a Group 8 transition metal complex comprising a Schiff base ligand having the structure of formula (XIX):

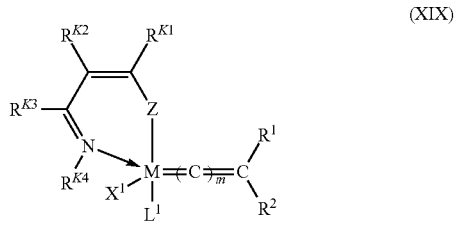

(XIX)

wherein M is a Group 8 transition metal, particularly ruthenium or osmium, or more particularly, ruthenium;

$X^1$, $R^1$, and $R^2$ are as defined for the first and second groups of catalysts defined above;

Z is selected from the group consisting of oxygen, sulfur, selenium, $NR^{K5}$, $PR^{K5}$, $AsR^{K5}$, and $SbR^{K5}$;

m is 0, 1, or 2; and $R^{K1}$, $R^{K2}$, $R^{K3}$, $R^{K4}$, and $R^{K5}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, thioisocyanate, cyanato, thiocyanato, hydroxyl, ester, ether, thioether, amine, alkylamine, imine, amide, halogen-substituted amide, trifluoroamide, sulfide, disulfide, sulfonate, carbamate, silane, siloxane, phosphine, phosphate, borate, or -A-Fn, wherein "A" is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group, or any one or more of the $R^{K1}$, $R^{K2}$, $R^{K3}$, $R^{K4}$, and $R^{K5}$ may be linked together to form a cyclic group, or any one or more of the $R^{K1}$, $R^{K2}$, $R^{K3}$, $R^{K4}$, and $R^{K5}$ may be attached to a support.

In addition, catalysts of formulas (XVI) to (XIX) may be optionally contacted with an activating compound, where at least partial cleavage of a bond between the Group 8 transition metal and at least one Schiff base ligand occurs, wherein the activating compound is either a metal or silicon compound selected from the group consisting of copper (I) halides; zinc compounds of the formula $Zn(R^{Y1})_2$, wherein $R^{Y1}$ is halogen, $C_1$-$C_7$ alkyl or aryl; tin compounds represented by the formula $snR^{Y2}R^{Y3}R^{Y4}R^{Y5}$ wherein each of $R^{Y2}$, $R^{Y3}$, $R^{Y4}$ and $R^{Y5}$ is independently selected from the group consisting of halogen, $C_1$-$C_{20}$ alkyl, $C_3$-$C_{10}$ cycloalkyl, aryl, benzyl and $C_2$-$C_7$ alkenyl; and silicon compounds represented by the formula $SiR^{Y6}R^{Y7}R^{Y8}R^{Y9}$ wherein each of $R^{Y6}$, $R^{Y7}$, $R^{Y8}$, $R^{Y9}$ is independently selected from the group consisting of hydrogen, halogen, $C_1$-$C_{20}$ alkyl, halo, $C_1$-$C_7$ alkyl, aryl, heteroaryl, and vinyl. In addition, catalysts of formulas (XVI) to (XIX) may be optionally contacted with an activating compound where at least partial cleavage of a bond between the Group 8 transition metal and at least one Schiff base ligand occurs, wherein the activating compound is an inorganic acid such as hydrogen iodide, hydrogen bromide, hydrogen chloride, hydrogen fluoride, sulfuric acid, nitric acid, iodic acid, periodic acid, perchloric acid, HOClO, $HOClO_2$ and $HOIO_3$. In addition, catalysts of formulas (XVI) to (XIX) may be optionally contacted with an activating compound where at least partial cleavage of a bond between the Group 8 transition metal and at least one Schiff base ligand occurs, wherein the activating compound is an organic acid such as sulfonic acids including but not limited to methanesulfonic acid, aminobenzenesulfonic acid, benzenesulfonic acid, p-toluenesulfonic acid (also commonly referred to as tosic acid or PTSA), napthalenesulfonic acid, sulfanilic acid and trifluoromethanesulfonic acid; monocarboxylic acids including but not limited to acetoacetic acid, barbituric acid, bromoacetic acid, bromobenzoic acid, chloroacetic acid, chlorobenzoic acid, chlorophenoxyacetic acid, chloropropionic acid, cis-cinnamic acid, cyanoacetic acid, cyanobutyric acid, cyanophenoxyacetic acid, cyanopropionic acid, dichloroacetic acid, dichloroacetylacetic acid, dihydroxybenzoic acid, dihydroxymalic acid, dihydroxytartaric acid, dinicotinic acid, diphenylacetic acid, fluorobenzoic acid, formic acid, furancarboxylic acid, furoic acid, glycolic acid, hippuric acid, iodoacetic acid, iodobenzoic acid, lactic acid, lutidinic acid, mandelic acid, α-naphtoic acid, nitrobenzoic acid, nitrophenylacetic acid, o-phenylbenzoic acid, thioacetic acid, thiophene-carboxylic acid, trichloroacetic acid, and trihydroxybenzoic acid; and other acidic substances such as but not limited to picric acid and uric acid.

In addition, other examples of catalysts that may be used with the present invention are located in the following disclosures, each of which is incorporated herein by reference, U.S. Pat. Nos. 7,687,635; 7,671,224; 6,284,852; 6,486,279; and 5,977,393; International Publication Number WO2010/037550; and U.S. patent application Ser. Nos. 12/303,615; 10/590,380; 11/465,651 (U.S. Pat. App. Pub. No.: US 2007/0043188); and Ser. No. 11/465,651 (U.S. Pat. App. Pub. No.: US 2008/0293905 Corrected Publication); and European Pat. Nos. EP 1757613B1 and EP 1577282B1.

Non-limiting examples of catalysts that may be used to prepare supported complexes and in the reactions disclosed herein include the following, some of which for convenience are identified throughout this disclosure by reference to their molecular weight:

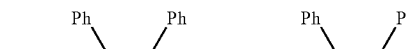
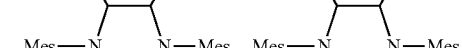
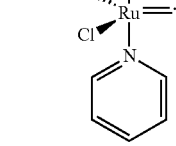
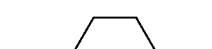
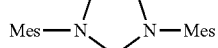
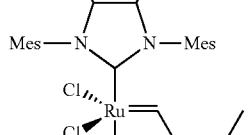
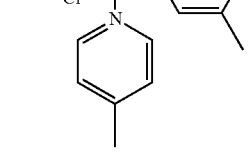

-continued

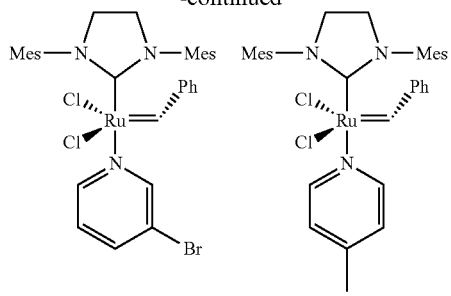
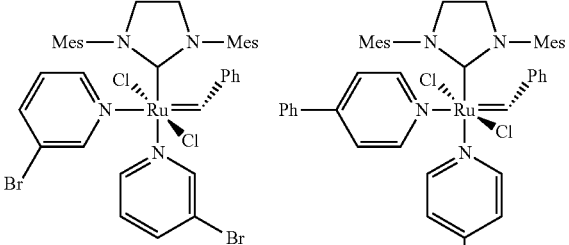
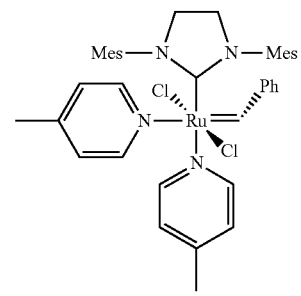

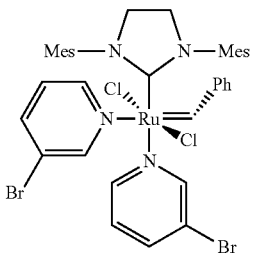

C884

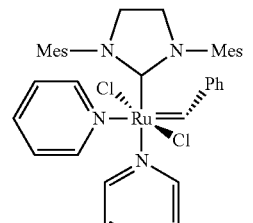

C727

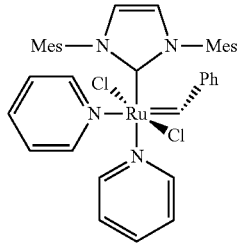

C827
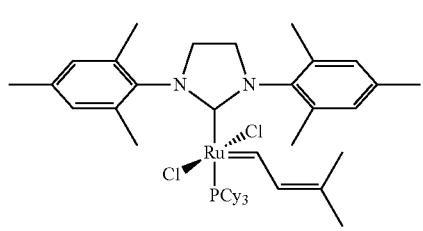
C859
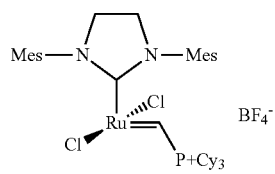
C841-n
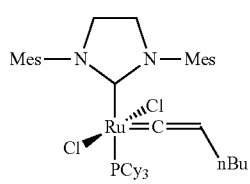
C916
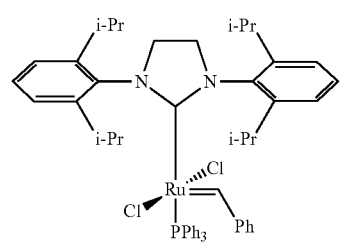
C965-p
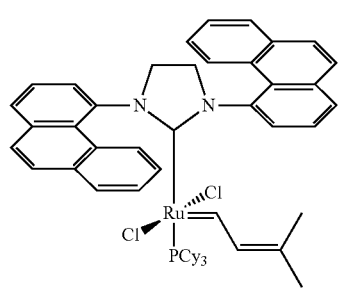
C727
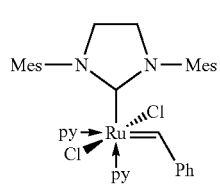
C577
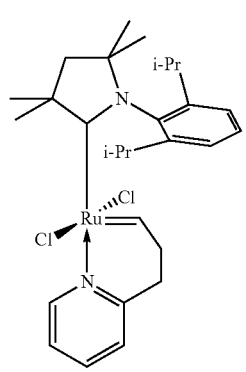
C646
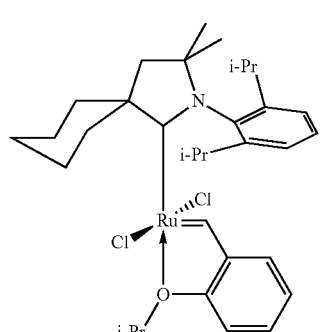
C701
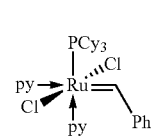
C767-m
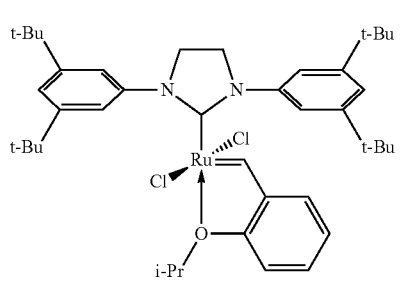
C811
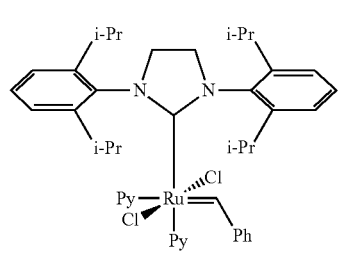
C801
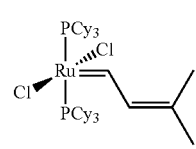

C838
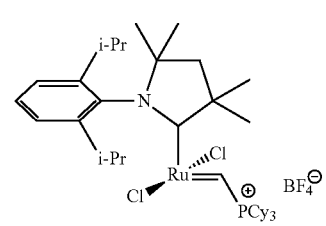
C712
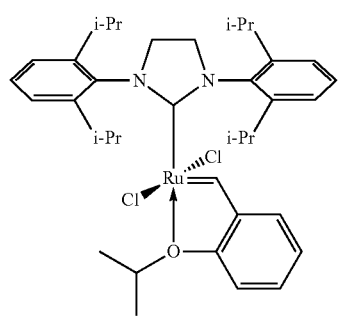
C933
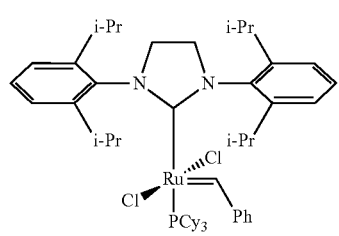
C824
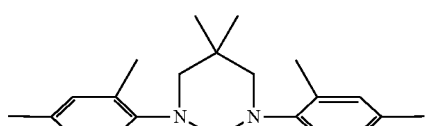
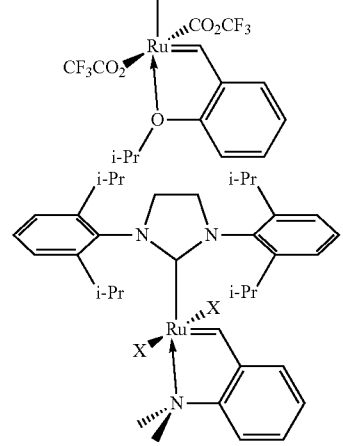
C697 (X = Cl)
C785 (X = Br)
C879 (X = I)
C601
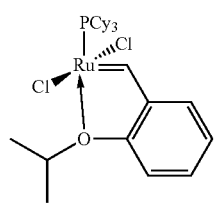
C848
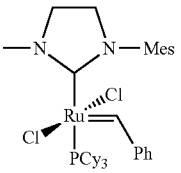
C831
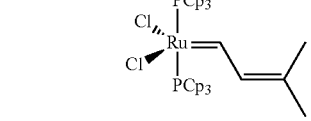
C627
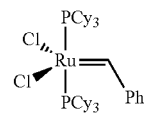
C716
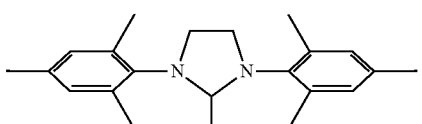
C823
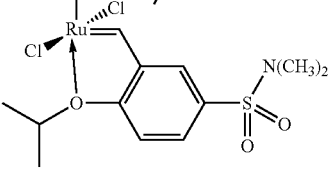
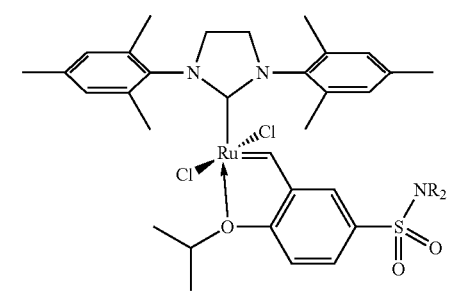

-continued
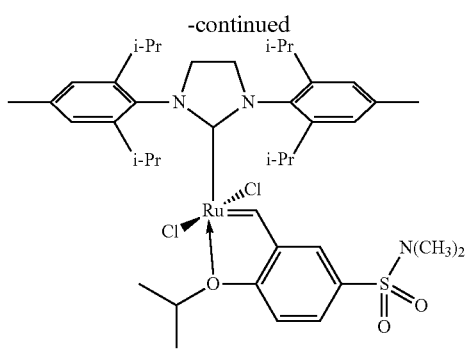
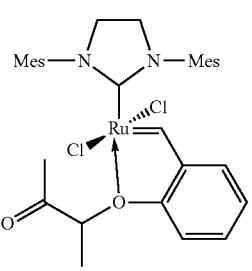
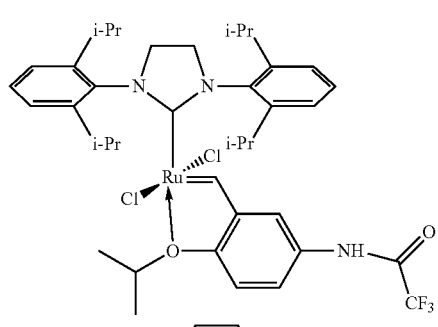
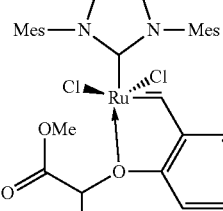
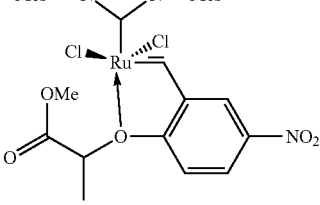
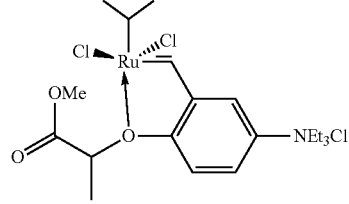
-continued
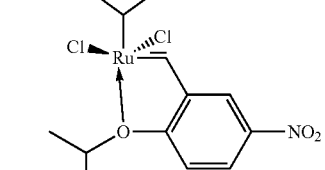
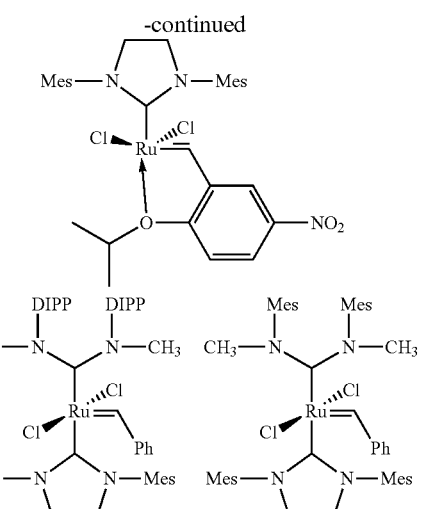
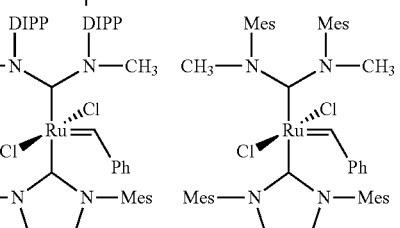
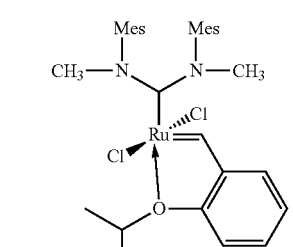
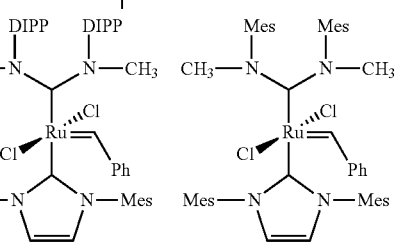
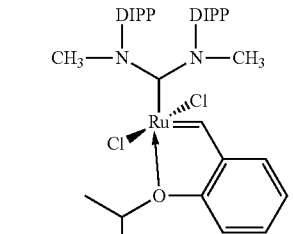
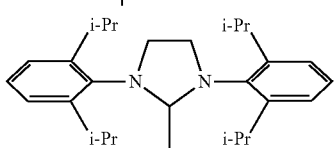
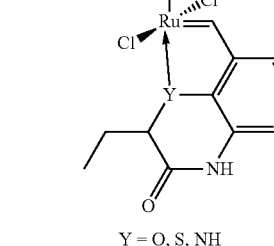
Y = O, S, NH

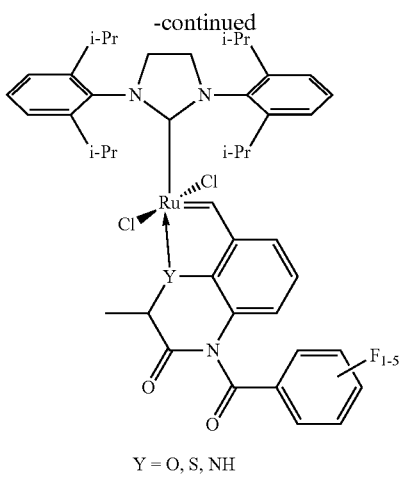

Y = O, S, NH

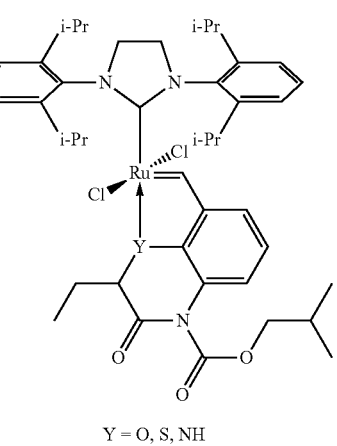

Y = O, S, NH

Y = O, S, NH

In the foregoing molecular structures and formulae, Ph represents phenyl, Cy represents cyclohexyl, Cp represents cyclopentyl, Me represents methyl, Bu represents n-butyl, t-Bu represents tert-butyl, i-Pr represents isopropyl, py represents pyridine (coordinated through the N atom), Mes represents mesityl (i.e., 2,4,6-trimethylphenyl), DiPP and DIPP represents 2,6-diisopropylphenyl, and MiPP represents 2-isopropylphenyl.

Further examples of catalysts useful to prepare supported complexes and in the reactions disclosed herein include the following: ruthenium (II) dichloro(3-methyl-2-butenylidene) bis(tricyclopentylphosphine) (C716); ruthenium (II) dichloro(3-methyl-2-butenylidene)bis(tricyclohexylphosphine) (C801); ruthenium (II) dichloro(phenylmethylene)bis(tricyclohexylphosphine) (C823); ruthenium (II) (1,3-bis-(2,4,6-trimethylphenyl)-2-imidazolidinylidene)dichloro(phenylmethylene) (triphenylphosphine) (C830); ruthenium (II) dichloro phenylvinylidene)bis(tricyclohexylphosphine) (C835); ruthenium (II) dichloro(tricyclohexylphosphine) (o-isopropoxyphenylmethylene) (C601); ruthenium (II) (1,3-bis-(2, 4,6-trimethylphenyl)-2-imidazolidinylidene)dichloro(phenylmethylene)bis(3-bromopyridine) (C884); [1,3-bis-(2,4,6-trimethylphenyl)-2-imidazolidinylidene]dichloro(o-isopropoxyphenylmethylene) ruthenium(II) (C627); [1,3-bis-(2,4,6-trimethylphenyl)-2-imidazolidinylidene]dichloro (benzylidene) (triphenylphosphine) ruthenium(II) (C831); [1,3-bis-(2,4,6-trimethylphenyl)-2-imidazolidinylidene]dichloro(benzylidene)(methyldiphenylphosphine)ruthenium (II) (C769); [1,3-bis-(2,4,6-trimethylphenyl)-2-imidazolidinylidene]dichloro(benzylidene)(tricyclohexylphosphine) ruthenium(II) (C848); [1,3-bis-(2,4,6-trimethylphenyl)-2-imidazolidinylidene]dichloro(benzylidene) (diethylphenylphosphine)ruthenium(II) (C735); [1,3-bis-(2, 4,6-trimethylphenyl)-2-imidazolidinylidene]dichloro (benzylidene)(tri-n-butylphosphine)ruthenium(II) (C771); [1,3-bis-(2,4,6-trimethylphenyl)-2-imidazolidinylidene]dichloro(3-methyl-2-butenylidene)(triphenylphosphine) ruthenium(II) (C809); [1,3-bis-(2,4,6-trimethylphenyl)-2-imidazolidinylidene]dichloro(3-methyl-2-butenylidene) (methyldiphenylphosphine)ruthenium(II) (C747); [1,3-bis-(2,4,6-trimethylphenyl)-2-imidazolidinylidene]dichloro(3-methyl-2-butenylidene) (tricyclohexylphosphine) ruthenium (II) (C827); [1,3-bis-(2,4,6-trimethylphenyl)-2-imidazolidinylidene]dichloro(3-methyl-2-butenylidene) (diethylphenylphosphine) ruthenium(II) (C713); [1,3-bis-(2, 4,6-trimethylphenyl)-2-imidazolidinylidene]dichloro(3-methyl-2-butenylidene) (tri-n-butylphosphine)ruthenium(II) (C749); [1,3-bis-(2,4,6-trimethylphenyl)-2-imidazolidinylidene]dichloro(phenylindenylidene) (triphenylphosphine) ruthenium(II) (C931); [1,3-bis-(2,4,6-trimethylphenyl)-2-imidazolidinylidene]dichloro(phenylindenylidene) (methyldiphenylphosphine) ruthenium(II) (C869); [1,3-bis-(2,4,6-trimethylphenyl)-2-imidazolidinylidene]dichloro (phenylindenylidene)(tricyclohexylphosphine)ruthenium (II) (C949); [1,3-bis-(2,4,6-trimethylphenyl)-2-imidazolidinylidene]dichloro(phenylindenylidene) (diethylphenylphosphine)ruthenium(II) (C835); and [1,3-bis-(2,4,6-trimethylphenyl)-2-imidazolidinylidene]dichloro (phenylindenylidene)(tri-n-butylphosphine)ruthenium(II) (C871).

Still further catalysts useful in ROMP reactions, and/or in other metathesis reactions, such as ring-closing metathesis, cross metathesis, ring-opening cross metathesis, self-metathesis, ethenolysis, alkenolysis, acyclic diene metathesis polymerization, and combinations thereof, include the following structures:

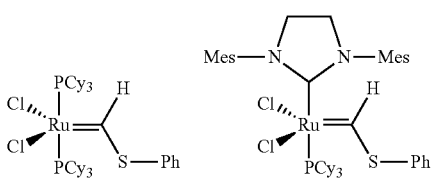

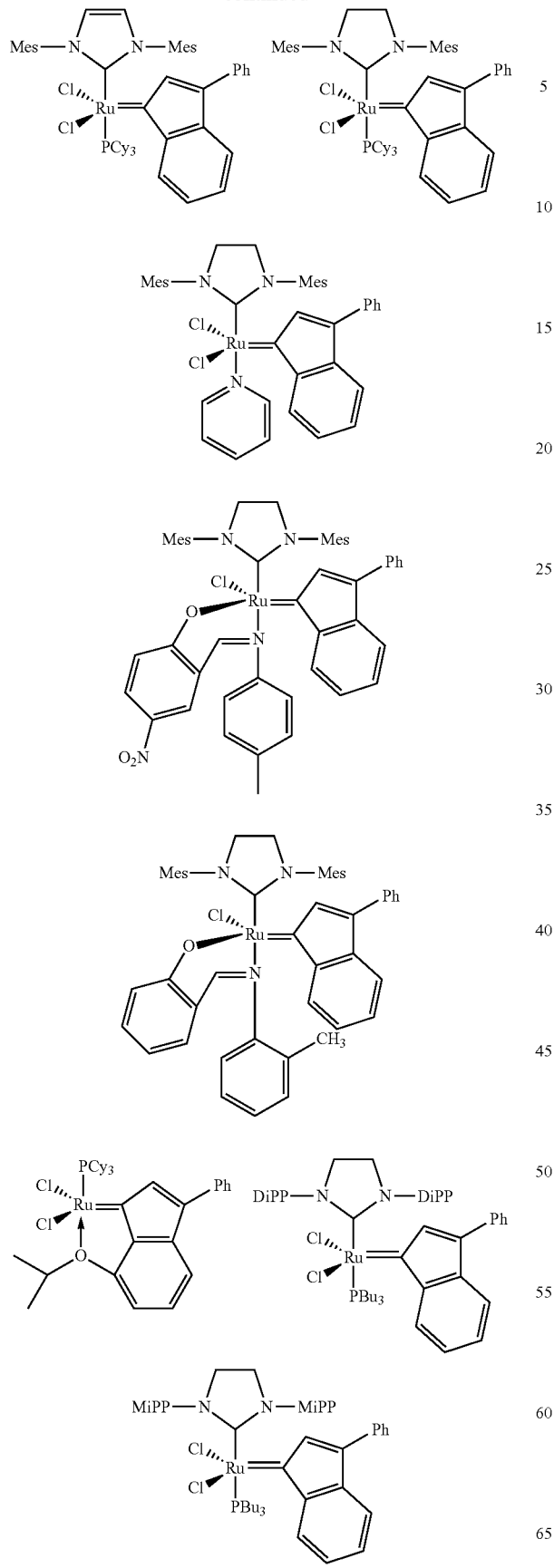

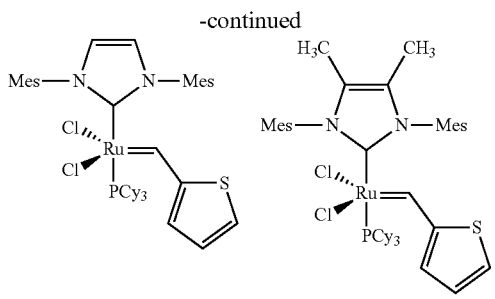

and formula (VII)

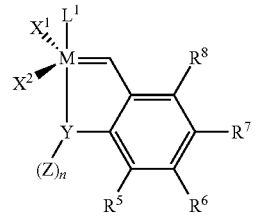

wherein,
M is a Group 8 transition metal;
$L^1$ is a neutral electron donor ligand;
$X^1$ and $X^2$ are anionic ligands;
Y is a heteroatom selected from O or N;
$R^5$, $R^6$, $R^7$, and $R^8$ are independently selected from hydrogen, hydrocarbyl, substituted hydrocarbyl, heteroatom-containing hydrocarbyl, substituted heteroatom-containing hydrocarbyl, and functional groups;
n is 0, 1, or 2; and
Z is selected from hydrogen, hydrocarbyl, substituted hydrocarbyl, heteroatom-containing hydrocarbyl, substituted heteroatom-containing hydrocarbyl, and functional groups, wherein any combination of Y, Z, $R^5$, $R^6$, $R^7$, and $R^8$ can be linked to form one or more cyclic groups, and further wherein any combination of $X^1$, $X^2$, $L^1$, Y, Z, $R^5$, $R^6$, $R^7$, and $R^8$ may be attached to a support.

In general, the transition metal complexes used as catalysts herein can be prepared by several different methods, such as those described by Schwab et al. (1996) *J. Am. Chem. Soc.* 118:100-110, Scholl et al. (1999) *Org. Lett.* 6:953-956, Sanford et al. (2001) *J. Am. Chem. Soc.* 123: 749-750, U.S. Pat. No. 5,312,940, and U.S. Pat. No. 5,342,909, the disclosures of each of which are incorporated herein by reference. Also see U.S. Pat. Pub. No. 2003/0055262 to Grubbs et al., WO 02/079208, and U.S. Pat. No. 6,613,910 to Grubbs et al., the disclosures of each of which are incorporated herein by reference. Preferred synthetic methods are described in WO 03/11455A1 to Grubbs et al., the disclosure of which is incorporated herein by reference.

Preferred metal carbene olefin metathesis catalysts are Group 8 transition metal complexes having the structure of formula (I) commonly called "First Generation Grubbs" catalysts, formula (III) commonly called "Second Generation Grubbs" catalysts, or formula (VII) commonly called "Grubbs-Hoveyda" catalysts.

More preferred olefin metathesis catalysts have the structure of formula (I)

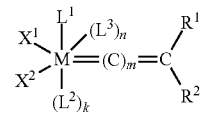

in which:
M is a Group 8 transition metal;
$L^1$, $L^2$, and $L^3$ are neutral electron donor ligands;
n is 0 or 1;
m is 0, 1, or 2;
k is 0 or 1;
$X^1$ and $X^2$ are anionic ligands;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support;

Most preferred olefin metathesis catalysts have the structure of formula (I)

(I)

in which:
M is ruthenium;
n is 0;
m is 0;
k is 1;
$L^1$ and $L^2$ are trisubstituted phosphines independently selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph); or $L^1$ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene and $L^2$ is a trisubstituted phosphine selected from the group consisting of tri-n-butylphosphine (Pn-Bu$_3$), tricyclopentylphosphine (PCp$_3$), tricyclohexylphosphine (PCy$_3$), triisopropylphosphine (P-i-Pr$_3$), triphenylphosphine (PPh$_3$), methyldiphenylphosphine (PMePh$_2$), dimethylphenylphosphine (PMe$_2$Ph), and diethylphenylphosphine (PEt$_2$Ph);

X¹ and X² are chloride;
R¹ is hydrogen and R² is phenyl or —CH=C(CH₃)₂ or thienyl; or R¹ and R² are taken together to form 3-phenyl-1H-indene;
and formula (VII)

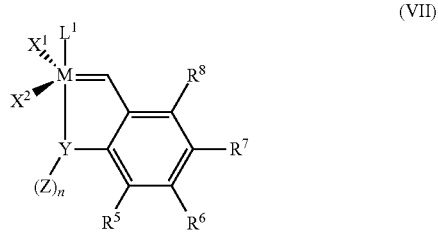

(VII)

wherein,
M is ruthenium;
L¹ is a trisubstituted phosphine selected from the group consisting of tri-n-butylphosphine (n-Bu₃P), tricyclopentylphosphine (PCp₃), tricyclohexylphosphine (PCy₃), triisopropylphosphine (P-i-Pr₃), triphenylphosphine (PPh₃), methyldiphenylphosphine (PMePh₂), dimethylphenylphosphine (PMe₂Ph), and diethylphenylphosphine (PEt₂Ph); or L¹ is an N-heterocyclic carbene selected from the group consisting of 1,3-bis(2,4,6-trimethylphenyl)-2-imidazolidinylidene, 1,3-bis(2,4,6-trimethylphenyl)imidazol-2-ylidene, 1,3-bis(2,6-di-isopropylphenyl)-2-imidazolidinylidene, and 1,3-bis(2,6-di-isopropylphenyl)imidazol-2-ylidene;
X¹ and X² are chloride;
Y is oxygen;
R⁵, R⁶, R⁷, and R⁸ are each hydrogen;
n is 1; and
Z is isopropyl.

Suitable supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups.

When utilized, suitable supports may be selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of a complex linked to the support.

The metathesis catalysts that are described herein may be utilized in olefin metathesis reactions according to techniques known in the art. The catalyst is typically added as a solid, a solution, or as a suspension. When the catalyst is added as a suspension, the catalyst is suspended in a dispersing carrier such as mineral oil, paraffin oil, soybean oil, tri-isopropylbenzene, or any hydrophobic liquid which has a sufficiently high viscosity so as to permit effective dispersion of the catalyst, and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

Other olefin metathesis catalysts suitable for use with the present invention include well-defined molybdenum and tungsten catalysts such as those developed by Schrock (Schrock, R. R. *Chem. Rev.* 2009, 109, 3211; Hartford, B. *Chemical & Engineering News*, "Z-Selective Metathesis of Macrocycles", Volume 89, Issue 45, Nov. 7, 2011, page 11; Yu, M.; Wang, C.; Kyle, A. F.; Jakubec, P.; Dixon, D. J.; Schrock, R. R.; Hoveyda, A. H. *Nature*, Nov. 3, 2011, 479, 88); each of which is incorporated by reference, examples are shown in Scheme 11.

Scheme 11.
Examples of well-defined Molybdenum and Tungsten catalysts.

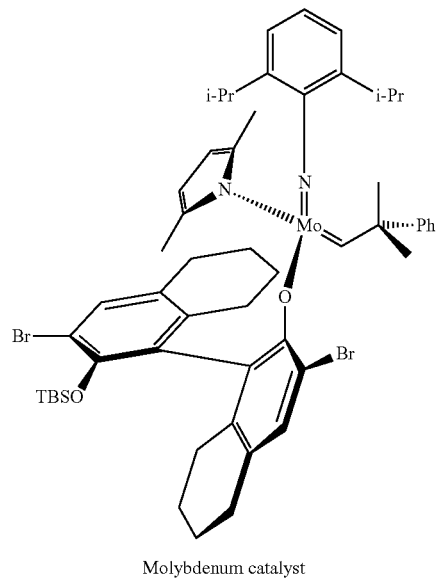

Molybdenum catalyst

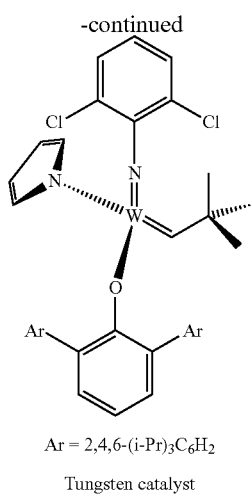

Ar = 2,4,6-(i-Pr)₃C₆H₂

Tungsten catalyst

Ill-Defined and Heterogeneous Olefin Metathesis Catalysts

Ill-defined olefin metathesis catalysts can be dated back to the 1960's with the seminal report from Banks and Bailey of Phillips Petroleum describing an "olefin disproportionation" process catalyzed by Mo(CO)$_6$, W(CO)$_6$ and MoO$_3$ supported on alumina [Banks, R. L.; Bailey, G. C. Ind. Eng. Chem. Prod. Res. Dev. 1964, 170-173]. Ill-defined olefin metathesis catalysts are defined as metathesis catalysts where the metathesis active species in not well understood [Warwel, S.; Siekermann, V. Makromol. Chem., Rapid Commun. 1983, 4, 423; Leymet, I.; Siove, A.; Parlier, A.; Rudler, H.; Fontanille, M. Makromol. Chem. 1989, 190, 2397; Liaw, D.-J.; Lin, C.-L. J. Polymer Sci., A, Polymer Chem. 1993, 31, 3151; and a review by Grubbs R. H., Chang S. Tetrahedron, 1998, 54, 4413-4450], which are incorporated by reference. A few years later, chemists at Goodyear reported a catalyst system composed of a cocktail of WCl$_6$, ethanol and EtAlCl$_2$ that interconverted olefin feedstocks [Calderon, N.; Chen, H. Y.; Scott, K. W. Tetrahedron Lett., 1967, 3327-3329], which is incorporated by reference. These early transition metal systems had limitations with respect to polar functional groups or impurities within the substrate feed; however, the initial discovery by Phillips Petroleum ultimately led to the development of the Phillips Triolefin Process which converted propylene into a mixture of ethylene and 2-butene using a silica-supported WO$_3$ catalyst. This heterogeneous catalyzed process was first performed on an industrial scale in 1985 by Lyondell [Mol, J. C. Catalysis Today 1999, 51, 289-299; Mol, J. C. J. Mol. Catal. A: Chem. 2004, 213, 39-45] and today Lummus Technology provides the support for the process, known as OCT® (Olefins Conversion Technology) which currently produces over 1.5 billion pounds of propylene per year [Wittcoff, H.; Reuben, B. G.; Plotkin, J. S. Industrial organic chemicals, 2$^{nd}$ ed.; Wiley-Interscience, 2004; Mol, J. C. J. Mol. Catal. A: Chem. 2004, 213, 39-45], all of which are incorporated by reference.

An excellent source of non-ruthenium metal metathesis catalyst can be found in Olefin Metathesis and Metathesis Polymerization, K. J. Ivin and J. C. Mol Eds., Academic Press, San Diego 1997, pp 12-49, which is incorporated by reference. Examples of metathesis catalysts from the literature are listed below.

Examples of titanium metathesis catalysts include but not limited to Tebbe's reagent (Cp)$_2$TiCH$_2$(ClAlCl$_3$), TiCl$_4$ activation of W[=C(OEt)R](CO)$_5$ where R=alkyl and aryl, (Cp)$_2$TiMe$_2$, CpTiMe$_3$, CpTiMe$_2$Cl, and Cp$_2$Ti(CH$_2$SiMe$_3$)$_2$.

Examples of zirconium metathesis catalysts include but not limited to ZrCl$_4$/Et$_3$Al and Zr(acac)$_4$/Me$_3$Al$_2$Cl$_3$.

Examples of vanadium metathesis catalysts include but not limited to V(acac)$_3$/Et$_3$AlCl, and VCl$_4$/Et$_3$Al.

Examples of niobium and tantalum metathesis catalysts include but not limited to NbCl$_5$ or TACl$_5$ activated by Et$_2$AlCl or EtAlCl$_2$, and Ta(=CHCMe$_3$)(Cl)(OCMe$_3$)$_2$PMe$_3$.

Examples of chromium metathesis catalysts include but not limited to Cr(=CPh$_2$)(CO)$_5$, Bu$_4$N[CrCl(CO)$_5$]/MeAlCl$_2$ and Cr(CO)$_3$(mesitylene)/EtAlCl$_2$/O$_2$.

Examples of molybdenum metathesis catalysts include but not limited to MoCl$_5$(NO)$_2$(py)$_2$/EtAlCl$_2$, MoCl$_5$/Et$_3$Al, MoO$_3$/Al$_2$O$_3$, MoO$_3$/CoO/Al$_2$O$_3$, MoO$_3$/Al$_2$O$_3$/Et$_3$Al, MoO$_3$/SiO$_2$, Mo(CO)$_3$/Al$_2$O$_3$, Mo(CO)$_6$/Al$_2$O$_3$, Mo$_2$(OAc)$_4$/Al$_2$O$_3$, Mo$_2$(OAc)$_4$/SiO$_2$, and (π-C$_3$H$_5$)$_4$Mo/SiO$_2$.

Examples of tungsten metathesis catalysts include but not limited to WCl$_{6-x}$(OAr)$_x$ where x=0 to 6, WOCl$_{4-y}$(OAr)$_y$, and W(=NAr)$_{4-y}$(OAr)$_y$, where y=0 to 4, with co-catalysts Me$_z$AlCl$_{3-z}$ where Z=0 to 3, W(=CCMe$_3$)neopentyl/SiO$_2$, W(=CCMe$_3$)(Cl)$_3$(dme), and W(=CCMe$_3$)(OCMe$_3$)$_3$; and (2,6-Ph$_2$-PhO)$_2$(Cl)(Et$_2$O) W=CH—CMe$_3$ in Couturier, J.-L., Paillet, C., Leconte, M., Basset, J.-M., Weiss, K.; Angew. Chem. Int. Ed. Engl. 1992, 31, 628-631, which is incorporated by reference.

Examples of rhenium metathesis catalysts include but not limited to Re$_2$O$_7$/Al$_2$O$_3$, Re$_2$(CO)$_{10}$/Al$_2$O$_3$, B$_2$O$_3$/Re$_2$O$_7$/Al$_2$O$_3$—SiO$_2$, CH$_3$ReO$_3$/SiO$_2$—Al$_2$O$_3$, ReCl$_5$/EtAlCl$_2$, ReOCl$_3$(PPh$_3$)$_2$/EtAlCl$_2$, and Re(CO)$_5$Cl/EtAlCl$_2$.

Examples of osmium metathesis catalysts include but not limited to OsCl$_3$ 3H$_2$O/EtOH and OsO$_4$ in chlorobenzene 60° C.

Examples of iridium metathesis catalysts include but not limited to [(C$_8$H$_{14}$)$_2$IrCl]$_2$ and excess of CF$_3$CO$_2$Ag, [(C$_8$H$_{14}$)$_2$IrO$_2$CCF$_3$]$_z$, RNH$_4$)$_2$IrCl$_6$/EtOH.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

The following examples are to be considered as not being limiting of the invention as described herein, and are instead provided as representative examples of compositions and methods of the invention.

Examples

Materials and Methods

All solvents and reagents were purchased from commercial suppliers and used as received unless otherwise noted. All reactions were performed under ambient conditions unless otherwise noted. Ethylene (Grade 3.0 grade, 99.9% purity) and hydrogen (4.5 Grade) were purchased from Praxair. 1-Hexene (purity 99%), 1-heptene (purity 97%), 1-decene (purity >97%), alpha-methyl styrene (purity 99%), hexacosane (purity 99%), phenyl Grignard (phenylmagnesium bromide 3.0M in diethyl ether), glacial acetic acid (purity >99%), methylene chloride (dichloromethane) (anhydrous, >99.8%), methyl styrene (i.e., tolyl styrene) (purity 99%; containing 60% meta, 40% para, and <1% ortho isomers), hexanes (anhydrous, >99.9% purity), Pd/C (10 wt %), ethyl acetate (anhydrous, 99.8% purity), styrene (purity >99%), and diethylaluminum chloride in hexanes (1.0 M) were purchased from Sigma-Aldrich. 4-Methyl-1-pentene (purity 97%), 1-nonene (purity >90%), 1-tetradecene (purity >90%), 3-undecanone (purity >97%), 1-undecene (purity 93%) were purchased from TCI. 1-octene (purity >97%) was purchased from Acros. 1-dodecene (purity >90%) was purchased from Fluka. 5-decene, 7-tetradecene, 9-octadecene, 11-docosene, and 2,7-dimethyl-4-octene were produced by an analogous procedure described by Pederson et al., *Advanced Synthesis & Catalysis* 2002, 344, 728-735. 5% NaOH (aq), 10% NaOH (aq), 15% NaOH (aq), and 20% NaOH (aq) were made by dilution of NaOH (50% in water) from Ashland. Hydrovinylation catalyst (PPh$_3$)$_2$CoCl$_2$ was prepared according to known methods, a representative procedure is described in Cotton, F. A.; Faut, O. D.; Goodgame, D. M. L.; Holm, R. H. *J. Am. Chem. Soc.* 1961, 83, 1780. Silica gel 60 was from EMD. Oleum (sulfuric acid with 20-30% free SO$_3$) were from Acros.

Internal olefins were produced by the self-metathesis of an alpha olefin; a representative procedure is described in U.S. Pat. No. 6,215,019 for the synthesis of 5-decene made by the self-metathesis of 1-hexene. 9-Octadecene was made by an analogous procedure except using 1-decene. Alkenolysis reactions are as described in *Topics in Catalysis* 2012, 55, 518 and ruthenium metathesis catalyst removal was as described in *Adv. Synth. Catalysis* 2002, 344, 728, using tris(hydroxymethyl)phosphine (THMP).

Olefin metathesis catalysts [1,3-Bis-(2,6-diisopropylphenyl)-2-imidazolidinylidene]dichloro(o-isopropoxyphenylmethylene) ruthenium (II) (C711); [1,3-bis-(2,4,6-trimethylphenyl)-2-imidazolidinylidene]dichloro(3-methyl-2-butenylidene)(tricyclohexylphosphine) ruthenium (II) (C827); [1,3-Bis(2,4,6-trimethylphenyl)-2-imidazolidinylidene]dichloro(phenylmethylene)(triphenylphosphine) ruthenium (II) (C831); [1,3-Bis(2,4,6-trimethylphenyl)-2-imidazolidinylidene]dichloro(phenylmethylene) (tricyclohexylphosphine) ruthenium (II) (C848); [1,3-Bis(26-diisopropylphenyl)-2-imidazolidinylidene]dichloro (phenylmethylene) (tricyclohexylphosphine) ruthenium (II) (C933); [1,3-bis-(2,4,6-trimethylphenyl)-2-imidazolidinylidene]dichloro(o-isopropoxyphenylmethylene) ruthenium(II) (C627) were prepared by procedures described in U.S. Pat. Nos. 6,921,735; 6,759,537; 5,969,170; 7,329,758; 6,111,121 and 7,329,758.

GC Analytical Methods

Volatile products were analyzed using an Agilent 6850 gas chromatography (GC) instrument with a flame ionization detector (FID). The following conditions and equipment were used:
Column: HP-5, 30 m×0.25 mm (ID)×0.25 μm film thickness.
Manufacturer: Agilent
GC conditions: Injector temperature: 250° C.
Detector temperature: 280° C.
Oven temperature: Starting temperature: 100° C., hold time: 1 minute.
Ramp rate 10° C./min to 250° C., hold time: 12 minutes.
Carrier gas: Helium Mean gas velocity: 31.3±3.5% cm/sec (calculated)
Split ratio: ~50:1
The products were characterized by comparing peaks with known standards, in conjunction with supporting data from mass spectrum analysis (GCMS-Agilent 5973N). GCMS analysis was accomplished with a second HP-5, 30 m×0.25 mm (ID)×0.25 μm film thickness GC column, using the same method as above.

An aliquot of the metathesis reaction was withdrawn at the desired times, filtered through a plug of silica gel and analyzed by gas chromatography.

Experimental Reactions

Reaction 1.
Synthesis of 3-phenyl-1-butene by hydrovinylation of styrene.

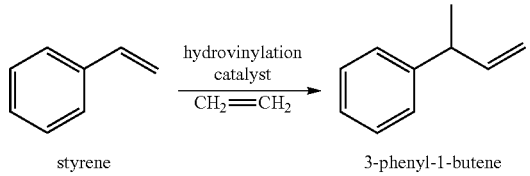

styrene            3-phenyl-1-butene

Under a stream of argon, (PPh$_3$)$_2$CoCl$_2$ (15.0 g, 22.9 mmol), dichloromethane (3.0 L), and styrene (4.0 L, 34.4 mol) were combined in an 18 L Parr reactor. The reactor was sealed, and cooled to −10° C. while the headspace was purged with ethylene. A solution of diethylaluminum chloride in hexanes (1.0 M, 115 mL, 115 mmol) was introduced. The reactor was promptly sealed and charged with ethylene (435 psi). After 14 h the pressure was released the reaction passed through a plug of silica gel. The silica gel was washed with dichloromethane and the organic fractions were combined and concentrated under rotary evaporation. Subsequent purification by vacuum distillation afforded 3-phenyl-1-butene (Bpt 45.7° C. to 46.0° C. at 5 mmHg, 4.1 kg, 89% yield and 99% purity). 3-Phenyl-1-butene was produced in >99% isomeric purity (neither 2-phenyl-2-butene nor 2-phenyl-1-butene isomers were detected by $^1$H NMR and <0.5% 2-phenyl-2-butene was detected by GC analysis). $^1$H NMR (400 MHz, CDCl$_3$) δ 1.66 (d, J=6.8 Hz, 3H), 3.75 (m, 1H), 5.34 (ddd, J=10.4, 1.6 and 1.6 Hz, 1H), 5.36 (ddd, J=17.2, 1.6 and 1.6 Hz, 1H), 6.31 (ddd, J=17.2, 10.4 and 6.4 Hz, 1H), 7.28-7.46 (m, 5H); $^{13}$C NMR (101 MHz, CDCl$_3$) 20.7, 43.2, 113.0, 126.1, 127.2, 128.4, 143.2, 145.4.

Reaction 2. Preparation of 2-Phenyl-3-decene.

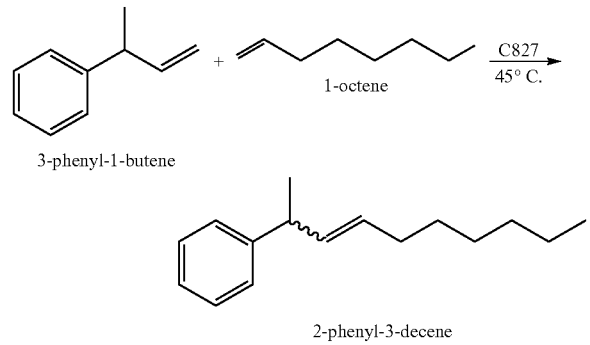

A 5 liter jacketed flask equipped with a reflux condenser and magnetic stir bar was charged with 1-octene (1.70 kg, 15.1 mol) and 3-phenyl-1-butene (0.50 kg, 3.78 mol). The reaction mixture was sparged with argon for 45 minutes and heated to 45° C. Grubbs metathesis catalyst C827 (0.313 g, 0.378 mmol) in dichloromethane (3.0 mL) was subsequently added to the reaction mixture. The reaction mixture was allowed to stir at 45° C. under a slow, continuous argon purge for 6 hours. The reaction mixture was then cooled to room temperature and filtered through a plug of silica gel. The filter cake was washed with hexanes twice and all organic fractions combined and concentrated under reduced pressure. Subsequent purification by vacuum distillation afforded 2-phenyl-3-decene (Bpt 87.9° C. at 50 mmHg, 488 g, 56.1% yield, 99% purity). GC analysis determined the product to be a mixture of cis-2-phenyl-3-decene (8.3%) and trans-2-phenyl-3-decene (91.7%). $^1$H NMR (400 MHz, CDCl$_3$) δ 0.96 (t, J=7.2 Hz, 3H), 1.25-1.60 (m, 11H), 2.09 (pquar, J=7.2 Hz, 2H), 3.49 (pquint, J=7.0 Hz, 1H), 5.50-5.57 (m, 1H), 5.60-5.70 (m, 1H), 7.21-7.30 (m, 3H), 7.34-7.38 (m, 2H). $^{13}$C NMR (101 MHz, CDCl$_3$) δ 15.7, 23.0, 24.0, 30.1, 30.7, 32.9, 33.7, 43.1, 124.6, 125.8, 127.0, 127.9, 133.4, 144.7.

Reaction 3. Preparation of 2-Phenyl-3-undecene.

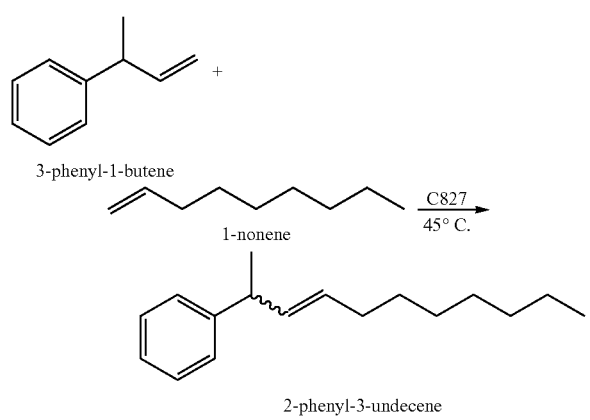

2-phenyl-3-undecene

A 5 liter jacketed flask equipped with a reflux condenser and magnetic stir bar was charged with 1-nonene (330 g, 2.61 mol) and 3-phenyl-1-butene (1.04 kg, 7.84 mol). The reaction mixture was sparged with argon for 45 minutes and heated to 45° C. Grubbs metathesis catalyst C827 (0.216 g, 0.261 mmol) in dichloromethane (3.0 mL) was subsequently added to the reaction mixture. The reaction mixture was allowed to stir at 45° C. with slow, continuous argon purge for 6 hours. The reaction mixture was then cooled to room temperature and filtered through a plug of silica gel. The filter cake was washed with hexanes twice and all organic fractions combined. Subsequent purification by vacuum distillation afforded 2-phenyl-3-undecene (Bpt 85° C. at 60 mmHg, 228 g, 38.1% yield, 97% purity). GC analysis determined the product to be a mixture of cis-2-phenyl-3-undecene (11.2%) and trans-2-phenyl-3-undecene (88.8%). $^1$H NMR (400 MHz, CDCl$_3$, trans isomer) δ 0.95 (t, J=6.8 Hz, 3H), 1.25-1.55 (m, 13H), 2.07 (pquar, J=7.1 Hz, 2H), 3.48 (pquint, J=6.8 Hz, 1H), 5.40-5.60 (m, 1H), 5.61-5.70 (m, 1H), 7.20-7.30 (m, 3H), 7.31-7.37 (m, 2H). $^1$H NMR (400 MHz, CDCl$_3$, cis isomer, selected resonances) δ 2.18 (m, 2H), 3.84 (m, 1H). $^{13}$C NMR (101 MHz, CDCl$_3$, trans isomer) δ 15.7, 23.0, 24.1, 30.4, 30.4, 30.8, 33.0, 33.7, 43.2, 124.6, 125.8, 127.0, 128.0, 133.4, 144.8. $^{13}$C NMR (101 MHz, CDCl$_3$, cis isomer, selected resonances) δ 23.7, 28.7, 30.4, 30.5, 30.9, 38.2, 124.5, 125.6, 127.0, 127.6, 133.3, 144.9.

Reaction 4. Preparation of 2-Phenyl-3-dodecene.

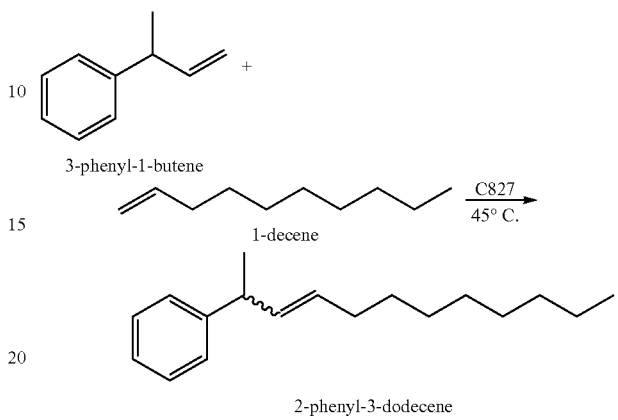

2-phenyl-3-dodecene

A 5 liter jacketed flask equipped with a reflux condenser, vacuum adapter, and magnetic stir bar was charged with 1-decene (2.65 kg, 18.9 mol) and 3-phenyl-1-butene (0.50 kg, 3.78 mol). The reaction mixture was sparged with argon for 45 minutes, subjected to 4 mmHg vacuum, and heated to 45° C. Grubbs metathesis catalyst C827 (0.312 g, 0.378 mmol) in dichloromethane (3.0 mL) was subsequently added to the reaction mixture. The reaction mixture was allowed to stir at 45° C. and 4 mmHg vacuum for 6 hours. The reaction mixture was then cooled to room temperature and filtered through a plug of silica gel. The filter cake was washed with hexanes twice and all organic fractions combined and concentrated under reduced pressure. Vacuum distillation was not successful and the crude product (1.23 kg, 28% 2-phenyl-3-dodecene) was therefore used in subsequent transformations without purification. GC analysis determined the desired product to be a mixture of cis-2-phenyl-3-dodecene (15.1%) and trans-2-phenyl-3-dodecene (84.9%). An NMR sample was obtained by silica gel column chromatography using hexanes as the mobile. Fractions were analyzed by UV light, the UV active fractions were analyzed by GC where pure fractions of 2-phenyl-3-dodecene were combined and concentrated under reduced pressure. $^1$H NMR (400 MHz, CDCl$_3$, trans isomer) δ 0.92 (t, J=7.0 Hz, 3H), 1.20-1.55 (m, 15H), 2.04 (pquar, J=7.2 Hz, 2H), 3.45 (pquint, J=6.8 Hz, 1H), 5.40-5.60 (m, 1H), 5.61-5.70 (m, 1H), 7.18-7.29 (m, 3H), 7.30-7.36 (m, 2H). $^1$H NMR (400 MHz, CDCl$_3$, cis isomer, selected resonances) δ 2.15 (m, 2H), 3.81 (m, 1H). $^{13}$C NMR (101 MHz, CDCl$_3$, trans isomer) δ 15.7, 23.0, 24.1, 30.4, 30.5, 30.7, 30.7, 33.0, 33.7, 43.1, 124.6, 125.8, 127.0, 128.0, 133.4, 144.8. $^{13}$C NMR (101 MHz, CDCl$_3$, cis isomer, selected resonances) δ 23.7, 28.7, 30.6, 30.7, 30.9, 38.2, 124.52, 125.6, 127.0, 127.6, 133.3, 144.9.

Reaction 5. Preparation of 2-Phenyl-3-hexadecene.

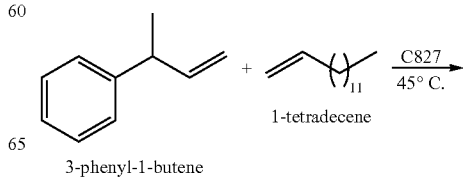

3-phenyl-1-butene

-continued

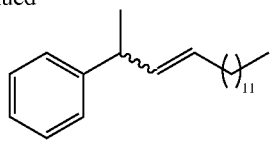

2-phenyl-3-hexadecene

A 2 liter flask equipped with a reflux condenser and magnetic stir bar was charged with 1-tetradecene (125.0 g, 0.637 mol) and 3-phenyl-1-butene (252.5 g, 1.91 mol). The reaction mixture was sparged with argon for 45 minutes and heated to 45° C. Grubbs metathesis catalyst C827 (0.263 g, 0.032 mmol) in dichloromethane (2.0 mL) was subsequently added to the reaction mixture. The reaction mixture was allowed to stir at 45° C. under vacuum (4 mmHg) for 6 hours. The reaction mixture was filtered through a plug of silica gel. The filter cake was washed with hexanes twice and all organic fractions combined and concentrated under reduced pressure. GC analysis determined a 72% yield of 2-phenyl-3-hexadecene as a mixture of cis-2-phenyl-3-hexadecene (11%) and trans-2-phenyl-3-hexadecene (89%) isomers. Due to similar boiling points of 2-phenyl-3-hexadecene and 13-hexacosene ($13C_{26}$), purification by vacuum distillation resulted in 138 g of 89% purity 2-phenyl-3-hexadecene which was subsequently hydrogenated without further purification.

Reaction 6. Representative example for the synthesis of internal olefins from the self-metathesis of alpha olefins.

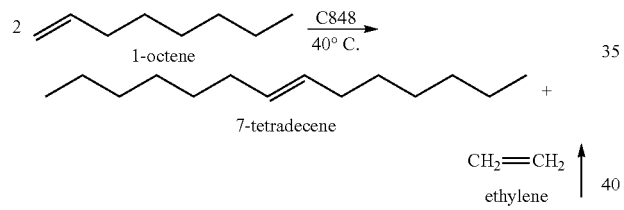

A 3 liter, 3-neck round bottom flask was equipped with a magnetic stir bar and fitted with a reflux condenser, vacuum adapter, and a rubber septum. The flask was charged with 1-octene (1.00 kg, 8.91 mol) and subjected to full vacuum (4 mmHg) at 40° C. for 30 minutes. A solution of Grubbs metathesis catalyst C848 in dichloromethane (25 ppm) was added via syringe to the reaction mixture under vacuum. After the reaction had reached completion, as judged by GC analysis, the crude mixture was filtered through a pad of silica gel and vacuum distillation afforded 7-tetradecene ($7C_{14}$) (Bpt 71° C. at 0.15 mmHg, 761 g, 87.0% yield). $^1$H NMR (400 MHz, CDCl$_3$) δ 0.83 (t, 6H, J=6.8 Hz), 1.25 (m, 16H), 5.30-5.45 (m, 2H, cis and trans isomers in a 23:77 ratio). $^{13}$C NMR (101 MHz, CDCl$_3$) δ 14.31, 22.89, 27.48, 29.08, 29.23, 29.88, 30.00, 32.01, 32.85, 130.15, 130.62.

The same procedure was followed for the synthesis the following internal olefins:

9-octadecene ($9C_{18}$), Bpt 148° C.-151° C. at 1.30 mmHg, $^1$H NMR (400 MHz, CDCl$_3$) δ 0.94 (t, J=7.0 Hz, 6H), 1.25-1.45 (m, 24H), 1.97-2.12 (m, 4H), 5.35-5.47 (m, 2H, cis and trans isomers in a 26:74 ratio). $^{13}$C NMR (101 MHz, CDCl$_3$) δ 14.1, 22.8, 27.4, 29.4, 29.5, 29.7, 29.7, 28.5, 30.0, 32.1, 32.8, 129.9, 130.4.

11-docosene ($11C_{22}$), Bpt 176° C.-180° C. at 0.15 mmHg, $^1$H NMR (400 MHz, CDCl$_3$) δ 0.94 (t, J=6.6 Hz, 6H), 1.25-1.45 (m, 32H), 1.97-2.12 (m, 4H), 5.36-5.46 (m, 2H, cis and trans isomers in a 19:81 ratio) $^{13}$C NMR (101 MHz, CDCl$_3$) δ 14.2, 22.9, 27.4, 29.4, 29.5, 29.6, 29.8, 29.8, 29.9, 30.0, 32.1, 32.8, 129.9, 130.4.

Reaction 7. Synthesis of methyl substituted internal olefins from the self-metathesis of methyl substituted alpha olefins.

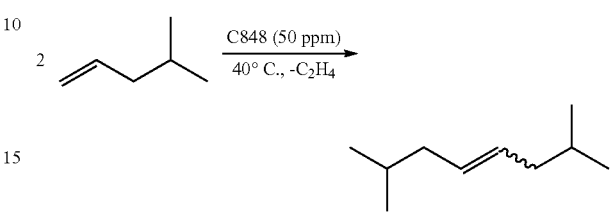

A 100 mL, 2-neck round bottom flask was equipped with a magnetic stir bar and fitted with a reflux condenser and rubber septum. The flask was charged with 4-methyl-1-pentene (50.0 mL, 395 mmol) and Grubbs metathesis catalyst C848 (16.8 mg, 0.0198 mmol). The reaction was heated to 40° C. and sparged with argon for 2 hours then filtered through a pad of silica gel. Distillation afforded 2,7-dimethyl-4-octene (Bpt 152° C.-156° C., 17.2 g, 62.1% yield). GC analysis determined the product to be a mixture of trans-2,7-dimethyl-4-octene (83%) and cis-2,7-dimethyl-4-octene (17%). Trans-2,7-dimethyl-4-octene: $^1$H NMR (400 MHz, CDCl$_3$) δ 0.94 (t, J=7.0 Hz, 12H), 1.64 (septet, J=6.7 Hz, 2H), 1.93 (m, 4H), 5.41 (m, 2H). $^{13}$C NMR (101 MHz, CDCl$_3$) δ 22.4, 28.7, 42.3, 130.3. Cis-2,7-dimethyl-4-octene: $^1$H NMR (400 MHz, CDCl$_3$) δ 0.94 (t, J=7.0 Hz, 12H), 1.64 (septet, J=6.7 Hz, 2H), 1.97 (m, 4H), 5.46 (m, 2H). $^{13}$C NMR (101 MHz, CDCl$_3$) δ 22.5, 28.9, 36.6, 129.3.

Reaction 8. Synthesis of a mixture of Internal Olefins (IOs) by the self-metathesis of Alpha Olefins (AOs).

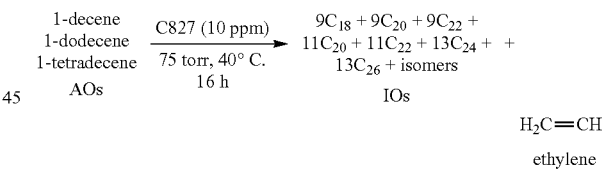

A 3 liter, 3-neck round bottom flask was equipped with a magnetic stir bar and fitted with a reflux condenser, vacuum adapter, and a rubber septum. The flask was charged with an equimolar ratio of 1-decene, 1-dodecene, and 1-tetradecene then heated to 40° C. and subjected to vacuum (75 mmHg) for 30 minutes. A solution of Grubbs metathesis catalyst C827 in dichloromethane (10 ppm C827 to AOs) was added via syringe to the reaction mixture under vacuum. After 16 hours the reaction was filtered through a pad of silica gel and unreacted α-olefins (AOs) were removed by vacuum distillation to afford $C_{17}$-$C_{26}$ internal olefins (IOs) in 83% yield. Internal olefins $C_{17}$, $C_{19}$, $C_{21}$, $C_{23}$ and $C_{25}$ represented minor components of the mixture (i.e. <5% each). The odd carbon internal olefins were a result of double bond migration, followed by cross metathesis. This mixture was subsequently used in cross metathesis reactions with 3-phenyl-1-butene (Table 2, runs 16-19).

Reaction 9. Synthesis of 2-phenyl-3-decene by cross-metathesis of 3-phenyl-1-butene with 7-tetradecene.

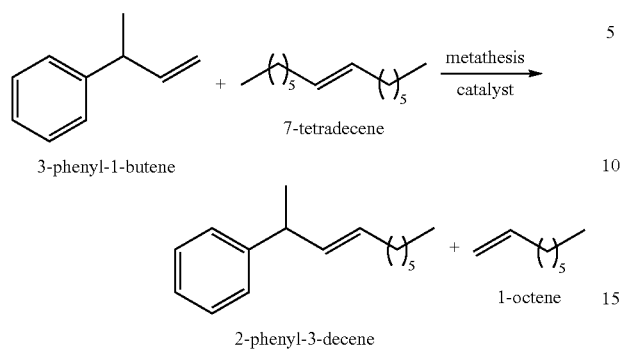

In an argon filled glovebox, 3-phenyl-1-butene (200 mg, 1.51 mmol), 7-tetradecene (446 mg, 2.27 mmol), and Grubbs metathesis catalyst were combined in a scintillation vial equipped with a magnetic stirbar. The vial was sealed, removed from the glovebox and stirred at 23° C. or 40° C. Samples were taken at various time points and analyzed by gas chromatography for conversion of 3-phenyl-1-butene (3P1B) and yield of 2-phenyl-3-decene (2P3D). Results are summarized in Table 1.

TABLE 1

Synthesis of 2-phenyl-3-decene (2P3D).

| Run | catalyst (ppm) | temp (° C.) | time (h) | 3P1B (% conv.) | 2P3D (% yield) |
|---|---|---|---|---|---|
| 1 | C827 (10) | 23 | 2 | 24.2 | 23.1 |
|   |           |    | 6 | 46.2 | 40.8 |
| 2 | C827 (200) | 23 | 2 | 83.5 | 81.2 |
|   |            |    | 6 | 91.9 | 88.4 |
| 3 | C827 (10) | 40 | 2 | 60.6 | 57.2 |
| 4 | C831 (10) | 23 | 2 | 69.5 | 66.6 |
|   |           |    | 6 | 84.1 | 80.6 |
| 5 | C831 (200) | 23 | 2 | 92.0 | 86.7 |
|   |            |    | 6 | 93.6 | 84.5 |
| 6 | C831 (10) | 40 | 2 | 73.2 | 69.5 |
| 7 | C848 (10) | 23 | 2 | 72.9 | 69.6 |
|   |           |    | 6 | 78.3 | 74.7 |
| 8 | C848 (200) | 23 | 2 | 91.3 | 86.3 |
|   |            |    | 6 | 94.2 | 85.1 |
| 9 | C848 (10) | 40 | 2 | 81.5 | 77.0 |
| 10 | C711 (10) | 23 | 2 | 67.6 | 62.4 |
|    |           |    | 6 | 85.5 | 80.0 |
| 11 | C711 (200) | 23 | 2 | 98.2 | 63.9 |
|    |            |    | 6 | 98.3 | 45.8 |
| 12 | C711 (10) | 40 | 2 | 77.3 | 71.1 |

Reaction 10. Representative example for the synthesis of 2-phenyl-3-alkenes by cross-metathesis of 3-phenyl-1-butene with internal olefins.

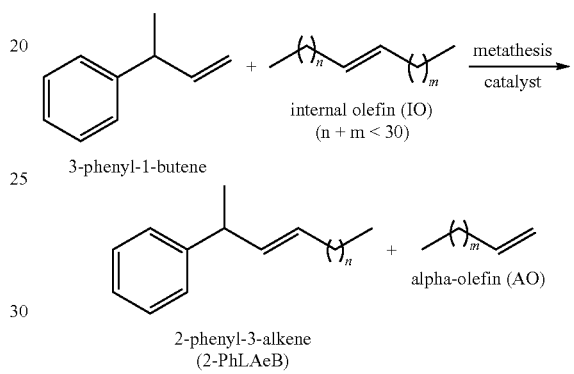

where n and m are independently selected from 0 to 25

In an argon filled glovebox, 3-phenyl-1-butene (2.00 g, 15.1 mmol), internal olefin (2 equiv, 30.3 mmol), and Grubbs metathesis catalyst (100 ppm) were combined in a scintillation vial equipped with a magnetic stirbar. The vial was sealed, removed from the glovebox and stirred at 40° C. for 6 hours. A sample was taken, filtered through a plug of silica gel, and analyzed by gas chromatography for conversion of 3-phenyl-1-butene (3P1B) and yield of 2-phenyl-3-alkenes (2PhLAeB). Results are summarized in Table 2.

TABLE 2

Synthesis of 2-phenyl-3-alkenes (2PhLAeB).

| run | catalyst | olefin | time (h) | 3P1B (% conv) | 2PhLAeB (% yield) | 2PhLAeB |
|---|---|---|---|---|---|---|
| 13 | C827 | 9-octadecene | 6 | 74.0 | 71.4 | 2-phenyl-3-undecene |
| 14 | C848 | 9-octadecene | 6 | 68.2 | 65.1 | 2-phenyl-3-undecene |
| 15 | C827 | 11-docosene | 6 | 78.4 | 58.9 | 2-phenyl-3-tetradecene |
| 16 | C827 | $C_{17}$-$C_{26}$ IOs | 6 | 58.9 | 56.0 | 2-phenyl-3-alkenes[1] |
| 17 | C831 | $C_{17}$-$C_{26}$ IOs | 6 | 37.3 | 37.3 | 2-phenyl-3-alkenes[1] |
| 18 | C848 | $C_{17}$-$C_{26}$ IOs | 6 | 6.5 | 6.5 | 2-phenyl-3-alkenes[1] |
| 19 | C933 | $C_{17}$-$C_{26}$ IOs | 6 | 3.7 | 3.7 | 2-phenyl-3-alkenes[1] |

[1] 2-phenyl-3-alkenes includes alkene chains containing 9 to 16 carbons

Additional examples of 2PhLAeB that can be prepared by this method include, but are not limited to, 2-phenyl-3-pentene, 2-phenyl-3-hexene, 2-phenyl-3-heptene, 2-phenyl-3-octene, 2-phenyl-3-nonene, 2-phenyl-3-tridecene, 2-phenyl-3-pentadecene, 2-phenyl-3-heptadecene, 2-phenyl-3-octadecene, 2-phenyl-3-nonadecene and 2-phenyl-3-eicosene.

Reaction 11. Synthesis of 2-phenyl-6-methyl-3-heptene by cross-metathesis of 3-phenyl-1-butene with 2,7-dimethyl-4-octene.

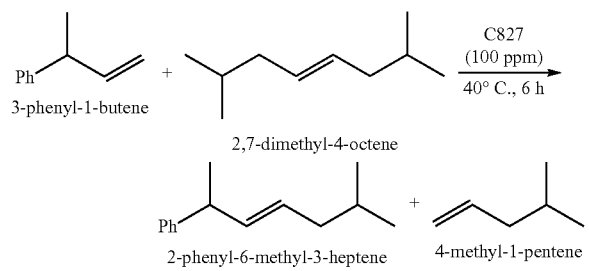

In an argon filled glovebox, 3-phenyl-1-butene (2.00 g, 15.1 mmol), 2,7-dimethyl-4-octene (4.24 g, 30.2 mmol), and Grubbs metathesis catalyst (100 ppm) were combined in a scintillation vial equipped with a magnetic stirbar. The vial was sealed, removed from the glovebox and stirred at 40° C. for 6 hours. A sample was taken, filtered through a plug of silica gel, and analyzed by gas chromatography. GC analysis, 79.3% yield of 2-phenyl-6-methyl-3-heptene.

Reaction 12. Synthesis of 2-phenyl-2-nonene by cross-metathesis of α-methylstyrene with 7-tetradecene.

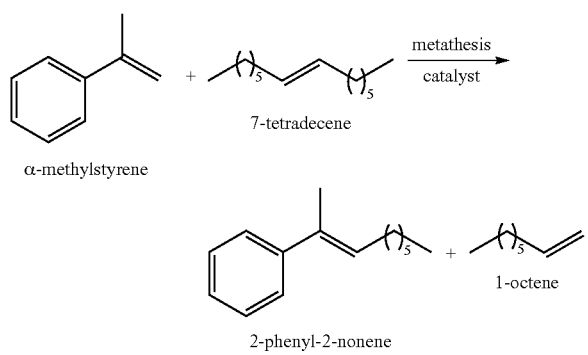

In an argon filled glovebox, α-methyl styrene (500 mg, 4.23 mmol), 7-tetradecene (1.25 g, 6.35 mmol), and Grubbs metathesis catalyst were combined in a scintillation vial equipped with a magnetic stir bar. The vial was sealed, removed from the glovebox and stirred at 23° C. or 40° C. Samples were taken at various time points and analyzed by gas chromatography for conversion of α-methylstyrene (AMS) and yield of 2-phenyl-2-nonene (2P2N) was determined by GC analysis. Results are summarized in Table 3.

TABLE 3

Synthesis of 2-phenyl-2-nonene (2P2N).

| run | catalyst (ppm) | temp (° C.) | time (h) | AMS (% conv) | 2P2N (% yield) |
|---|---|---|---|---|---|
| 23 | C827 (10) | 23 | 2 | trace | trace |
|    |           |    | 24 | 1.9 | 1.9 |
| 24 | C827 (10) | 40 | 2 | 1.2 | 1.2 |
|    |           |    | 24 | 7.9 | 6.2 |
| 25 | C831 (10) | 23 | 2 | 4.7 | 3 |
|    |           |    | 24 | 8.4 | 6.6 |
| 26 | C831 (10) | 40 | 2 | 5.0 | 4.7 |
|    |           |    | 24 | 13.1 | 10 |
| 27 | C848 (10) | 23 | 24 | 2.1 | 2.1 |
| 28 | C848 (10) | 40 | 24 | 4.1 | 4.1 |
| 29 | C711 (10) | 23 | 2 | 1 | 1 |
|    |           |    | 24 | 5.1 | 3.9 |
| 30 | C711 (10) | 40 | 2 | 1.2 | 1.2 |
|    |           |    | 24 | 6.8 | 4.3 |

Reaction 13. Representative example of the synthesis of 2-phenyl-2-alkenes by cross-metathesis of α-methylstyrene with terminal olefins.

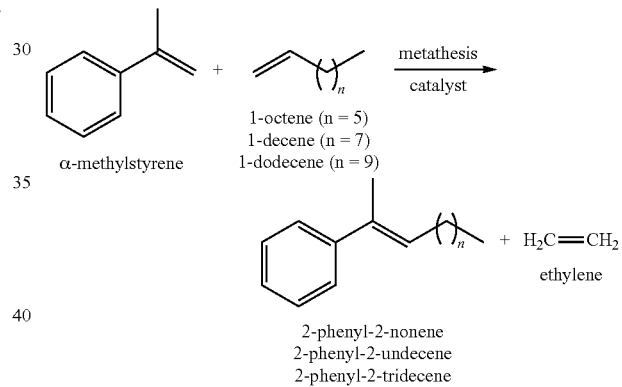

In an argon filled glovebox, α-methylstyrene (500 mg, 4.23 mmol), terminal olefin (3 equiv, 12.7 mmol), and Grubbs metathesis catalyst (100 ppm) were combined in a scintillation vial equipped with a magnetic stirbar. The vial was sealed, removed from the glovebox and stirred at 40° C. for 6 hours under a flow of argon. A sample was taken, filtered through a plug of silica gel, and analyzed by gas chromatography for conversion of α-methylstyrene (AMS) and yield of 2PhLAeB. Results are summarized in Table 4.

TABLE 4

Synthesis of 2-phenyl-2-alkenes from α-methylstyrene and α-olefins.

| run | catalyst | α-olefin | time (h) | AMS (% conv) | 2PhLAeB (% yield) |
|---|---|---|---|---|---|
| 31 | C827 | 1-octene | 6 | 15.2 | 13.1[1] |
| 32 | C827 | 1-decene | 6 | 16.1 | 13.5[2] |
| 33 | C827 | 1-dodecene | 6 | 15.8 | 13.3[3] |

[1] 2PhLAeB = 2-phenyl-2-nonene
[2] 2PhLAeB = 2-phenyl-2-undecene
[3] 2PhLAeB = 2-phenyl-2-tridecene Reaction 14. General hydrogenation procedure to yield 2-phenyl alkylbenzene (2PhLAB)

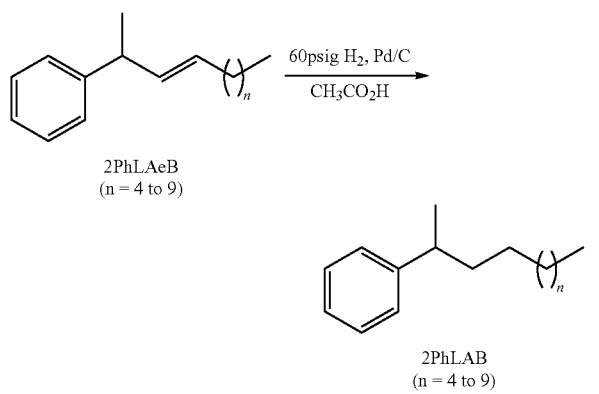

2PhLAeB
(n = 4 to 9)

2PhLAB
(n = 4 to 9)

To a fisher porter bottle equipped with stirbar and pressure gauge was added 2-phenyl linear alkene benzene (2PhLAeB), 10 equivalents glacial acetic acid and 0.05 equivalents Pd/C. The reaction vessel was sealed and sparged with argon for 15 minutes. Then, the reaction vessel was attached to hydrogen via metal Schlenk line, sparged with hydrogen then pressurized to 60 psig. The reaction mixture was allowed to stir at room temperature until the reaction reached completion as determined by GC analysis. The reaction vessel was subsequently vented and the crude mixture was diluted with hexanes and filtered through a silica plug. Vacuum distillation yielded 2-phenyl alkylbenzene (2Ph-LAB).

2-Phenyldecane (2PhC$_{10}$ LAB, 84.8% yield, 99% purity). $^1$H NMR (400 MHz, CDCl$_3$) δ 0.95 (t, J=6.8 Hz, 3H), 1.15-1.50 (m, 15H), 1.64 (m, 2H), 2.74 (psext, J=7.0 Hz, 1H), 7.20-7.28 (m, 3H), 7.31-7.39 (m, 2H). $^{13}$C NMR (101 MHz, CDCl$_3$) δ 14.1, 22.3, 22.7, 27.8, 29.3, 29.6, 29.8, 31.9, 28.5, 40.0, 125.7, 127.0, 128.2, 148.0.

2-Phenylundecane (2PhC$_{11}$ LAB, 99.1% yield), Bpt 90° C. at 60 mmHg $^1$H NMR (400 MHz, CDCl$_3$) δ 0.92 (t, J=6.6 Hz, 3H), 1.10-1.45 (m, 17H), 1.60 (m, 2H), 2.71 (psext, J=7.0 Hz, 1H), 7.18-7.25 (m, 3H), 7.29-7.36 (m, 2H). $^{13}$C NMR (101 MHz, CDCl$_3$) δ 15.7, 23.7, 24.1, 29.0, 30.6, 30.8, 30.8, 31.0, 33.1, 39.4, 40.9, 124.4, 125.7, 126.9, 146.1.

2-Phenyldodecane (2PhC$_{12}$ LAB, a crude mixture composed of 72% 9-octadecene and 28% 2-phenyl-3-dodecene crude mixture) was hydrogenated to yield a mixture of octadecane and 2-phenyldodecane (quantitative yield based on 2-phenyl-3-dodecene). An NMR sample was obtained by silica gel column chromatography using hexanes as the mobile. Fractions were analyzed by GC where pure fractions of 2-phenyldodecane were combined and concentrated under reduced pressure. $^1$H NMR (400 MHz, CDCl$_3$) δ 0.92 (t, J=7.2 Hz, 3H), 1.11-1.45 (m, 19H), 1.60 (m, 2H), 2.70 (psext, J=7.0 Hz, 1H), 7.17-7.24 (m, 3H), 7.29-7.35 (m, 2H). $^{13}$C NMR (101 MHz, CDCl$_3$) δ 17.4, 25.4, 25.8, 30.7, 32.3, 32.5, 32.5, 32.6, 32.7, 34.8, 41.1, 42.6, 126.1, 127.4, 128.6, 147.8.

2-Phenylhexadecane (2PhC$_{16}$ LAB, 2-phenylhexadecane 72% yield, 87.6% purity). A sample of high purity 2-phenylhexadecane was isolated by selective precipitation the hexacosane from 2-phenylhexadecane in the freezer (~−10° C.). $^1$H NMR (400 MHz, CDCl$_3$) δ 0.91 (t, J=7.0 Hz, 3H), 1.10-1.40 (m, 27H), 1.59 (m, 2H), 2.69 (psext, J=7.0 Hz, 1H), 7.16-7.23 (m, 3H), 7.27-7.35 (m, 2H). $^{13}$C NMR (101 MHz, CDCl$_3$) δ 14.1, 22.3, 22.7, 27.7, 29.4, 29.6, 29.7 (multiple overlapping resonances), 32.0, 38.5, 40.0, 125.7, 127.0, 128.2, 148.0.

Reaction 15. Synthesis of sodium 4-(decan-2-yl)benzenesulfonate (2PhC$_{10}$ LAS)

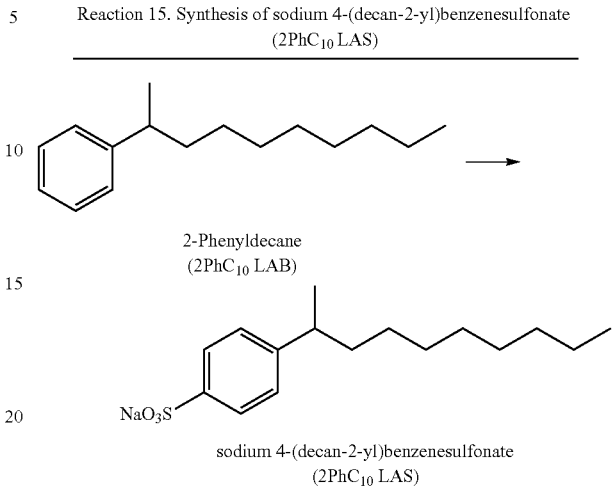

2-Phenyldecane
(2PhC$_{10}$ LAB)

sodium 4-(decan-2-yl)benzenesulfonate
(2PhC$_{10}$ LAS)

To a 5 L round bottom flask equipped with mechanical stirrer and an addition funnel was added 2-phenyldecane (412 g, 1.89 mol). The reaction mixture was sparged with argon, cooled to 10° C. and 1.25 weight % of oleum (556 g, 1.39 mol) was added dropwise, via addition funnel, to reaction mixture. The reaction mixture was stirred for 3 hours at room temperature then water (203 g, 11.3 mol) was added and the reaction mixture was transferred to a separatory funnel and allowed to separate. The bottom layer was discarded and the top layer was added slowly to a stirred solution of 10% NaOH (aq) (3 L) at 10° C. Upon complete addition the resulting suspension was stirred for an additional 30 minutes. The solid was subsequently isolated by filtration and washed twice with ice-cold water. The solids were air dried for 16 hours and vacuum dried at 80° C. to yield sodium, 4-(decan-2-yl)benzenesulfonate (457 g, 75.5% yield, 98.1% purity). $^1$H NMR (400 MHz, (CD$_3$)$_2$SO/ CDCl$_3$) δ 0.83 (t, J=7.0 Hz, 3H), 0.98-1.32 (m, 15H), 1.51 (pquart, J=7.3 Hz, 2H), 2.65 (psext, J=7.0 Hz, 1H), 7.11 (d, J=8.0 Hz, 2H), 7.57 (d, J=8.0 Hz, 2H). $^{13}$C NMR (101 MHz, (CD$_3$)$_2$SO/CDCl$_3$) δ 13.7, 21.9, 22.1, 27.0, 28.6, 28.8, 28.9, 31.1, 37.6, 38.8, 125.4, 125.8, 145.1, 147.8.

Reaction 16. Synthesis of sodium 4-(undecan-2-yl)benzenesulfonate (2PhC$_{11}$ LAS)

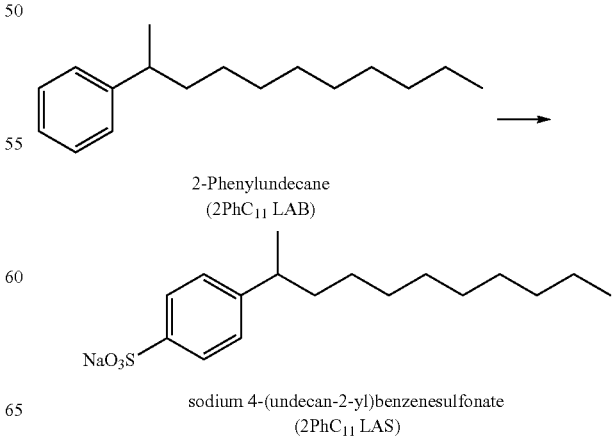

2-Phenylundecane
(2PhC$_{11}$ LAB)

sodium 4-(undecan-2-yl)benzenesulfonate
(2PhC$_{11}$ LAS)

To a 5 L round bottom flask equipped with mechanical stirrer and an addition funnel was added 2-phenylundecane (286 g, 1.23 mol). The reaction mixture was sparged with argon, cooled to 10° C. and 1.25 weight % of oleum (362 g, 0.91 mol) was added dropwise, via addition funnel. The reaction mixture was stirred for 3 hours at room temperature then water (133 g, 7.38 mol) was added and the reaction mixture was transferred to a separatory funnel and allowed to separate. The bottom layer was discarded and the top layer was added slowly to a stirred aqueous solution of 10% NaOH (2 L) at 10° C. Upon complete addition the resulting suspension was stirred for an additional 30 minutes. The solid was subsequently isolated by filtration and washed twice with ice-cold water. The solids were air dried for 16 hours and vacuum dried at 80° C. to yield sodium, 4-(undecan-2-yl)benzenesulfonate (320 g, 77.6% yield, 98.7% purity). $^1$H NMR (400 MHz, DMSO-$d_6$) δ 0.83 (t, J=6.6 Hz, 3H), 1.18-1.13 (m, 17H), 1.50 (q, J=7.2 Hz, 2H), 2.64 (sextet, J=6.8 Hz, 1H), 7.12 (d, J=8.0 Hz, 2H), 7.50 (d, J=8.0 Hz, 2H). $^{13}$C NMR (101 MHz, DMSO-$d_6$) δ 14.5, 22.5, 22.7, 27.4, 28.9, 29.2, 29.2, 29.2, 31.4, 37.7, 38.8, 123.4, 123.8, 143.1, 144.9.

Reaction 17. Synthesis of sodium 4-(dodecan-2-yl)benzenesulfonate (2PhC$_{12}$ LAS)

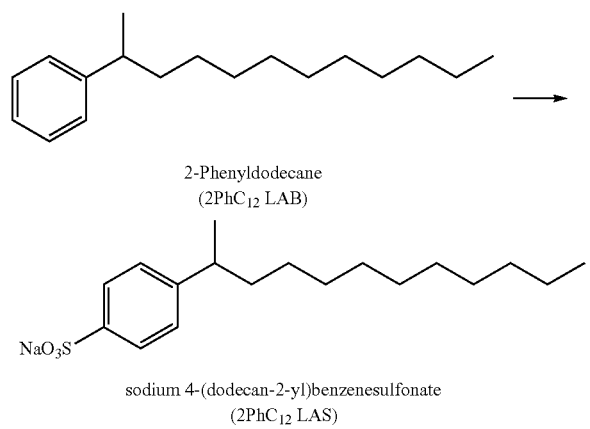

2-Phenyldodecane
(2PhC$_{12}$ LAB)

sodium 4-(dodecan-2-yl)benzenesulfonate
(2PhC$_{12}$ LAS)

To a 5 L round bottom flask equipped with mechanical stirrer and an addition funnel was added octadecane and 2-phenyldodecane mixture (1.73 kg, 28% 2-phenyldodecane). The reaction mixture was sparged with argon, warmed to 35° C. and 1.25 weight % of oleum (632 g, 1.58 mol) was added dropwise, via addition funnel, to reaction mixture. The reaction mixture was stirred for 1.5 hours at room temperature. Upon completion, the reaction mixture was heated to 50° C. and transferred to a separatory funnel and allowed to separate. The bottom layer was added slowly to a stirred solution of 15% NaOH (aq) (2 L) at 10° C. Upon complete addition the resulting suspension was stirred for an additional 60 minutes. The solid was subsequently isolated by filtration and washed twice with ice-cold water. The solids were air dried for 16 hours and vacuum dried at 80° C. to yield sodium, 4-(dodecan-2-yl)benzenesulfonate (555 g, 80.8% yield, 98.5% purity). $^1$H NMR (400 MHz, (CD$_3$)$_2$SO/CDCl$_3$) δ 0.84 (t, J=7.0 Hz, 3H), 0.95-1.38 (m, 19H), 1.51 (pquart, J=7.3 Hz, 2H), 2.65 (psext, J=7.0 Hz, 1H), 7.11 (d, J=7.6 Hz, 2H), 7.56 (d, J=8.4 Hz, 2H). $^{13}$C NMR (101 MHz, (CD$_3$)$_2$SO/CDCl$_3$) δ 13.8, 22.0, 22.1, 27.0, 28.9, 28.9, 28.9, 28.9, 31.2, 37.6, 38.8, 125.4, 125.8, 145.3, 147.7.

Reaction 18. Synthesis of sodium 4-(hexadecan-2-yl)benzenesulfonate (2PhC$_{16}$ LAS)

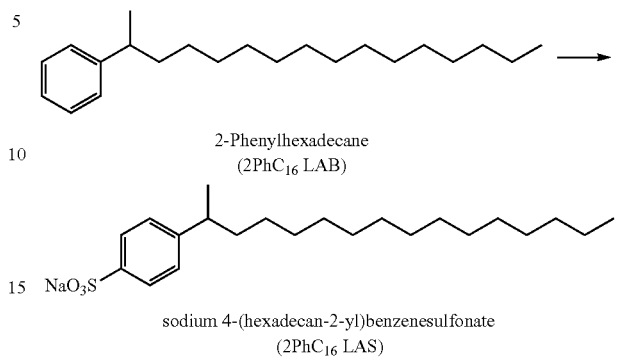

2-Phenylhexadecane
(2PhC$_{16}$ LAB)

sodium 4-(hexadecan-2-yl)benzenesulfonate
(2PhC$_{16}$ LAS)

To a 1 L round bottom flask equipped with stirbar and an addition funnel was added hexacosane and 2-phenylhexadecane mixture (136.1 g, 87.6% purity 2-phenylhexadecane). The reaction mixture was sparged with argon, warmed to 35° C. and 1.3 weight % of oleum (155.0 g, 0.388. mol) was added dropwise, via addition funnel, to reaction mixture. The reaction mixture was stirred for 1.5 hours at room temperature. Upon completion, the reaction mixture was transferred to a separatory funnel with 200 mL of hexane and allowed to separate. No separation was observed, so the entire crude material was added slowly to a stirred solution of 15% NaOH (aq) (800 mL) at 10° C. Upon complete addition the resulting suspension was stirred for an additional 90 minutes. The solid was subsequently isolated by filtration and washed twice with ice-cold water. The solids were air dried for 16 hours and vacuum dried at 80° C. for 2 days to yield sodium, 4-(hexadecan-2-yl) benzenesulfonate (151 g, 94.7% yield, 98.8% purity). $^1$H NMR (400 MHz, (CD$_3$)$_2$SO) δ 0.85 (t, J=7.2 Hz, 3H), 0.98-1.38 (m, 27H), 1.51 (pquart, J=7.1 Hz, 2H), 2.65 (psext, J=7.0 Hz, 1H), 7.13 (d, J=8.0 Hz, 2H), 7.52 (d, J=8.4 Hz, 2H). $^{13}$C NMR (101 MHz, (CD$_3$)$_2$SO) δ 13.8, 22.0, 22.2, 27.0, 28.6, 28.9 (multiple overlapping resonances), 31.2, 37.6, 38.8, 125.5, 125.9, 145.8, 147.6.

Reaction 19. General sulfonation procedure to the mixtures of 2PhLAB yield 2PhLAS

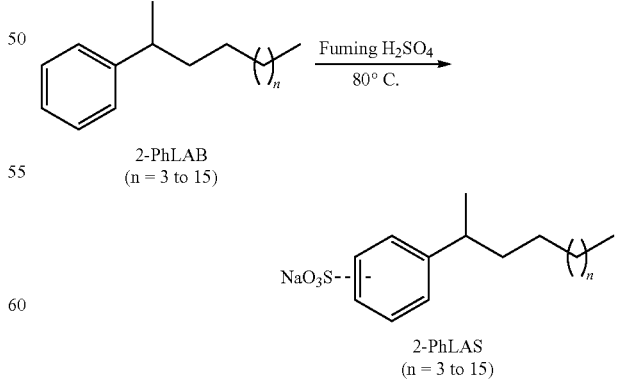

2-PhLAB
(n = 3 to 15)

2-PhLAS
(n = 3 to 15)

2-PhLAB was added to a round bottom flask equipped with a magnetic stirbar and cooled to 10° C. Oleum (1.25 weight %, 20% free SO$_3$) was added drop wise to reaction mixture while maintaining temperature of 25° C. during addition. The reaction was stirred for 2.5 hours at 25° C. Water (0.24 wt %) was added and the reaction mixture was poured into a separatory funnel to yield two layers. The bottom layer was discarded and the top layer was slowly added to a stirred solution of 5% NaOH in water at 10° C. Solid formation was observed and mixture was allowed to stir an additional 30 minutes after complete addition. The 2-PhLAS was isolated by filtration, washed twice with ice-cold water, and dried in vacuo at 50° C. to 80° C. to afford an off-white solid.

Examples of 2-PhLAS produced by this procedure include but not limited to sodium 4-(octan-2-yl)benzenesulfonate (2-PhC$_8$ LAS), sodium 4-(non-2-yl)benzenesulfonate (2-PhC$_9$ LAS), sodium 4-(decan-2-yl)benzenesulfonate (2-PhC$_{10}$ LAS), sodium 4-(undecan-2-yl)benzenesulfonate (2-PhC$_{11}$ LAS), sodium 4-(dodecan-2-yl)benzenesulfonate (2-PhC$_{12}$ LAS), sodium 4-(tridecan-2-yl)benzenesulfonate (2-PhC$_{13}$ LAS), sodium 4-(tetradecan-2-yl)benzenesulfonate (2-PhC$_{14}$ LAS), sodium 4-(pentadecan-2-yl)benzenesulfonate (2-PhC$_{is}$ LAS), sodium 4-(hexadecan-2-yl)benzenesulfonate (2-PhC$_{16}$ LAS), sodium 4-(septadecan-2-yl)benzenesulfonate (2-PhC$_{17}$ LAS), sodium 4-(octadecan-2-yl)benzenesulfonate (2-PhC$_{18}$ LAS), sodium 4-(nonadecan-2-yl)benzenesulfonate (2-PhC$_{19}$ LAS), and), and sodium 4-(eicosan-2-yl)benzenesulfonate (2-PhC$_{20}$ LAS).

Krafft Point and CMC Data

Krafft Point or Krafft Temperature is defined as the minimum concentration of surfactant needed to form a micelle at a given temperature. Surfactants form micelles above their Krafft Point and the solubility in water increases abruptly. The Krafft point was determined by the abrupt increase in the electrical conductivity of as a function of temperature. The intersection of the two solubility lines is the Krafft Point.

The Critical Micelle Concentration (CMC) is defined as the concentration of surfactants above which micelles form and all additional surfactants added to the system go to micelles. The CMC is measured by the electrical conductivity-concentration curve at constant temperature. Table 5 contains the Krafft temperatures and CMC results.

TABLE 5

Krafft Point, CMC and Surface Tension Data

| Compound | Purity | Krafft Point (wt %) | CMC (mmol/L) at Temp (° C.) | Surface Tension[3] |
|---|---|---|---|---|
| 2-PhC$_{10}$ LAS | >98% | 22.5° C. (0.19) | 4.4 at 22.0° C. | 43 dynes/cm |
| 2-PhC$_{11}$ LAS | >98% | 23.0° C. (0.125) | 1.9 at 22.0° C. | 43 dynes/cm |
| 2-PhC$_{12}$ LAS | >98% | 22.5° C. (0.075) | 2.1 at 22.5° C. | 41 dynes/cm |
| 2-PhC$_{16}$ LAS | >98% | 45.0° C. (0.125) | 1.5 at 44.0° C. | 44 dynes/cm |
| 2-PhC$_{10}$ LAS[1] | 91% | 22.0° C. (NR[2]) | 4.5 at 20° C. | NR |

[1]N.M. van Os; R. Kok; T.A.B.M. Bolsman *Tenside Surf Det.* 1992, 29 175.
[2]NR is Not reported
[3]Surface tension above CMC To verify that the hydrovinylation of styrene produces 3-phenyl-1-butene and not 2-phenyl-1-butene, 3-phenyl linear alkyl benzene was synthesized by traditional methods and compared to 2-phenyl linear alkyl benzene by GC analysis. 3-Phenyl-1-butene yields 2-phenyl linear alkyl benzene while 2-phenyl-1-butene yields 3-phenyl linear alkyl benzene by our reported cross metathesis methodology.

3-Phenylundecane was synthesized by phenyl Grignard's addition to 3-undecanone, followed by hydrogenation. Equal amounts of 2-Phenylundecane (99.3% purity) and 3-phenylundecane (98.5% purity) were co-injected and analyzed by GC. The GC method and conditions is as described above. The results are represented in Table 6.

TABLE 6

GC Comparison of 2-phenylundecane and 3-phenylundecane

| Compound | GC Purity | Rt (min) | Comments |
|---|---|---|---|
| 2-Phenyldecane* | 0.75% | 10.095 min | Impurity in 3-phenylundecane |
| 3-Phenylundecane | 48.25% | 10.921 min | |
| 1-Phenydecane* | 0.38% | 10.991 min | Impurity in 2-phenylundecane |
| 2-Phenylundecane | 50.62% | 11.371 min | |

*GC-MS library suggested compound

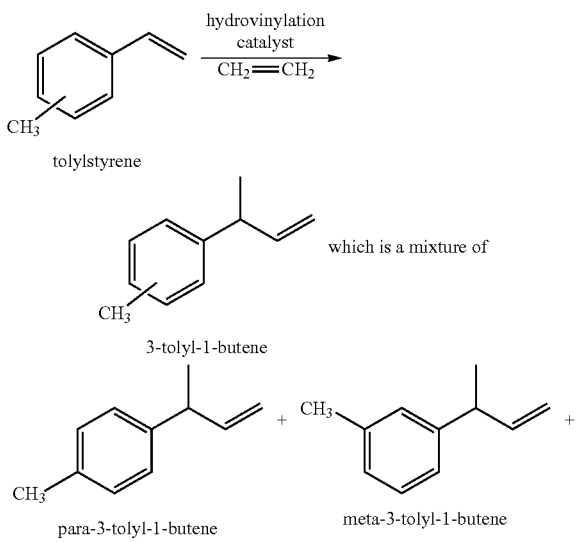

Reaction 20. Synthesis of 3-tolyl-1-butene by hydrovinylation of tolylstryene.

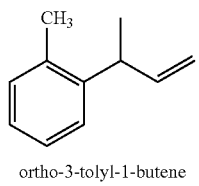

In an argon filled glovebox, (PPh$_3$)$_2$CoCl$_2$ (0.080 g, 0.12 mmol), dichloromethane (5.0 mL), and tolylstyrene (12.1 mL, 91.7 mmol, [60% meta, 40% para, 1% ortho]) were combined in a glass lined 25 mL Parr reactor equipped with a magnetic stirbar. The reactor was sealed and cooled to 0° C. while the headspace was purged with ethylene. A solution of diethylaluminum chloride in hexanes (0.61 mL, 1.0 M, 0.61 mmol) was introduced. The reactor was promptly sealed and charged with ethylene (435 psi). After 20 minutes the pressure was released the reaction passed through a plug of silica gel. The silica gel was washed with hexanes (2×20 mL) and the organic fractions were combined and concentrated under rotary evaporation. Subsequent purification by vacuum distillation afforded 3-tolyl-1-butene (Bpt 36.5° C. to 38.5° C. at 0.65 mmHg, 12.5 g, 93.2% yield and >99% purity). 3-Tolyl-1-butene was produced in >99% isomeric purity (neither 2-tolyl-2-butene nor 2-tolyl-1-butene isomers were detected by $^1$H NMR and <0.5% 2-tolyl-2-butene was detected by GC analysis).

$^1$H NMR (400 MHz, CDCl$_3$) δ 1.42 (m, 3H), 2.39-2.41 (m, 3H), 3.50 (p, J=6.6 Hz, 1H), 5.05-5.17 (m, 2H), 6.07 (m, 1H), 7.05-7.30 (m, 4H).

$^{13}$C NMR (101 MHz, CDCl$_3$) δ 20.7, 20.8, 21.0, 21.4, 42.8, 43.1, 112.9, 112.9, 124.2, 136.8, 127.1, 128.0, 128.3, 129.1, 135.5, 137.9, 142.6, 143.3, 143.5, 145.5.

Reaction 21. Preparation of 2-tolyl-3-octene.

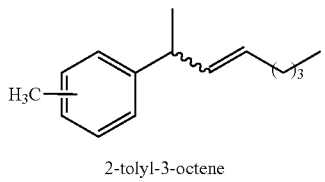

2-tolyl-3-octene

Inside an argon filled glovebox, a round bottom flask equipped with a reflux condenser and magnetic stir bar was charged with 5-decene (9.6 g, 68 mmol) and 3-tolyl-1-butene (5.0 g, 34 mmol). The reaction mixture was heated to 40° C. and a solution of C827 in dichloromethane (57 μL, 15 mM, 25 ppm) was subsequently added to the reaction mixture. The reaction mixture was stirred at 40° C. under 7 mmHg vacuum for 2 hours then allowed to cool to room temperature before filtration through a plug of silica gel. The silica gel was washed with hexanes (2×50 mL) and all organic fractions combined and concentrated under rotary evaporation. Subsequent purification by column chromatography (SiO$_2$, hexanes) afforded 2-tolyl-3-octene (5.1 g, 74%, >99% purity).

$^1$H NMR (400 MHz, CDCl$_3$) δ 0.89-0.96 (m, 3H), 1.30-1.44 (m, 7H), 2.00-2.10 (m, 2H), 2.34-2.38 (m, 3H), 3.41 (p, J=6.9 Hz, 1H), 5.43-5.53 (m, 1H), 5.57-5.66 (m, 1H), 7.10-7.25 (m, 4H).

$^{13}$C NMR (101 MHz, CDCl$_3$) δ 14.0, 21.0, 21.5, 21.6, 22.2, 31.7, 32.2, 41.8, 42.2, 124.1, 126.6, 127.0, 127.9, 128.2, 129.0, 129.0, 129.1, 135.0, 135.1, 135.3, 137.8, 143.6, 146.5.

Reaction 22. Preparation of 2-tolyl-3-nonene.

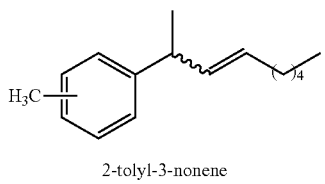

2-tolyl-3-nonene

Inside an argon filled glovebox, a septa capped scintillation vial equipped with a magnetic stir bar was charged with 1-heptene (0.52 g, 5.1 mmol) and 3-tolyl-1-butene (0.25 g, 1.7 mmol). The reaction mixture was heated to 40° C. and a solution of C827 in dichloromethane (71 μL, 7.3 mM, 300 ppm) was subsequently added to the reaction mixture. The reaction was vented by puncturing the septum with a needle and allowed to stir at 40° C. After 2 hours, the reaction mixture was cooled to room temperature and filtered through a plug of silica gel. The silica gel was washed with hexanes (2×10 mL) and all organic fractions combined concentrated under rotary evaporation. Subsequent purification by column chromatography (SiO$_2$, hexanes) afforded 2-tolyl-3-nonene (140 mg, 38%, >97% purity).

$^1$H NMR (400 MHz, CDCl$_3$) δ 0.90-0.97 (m, 3H), 1.28-1.48 (m, 9H), 2.01-2.10 (m, 2H), 2.35-2.40 (m, 3H), 3.43 (p, J=6.9 Hz, 1H), 5.44-5.55 (m, 1H), 5.58-5.67 (m, 1H), 7.10-7.26 (m, 4H).

$^{13}$C NMR (101 MHz, CDCl$_3$) δ 14.1, 21.0, 21.5, 21.6, 22.5, 29.2, 31.4, 32.5, 41.9, 42.2, 124.1, 126.6, 127.0, 127.9, 128.2, 129.0, 129.1, 129.2, 135.0, 135.1, 135.3, 137.8, 143.6, 146.5.

Reaction 23. Preparation of 2-tolyl-3-decene.

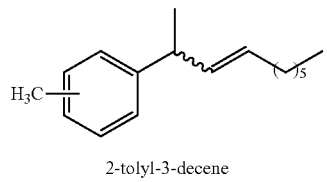

2-tolyl-3-decene

Inside an argon filled glovebox, a scintillation vial equipped with a magnetic stir bar was charged with 7-tetradecene (0.51 g, 2.6 mmol) and 3-tolyl-1-butene (0.25 g, 1.7 mmol). The reaction mixture was heated to 40° C. and a solution of C827 in dichloromethane (5.7 μL, 15 mM, 50 ppm) was subsequently added to the reaction mixture. The reaction mixture was allowed to stir at 40° C. for 2 hours hours then cooled to room temperature before filtration through a plug of silica gel. The silica gel was washed with hexanes (2×10 mL) and all organic fractions combined and concentrated under rotary evaporation. Subsequent purification by column chromatography (SiO$_2$, hexanes) afforded 2-tolyl-3-decene (160 mg, 39%, >99% purity).

$^1$H NMR (400 MHz, CDCl$_3$) δ 0.88-0.95 (m, 3H), 1.25-1.44 (m, 11H), 2.00-2.09 (m, 2H), 2.32-2.38 (m, 3H), 3.41 (p, J=6.8 Hz, 1H), 5.43-5.53 (m, 1H), 5.56-5.66 (m, 1H), 7.10-7.26 (m, 4H).

$^{13}$C NMR (101 MHz, CDCl$_3$) δ 14.1, 21.0, 21.5, 21.6, 22.7, 28.9, 29.5, 31.7, 32.5, 41.8, 42.2, 124.1, 126.6, 127.0, 127.9, 128.2, 129.0, 129.1, 129.2, 135.0, 135.1, 135.3, 137.8, 143.6, 146.6.

Reaction 24. Preparation of 2-tolyl-3-undecene.

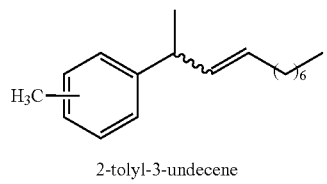

2-tolyl-3-undecene

Inside an argon filled glovebox, a round bottom flask equipped with a magnetic stir bar was charged with 1-nonene (0.56 g, 4.0 mmol) and 3-tolyl-1-butene (0.50 g, 3.4 mol). A solution of C627 in dichloromethane (170 µL, 16 mM, 80 ppm) was prepared inside the glovebox and added to this reaction mixture. The reaction mixture was brought outside the glovebox and placed under vacuum (diaphragm pump) where it was stirred for 2 hours at room temperature. The reaction mixture was then filtered through a plug of silica gel. The silica gel was washed with hexanes (2×10 mL) and all organic fractions combined and concentrated under rotary evaporation. Subsequent purification by column chromatography (SiO$_2$, hexanes) afforded 2-tolyl-3-undecene (200 mg, 24%, >90% purity).

$^1$H NMR (400 MHz, CDCl$_3$) δ 0.86-0.94 (m, 3H), 1.21-1.44 (m, 13H), 1.98-2.06 (m, 2H), 2.31-2.37 (m, 3H), 3.40 (p, J=7.0 Hz, 1H), 5.41-5.53 (m, 1H), 5.55-5.65 (m, 1H), 7.10-7.26 (m, 4H).

$^{13}$C NMR (101 MHz, CDCl$_3$) δ 14.1, 21.0, 21.5, 21.6, 22.7, 29.1, 29.5, 31.9, 32.5, 41.8, 42.2, 124.1, 126.6, 127.0, 127.9, 128.2, 129.0, 129.1, 129.2, 135.0, 135.1, 135.3, 137.8, 143.6, 146.6.

Reaction 25. Preparation of 2-tolyl-3-dodecene.

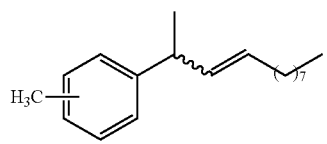

2-tolyl-3-dodecene

Inside an argon filled glovebox, a scintillation vial equipped with a magnetic stir bar was charged with 9-octadecene (0.76 g, 2.6 mmol) and 3-tolyl-1-butene (0.25 g, 1.7 mmol). The reaction mixture was heated to 40° C. and a solution of C827 in dichloromethane (5.7 µL, 15 mM, 50 ppm) was subsequently added to the reaction mixture. The reaction mixture was allowed to stir at 40° C. for 2 hours. The reaction mixture was then cooled to room temperature and filtered through a plug of silica gel. The silica gel was washed with hexanes (2×15 mL) and all organic fractions combined and concentrated under rotary evaporation. Subsequent purification by column chromatography (SiO$_2$, hexanes) afforded 2-tolyl-3-dodecene (180 mg, 41%, >99% purity).

$^1$H NMR (400 MHz, CDCl$_3$) δ 0.89-0.96 (m, 3H), 1.25-1.45 (m, 15H), 2.00-2.09 (m, 2H), 2.34-2.39 (m, 3H), 3.42 (p, J=6.9 Hz, 1H), 5.44-5.54 (m, 1H), 5.58-5.66 (m, 1H), 7.10-7.26 (m, 4H).

$^{13}$C NMR (101 MHz, CDCl$_3$) δ 14.1, 21.0, 21.5, 21.6, 22.7, 29.2, 29.3, 29.4, 29.5, 29.6, 31.9, 32.6, 41.9, 42.2, 124.1, 126.6, 127.0, 128.0, 128.2, 129.0, 129.1, 129.2, 135.0, 135.1, 135.3, 137.8, 143.6, 146.6.

Reaction 26. Preparation of 2-tolyl-3-tridecene.

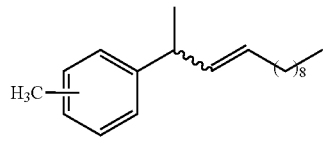

2-tolyl-3-tridecene

Inside an argon filled glovebox, a round bottom flask equipped with a reflux condenser and magnetic stir bar was loaded with 1-undecene (1.59 g, 10.3 mmol) and 3-tolyl-1-butene (0.50 g, 3.4 mmol). The reaction mixture was heated to 40° C. and a solution of C827 in dichloromethane (5.7 µL, 15 mM, 25 ppm) was subsequently added to the reaction mixture. The reaction mixture was allowed to stir at 40° C. with 7 mmHg vacuum for 2 hours. The reaction mixture was then cooled to room temperature and filtered through a plug of silica gel. The silica gel was washed with hexanes (2×30 mL) and all organic fractions combined concentrated under rotary evaporation. Subsequent purification by column chromatography (SiO$_2$, hexanes) afforded 2-tolyl-3-tridecene (40. mg, 4.3%, >94% purity).

$^1$H NMR (400 MHz, CDCl$_3$) δ 0.87-0.95 (m, 3H), 1.23-1.44 (m, 17H), 1.98-2.06 (m, 2H), 2.32-2.37 (m, 3H), 3.40 (p, J=6.8 Hz, 1H), 5.41-5.51 (m, 1H), 5.55-5.64 (m, 1H), 7.10-7.26 (m, 4H).

$^{13}$C NMR (101 MHz, CDCl$_3$) δ 14.1, 21.0, 21.5, 21.6, 22.7, 29.2, 29.3, 29.4, 29.5, 29.6, 31.9, 32.5, 41.8, 42.2, 124.1, 126.6, 127.0, 127.9, 128.2, 129.0, 129.1, 129.2, 134.9, 135.1, 135.3, 137.8, 143.6, 146.6.

Reaction 27. Preparation of 2-tolyl-3-tetradecene.

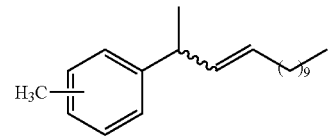

2-tolyl-3-tetradecene

Inside an argon filled glovebox, a 20 mL oven-dried scintillation vial equipped with a magnetic stirbar was added 1-dodecene (1.73 g, 10.3 mmol) and 3-tolyl-1-butene (0.50 g, 3.4 mmol). The reaction mixture was heated to 40° C. and a solution of C827 in dichloromethane (9.0 µL, 10 mM, 25 ppm) was subsequently added to the reaction mixture. The reaction mixture was allowed to stir at 40° C. with 7 mmHg vacuum for 2 hours. The reaction mixture was then cooled to room temperature, diluted with hexanes, and filtered through a plug of silica gel. The silica gel was washed with hexanes (2×30 mL) and all organic fractions combined concentrated under rotary evaporation. Subsequent purification by column chromatography (SiO$_2$, hexanes) afforded 2-tolyl-3-tetradecene (36 mg, 3.7%, >98% purity).

$^1$H NMR (400 MHz, CDCl$_3$) δ 0.86-0.93 (m, 3H), 1.22-1.45 (m, 19H), 1.99-2.07 (m, 2H), 2.30-2.38 (m, 3H), 3.41 (p, J=6.9 Hz, 1H), 5.40-5.49 (m, 1H), 5.54-5.64 (m, 1H), 7.11-7.26 (m, 4H).

$^{13}$C NMR (101 MHz, CDCl$_3$) δ 14.1, 21.0, 21.5, 21.6, 22.7, 29.2, 29.3, 29.4, 29.5, 29.6, 31.9, 32.5, 41.8, 42.2, 124.1, 126.6, 127.0, 127.9, 128.2, 129.0, 129.1, 129.2, 134.9, 135.1, 135.3, 137.8, 143.6, 146.6.

Reaction 28. Preparation of 2-tolyl-3-hexadecene.

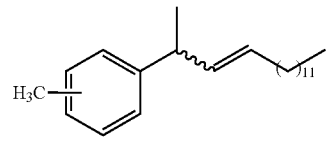

2-tolyl-3-hexadecene

Inside an argon filled glovebox, a round bottom flask equipped with a magnetic stir bar was loaded with 1-tetradecene (0.88 g, 4.5 mmol) and 3-tolyl-1-butene (0.50 g, 3.4 mmol). A solution of C627 in dichloromethane (170 μL, 16 mM, 80 ppm) was prepared inside the glovebox and added to this reaction. The reaction mixture was brought outside the glovebox and placed under vacuum (diaphragm pump) where it was stirred for 2 hours at room temperature. The reaction mixture was then filtered through a plug of silica gel. The silica gel was washed with hexanes (2×10 mL) and all organic fractions combined and concentrated under rotary evaporation. Subsequent purification by column chromatography (SiO$_2$, hexanes) afforded 2-tolyl-3-hexadecene (240 mg, 22%, >96% purity).

$^1$H NMR (400 MHz, CDCl$_3$) δ 0.89-0.96 (m, 3H), 1.25-1.44 (m, 23H), 1.99-2.08 (m, 2H), 2.33-2.36 (m, 3H), 3.41 (p, J=7.0 Hz, 1H), 5.42-5.53 (m, 1H), 5.57-5.66 (m, 1H), 7.10-7.26 (m, 4H).

$^{13}$C NMR (101 MHz, CDCl$_3$) δ 14.1, 21.0, 21.5, 21.6, 22.7, 29.2, 29.4, 29.5, 29.7, 29.7, 31.9, 32.5, 41.8, 42.2, 124.1, 126.6, 127.0, 127.9, 128.2, 129.0, 129.1, 129.2, 134.9, 135.1, 135.3, 137.8, 143.6, 146.5.

Reaction 29. Preparation of 2-tolyloctane.

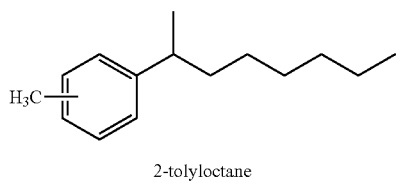

2-tolyloctane

A Parr reactor equipped with a pressure seal, glass liner and magnetic stir bar was charged with 2-tolyl-3-octene (2.0 g, 9.9 mmol), ethyl acetate (9.0 mL), and Pd/C (21.0 mg, 2.5 mol % loading). The reaction mixture was sparged with hydrogen, heated to 40° C., and pressurized to 25 psig hydrogen. The reaction was allowed to stir at 40° C. under 25 psig hydrogen until complete conversion was determined by gas chromatography. The reaction vessel was then vented, cooled to room temperature, and the reaction mixture was filtered through a plug of silica gel. The silica gel was washed with hexanes (2×40 mL) and all organic fractions combined. Subsequent evaporation of solvent under rotary evaporation afforded 2-tolyloctane (2.0 g, 99%, >98% purity).

$^1$H NMR (400 MHz, CDCl$_3$) δ 0.85-0.92 (m, 3H), 1.11-1.35 (m, 11H), 1.49-1.66 (m, 2H), 2.32-2.38 (m, 3H), 2.59-2.71 (m, 1H), 6.98-7.23 (m, 4H).

$^{13}$C NMR (101 MHz, CDCl$_3$) δ 14.1, 21.0, 21.5, 22.3, 22.4, 22.7, 27.7, 29.4, 31.8, 38.5, 38.5, 39.5, 39.9, 124.0, 126.5, 126.8, 127.8, 128.1, 128.9, 135.1, 137.7, 145.0, 148.0.

Reaction 30. Preparation of 2-tolyldodecane.

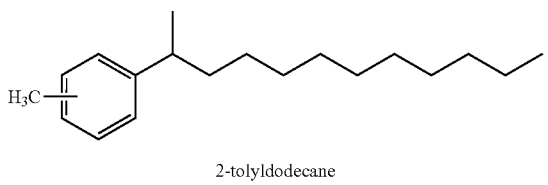

2-tolyldodecane

A Parr reactor equipped with a pressure seal, glass liner and magnetic stir bar was charged with 2-tolyl-3-dodecene (2.0 g, 7.7 mmol), ethyl acetate (8.0 mL), and Pd/C (20.6 mg, 2.5 mol % loading). The reaction mixture was sparged with hydrogen, heated to 40° C., and pressurized to 25 psig hydrogen. The reaction was allowed to stir at 40° C. under 25 psig hydrogen until complete conversion was determined by gas chromatography. The reaction vessel was then vented, cooled to room temperature, and the reaction mixture was filtered through a plug of silica gel. The silica gel was washed with hexanes (2×40 mL) and all organic fractions combined. Subsequent evaporation of solvent under rotary evaporation afforded 2-tolyldodecane (2.0 g, 99%, >98% purity).

$^1$H NMR (400 MHz, CDCl$_3$) δ 0.88-0.94 (m, 3H), 1.14-1.37 (m, 19H), 1.49-1.67 (m, 2H), 2.33-2.38 (m, 3H), 2.59-2.72 (m, 1H), 6.98-7.23 (m, 4H).

$^{13}$C NMR (101 MHz, CDCl$_3$) δ 14.1, 21.0, 21.5, 22.3, 22.4, 22.7, 27.8, 29.4, 29.6, 29.6, 29.7, 29.8, 31.9, 38.5, 38.5, 39.5, 39.9, 124.0, 126.5, 126.8, 127.8, 128.1, 128.9, 135.1, 137.7, 145.0, 148.0.

Reaction 31. Preparation of sodium 2-tolyloctanesulfonate.

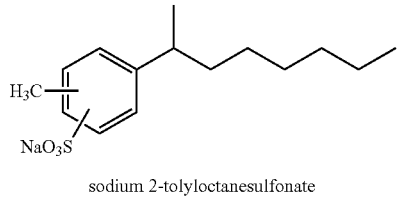

sodium 2-tolyloctanesulfonate

To a round bottom flask equipped with a stirbar was added 2-tolyloctane (1.5 g, 7.3 mmol). The reaction mixture was sparged with argon, cooled to 0° C. and oleum (2.0 g, 4.9 mmol, 20% free SO$_3$) was added dropwise, via addition syringe, to reaction mixture. The reaction mixture was stirred for 45 minutes at 0° C. and then 1.5 hour at room temperature. Then, the reaction mixture was added slowly to a stirred solution of 20% NaOH (aq) (4.5 mL) at 0° C. Upon complete addition the resulting suspension was stirred for an additional 1.5 hour. The solid was subsequently isolated by filtration, washed with ice-cold water (2×15 mL), and vacuum dried at 80° C. to yield sodium 2-tolyloctanesulfonate (280 mg, 12%, >98% purity).

$^1$H NMR (400 MHz, DMSO-d$_6$) δ 0.77-0.85 (m, 3H), 0.98-1.30 (m, 11H), 1.43-1.54 (m, 2H), 2.48 (s, 3H), 2.53-2.65 (m, 1H), 6.88-6.95 (m, 2H), 7.58-7.64 (m, 1H).

$^{13}$C NMR (101 MHz, DMSO-d$_6$) δ 13.8, 20.1, 22.0, 22.2, 27.0, 28.6, 31.1, 37.6, 38.7, 122.8, 126.5, 129.1, 135.2, 143.8, 147.7.

Reaction 32. Preparation of sodium 2-tolyldodecanesulfonate.

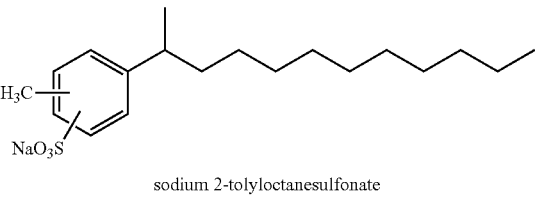

sodium 2-tolyloctanesulfonate

To a round bottom flask equipped with a stirbar was added 2-tolyldodecane (1.8 g, 6.9 mmol). The reaction mixture was sparged with argon, cooled to 0° C. and oleum (2.34 g, 5.85 mmol, 20% free SO$_3$) was added dropwise, via addition syringe, to reaction mixture. The reaction mixture was stirred for 45 minutes at 0° C. and then 1.5 hour at room temperature. Then, the reaction mixture was added slowly to a stirred solution of 20% NaOH (aq) (10 mL) at 0° C. Upon complete addition the resulting suspension was stirred for an additional 1.5 hour. The solid was subsequently isolated by filtration, washed with ice-cold water (2×15 mL), and vacuum dried at 80° C. to yield sodium 2-tolyldodecane-sulfonate (580 mg, 23%, >98% purity).

$^1$H NMR (400 MHz, DMSO-d$_6$) δ 0.76-0.90 (m, 3H), 0.98-1.34 (m, 19H), 1.42-1.56 (m, 2H), 2.48 (s, 3H), 2.54-2.64 (m, 1H), 6.85-6.97 (m, 2H), 7.58-7.66 (m, 1H).

$^{13}$CNMR (101 MHz, DMSO-d$_6$) δ 13.9, 20.1, 22.0, 22.2, 27.1, 28.6, 28.9, 29.0, 29.0, 31.2, 37.6, 38.7, 122.8, 126.6, 129.0, 135.2, 143.8, 147.7.

The claimed invention is:

1. A method of making at least one cross metathesis product, the method comprising:
    forming a first composition comprising at least one cross metathesis substrate, at least one hydrovinylation catalyst, and ethylene;
    subjecting the first composition to conditions effective to promote a hydrovinylation reaction to form at least one hydrovinylated cross metathesis substrate;
    forming a second composition comprising the at least one hydrovinylated cross metathesis substrate, at least one olefinic substrate, and at least one olefin metathesis catalyst;
    subjecting the second composition to conditions effective to promote a cross metathesis reaction to form at least one cross metathesis product, wherein the at least one cross metathesis product is at least one 2-phenyl linear alkene benzene;
    subjecting the at least one 2-phenyl linear alkene benzene to conditions effective to promote olefin hydrogenation to form at least one 2-phenyl linear alkyl benzene; and
    subjecting the at least one 2-phenyl linear alkene benzene to conditions effective to promote an aromatic sulfonation reaction to form at least one 2-phenyl linear alkyl benzene sulfonate.

2. A method of making at least one cross metathesis product, the method comprising:
    forming a first composition comprising at least one cross metathesis substrate, at least one hydrovinylation catalyst, and ethylene;
    subjecting the first composition to conditions effective to promote a hydrovinylation reaction to form at least one hydrovinylated cross metathesis substrate;
    forming a second composition comprising the at least one hydrovinylated cross metathesis substrate, at least one olefinic substrate, and at least one olefin metathesis catalyst;
    subjecting the second composition to conditions effective to promote a cross metathesis reaction to form at least one cross metathesis product, wherein the at least one cross metathesis product is at least one 2-tolyl linear alkene benzene; and
    subjecting the at least one 2-tolyl linear alkene benzene to conditions effective to promote olefin hydrogenation to form at least one 2-tolyl linear alkyl benzene.

3. A method of making 2-tolyl linear alkyl benzene sulfonates, comprising subjecting at least one 2-tolyl linear alkyl benzene to conditions effective to promote an aromatic sulfonation reaction to form at least one 2-tolyl linear alkyl benzene sulfonate.

4. A method of making 2-phenyl linear alkyl benzene sulfonates, the method comprising:
    forming a first composition comprising styrene, at least one hydrovinylation catalyst, and ethylene;
    subjecting the first composition to conditions effective to promote a hydrovinylation reaction to form 3-phenyl-1-butene;
    forming a second composition comprising 3-phenyl-1-butene, at least one olefinic substrate, and at least one olefin metathesis catalyst, wherein the at least one olefinic substrate is selected from a linear alpha olefin, or a linear internal olefin, or a combination thereof;
    subjecting the second composition to conditions effective to promote a cross metathesis reaction to form at least one 2-phenyl linear alkene benzene;
    subjecting the at least one 2-phenyl linear alkene benzene to conditions effective to promote olefin hydrogenation to form at least one 2-phenyl linear alkylbenzene; and
    subjecting the at least one 2-phenyl linear alkylbenzene to conditions effective to promote aromatic sulfonation of the at least one 2-phenyl linear alkylbenzene.

5. A method of making 2-tolyl linear alkyl benzene sulfonates, the method comprising:
    forming a first composition comprising tolylstyrene, at least one hydrovinylation catalyst, and ethylene;
    subjecting the first composition to conditions effective to promote a hydrovinylation reaction to form 3-tolyl-1-butene;
    forming a second composition comprising 3-tolyl-1-butene, at least one olefinic substrate, and at least one olefin metathesis catalyst, wherein the at least one olefinic substrate is selected from a linear alpha olefin, or a linear internal olefin, or a combination thereof;
    subjecting the second composition to conditions effective to promote a cross metathesis reaction to form at least one 2-tolyl linear alkene benzene;
    subjecting the at least one 2-tolyl linear alkene benzene to conditions effective to promote olefin hydrogenation to form at least one 2-tolyl linear alkylbenzene; and
    subjecting the at least one 2-tolyl linear alkylbenzene to conditions effective to promote aromatic sulfonation of the at least one 2-tolyl linear alkylbenzene.

6. The method according to claim 4, wherein the 2-phenyl linear alkyl benzene sulfonates are selected from: sodium 4-(decan-2-yl)benzenesulfonate, sodium 4-(undecan-2-yl)benzenesulfonate, sodium 4-(dodecan-2-yl)benzenesulfonate and sodium 4-(hexadecan-2-yl)benzenesulfonate.

7. The method according to claim 5, wherein the 2-tolyl linear alkyl benzene sulfonates are selected from: sodium 2-tolyloctanesulfonate and sodium 2-tolyldodecanesulfonate.

* * * * *